United States Patent [19]
Neev

[11] Patent Number: 6,156,030
[45] Date of Patent: Dec. 5, 2000

[54] METHOD AND APPARATUS FOR HIGH PRECISION VARIABLE RATE MATERIAL REMOVAL AND MODIFICATION

[75] Inventor: Joseph Neev, Laguna Beach, Calif.

[73] Assignee: Y-Beam Technologies, Inc., Lake Forest, Calif.

[21] Appl. No.: 09/054,834

[22] Filed: Apr. 3, 1998

Related U.S. Application Data

[60] Provisional application No. 60/050,416, Jun. 4, 1997.

[51] Int. Cl.$^7$ .................................................. A61B 18/18
[52] U.S. Cl. .................................. 606/10; 606/11; 606/13; 606/2; 433/29; 433/215; 219/121.6; 219/121.61; 216/94
[58] Field of Search .................................. 606/2, 4–6, 9, 606/10–12, 13, 27, 28, 32, 34, 41; 505/474, 412; 427/596, 58; 65/61; 219/121.6, 121.61, 200, 209, 220; 433/29, 215; 216/65, 67, 94

[56] References Cited

U.S. PATENT DOCUMENTS

| | | |
|---|---|---|
| 4,907,586 | 3/1990 | Bille et al. . |
| 5,312,396 | 5/1994 | Feld et al. .................................. 606/11 |
| 5,342,198 | 8/1994 | Vassiliadis et al. . |
| 5,411,502 | 5/1995 | Zair ........................................... 606/10 |
| 5,613,965 | 3/1997 | Muller ........................................ 606/5 |
| 5,720,894 | 2/1998 | Neev et al. . |

OTHER PUBLICATIONS

Raimund Hibst, and Ulrich Keller, "Experimental Studies of the Application of the Er:YAG Laser on Dental Hard Substances: I. Measurement of the Ablation Rate", Lasers in Surgery and Medicine 9:338–344 (1989).

Ulrich Keller, and Raimund Hibst, "Experimental Studies of the Application of the Er:YAG Laser on Dental Hard Substances: II. Light Microscopic and SEM Investigations", Lasers in Surgery and Medicine 9:345–351 (1989).

J. T. Walsh, Jr., T.J. Flotte, R.R. Anderston and T.F. Deutsch, "Pulsed $CO_2$ Laser Tissue Ablation: Effect of Tissue Type and Pulse Duration on Tehrmal Damage", Lasers in Surgery and Medicine 8:108–118 (1988).

J. T. Walsh, Jr., T. J. Flotte, and T. F. Deutsch, "Er:YAG Laser Ablation of Tissue: Effect of Pulse Duration and Tissue Type on Thermal Damage", Lasers in Surgery and Medicine 9:314–326 (1989).

J. T. Walsh, Jr., and T. F. Deutsch, "Er: YAG Laser Ablation of Tissue: Measurement of Ablation Rates", Lasers in Surgery and Medicine 9:327–337 (1989).

J. Neev, K. Pham, J. P. Lee, J. M. White, "Dentin Ablation with Three Infrared Lasers", Beckman Laser Institute and Medical Clinic Irvine, supported by grants; Navy Grant #N00014–90–0–0029 DOE #DE–FG0391ER61227, Aug. 9, 1994, 15 pages.

J. Neev, A. Stabholtz, L.L. Liaw, M. Torabinejac, J. T. Fujishige, P.D. Ho, and M. W. Berns, "Scanning Electron Microscopy and Thermal Characteristics of Dentin Ablation by a Short–Pulse XeCI Excimer Laser", Lasers in Surgery and Medicine 13:353–362 (1993).

(List continued on next page.)

*Primary Examiner*—Michael Peffley
*Assistant Examiner*—Bryan K. Yarnell
*Attorney, Agent, or Firm*—Christie, Parker & Hale, LLP

[57] ABSTRACT

A method and apparatus is disclosed for fast precise material processing and modification which minimizes collateral damage. Utilizing optimized, pulsed electromagnetic energy parameters leads to an interaction regime which minimizes residual energy deposition. Advantageously, removal of cumulative pulse train residual energy is further maximized through the rapid progression of the ablation front which move faster than the thermal energy diffusion front, thus ensuring substantial removal of residual energy to further minimize collateral thermal damage.

7 Claims, 38 Drawing Sheets

OTHER PUBLICATIONS

J. Neev, D. V. Raney, W. E. Whalen, J.T. Fujishige, P.D. Ho, J. V. McGrann, and M.W. Berns. "Selectivity and Efficiency in the Ablation of Hard Dental Tissues with ArF Pulsed Excimer Laser", Beckman Laser Institute and Medical Clinic, (University of California, Irvine) 22 pages.

J. Neev, D.V. Raney, W. E. Whalen, J.T. Fujishige, P.D. Ho, J.V. McGrann and M.W. Berns, "Dentin Ablation with Two Excimer Lasers: A Comparative Study of Physical Characteristics", Lasers in the Life Sciences, 5(1–2), 1992, pp. 129–153.

J. Neev, D. V. Raney, W. E. Whalen, J.T. Fujishige, P. D. Ho, J. V. McGrann, and M. W. Berns, Reprinted from "Proceedings of Laser–Tissue Interaction II", SPIE—The International Society for Optical Engineering, Jan. 21–23, 1991, pp. 162–172.

J. T. Walsh, and D. Ashley Hill, "Erbium Laser Ablation of Bone: Effect of Water Content" SPIE vol. 1427 Laser–Tissue Interaction II;(1991), pp. 27–33.

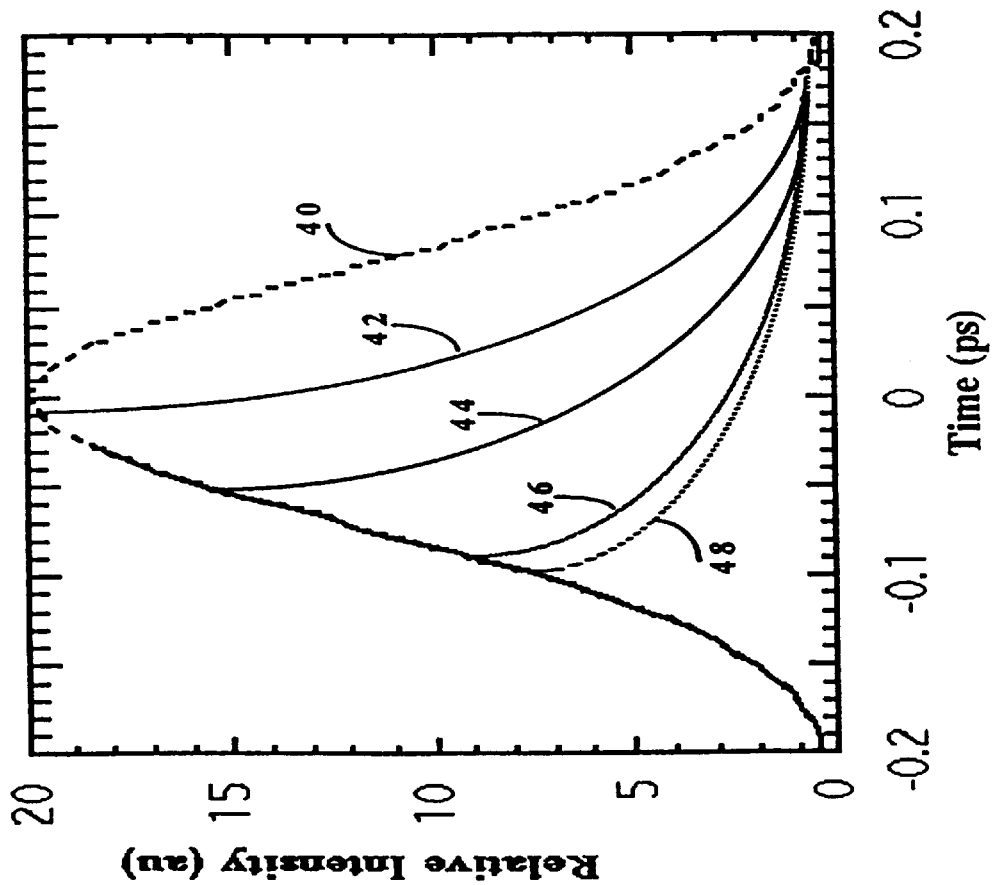

METHOD AND APPARATUS FOR HIGH PRECISION VARIABLE RATE MATERIAL REMOVAL AND MODIFICATION

RELATED APPLICATIONS

This patent application claims the benefit of the filing date of U.S. Provisional Patent Application Serial No. 60/050,416, filed on Jun. 4, 1997 and entitled "METHOD AND APPARATUS FOR A VARIABLE-RATE THREE DIMENSIONAL MATERIAL PROCESSING AND MODIFICATION, the contents of which are hereby incorporated by reference.

FIELD OF THE INVENTION

The present invention is generally related to the field of pulsed electromagnetic energy source systems suitable for material and biological tissue modification processing and removal and is more particularly related to a material removal and modification method and apparatus in which pulsed electromagnetic sources of high ablation-to-deposition depth ratios are operable at pulse repetition rates ranging up to approximately several hundreds of thousands of pulses per second so as to efficiently and precisely remove substantial material volumes while substantially eliminating collateral damage.

BACKGROUND OF THE INVENTION

The past three decades have brought increased interest in the use of lasers in material processing applications. Early procedures for material processing and cutting involved optical drilling using continuous wave or relatively long pulse (e.g., 50 to 350 $\mu$s) lasers such as C02, ruby and ND:YAG (Neodymium doped Yttrium Aluminum Garnet). These systems, however, required relatively high radiant exposure and resulted in significant alterations to surrounding tissue. As a consequence, lasers could become an effective cutting tool only in areas which did not require high degree of precision or control.

Optical drilling with ER:YAG (Erbium doped YAG) lasers yielded encouraging results in the late 1980s, and has demonstrated its capability to perform as an efficient drill while incurring only relatively low levels of collateral damage to surrounding tissue, provided that no more than one to three pulses per second were applied to the target material. The success of ER:YAG systems, operating in the microsecond pulse duration regime and minimizing thermal damage has also been observed in several areas of applications in material processing and medicine, and can be attributed to the high absorption coefficient of these materials at the particular wavelengths characteristic of the Er:YAG system (2900 nm), when used in combination with the relatively short pulse durations and at low pulse repetition rates.

Laser systems adapted to hard tissue processing, such as dentin and enamel removal in dental applications are disclosed in: 1. Hibst R, Kelly U. Experimental studies of the application of the Er:YAG laser on dental hard substances: I. Measurement of the Ablation Rate. *Laser Surgery and Medicine* 1989, 9:352–7; and, 2. Keller U, Hibst R. Experimental studies of the application of the Er:YAG laser on dental hard substances: II. Light microscopy and SEM investigations. *Lasers in Surgery and Medicine* 1989; 9:345–351.)

Both pulsed CO2 and Er:YAG are disclosed in: Walsh, J. T., Flotte, T. J., Anderson, R. R., Deutsch, T. F., "Pulsed $CO_2$ Laser Tissue Ablation: Effect of Tissue Type and Pulse Duration on Thermal Damage, "*Lasers in Surgery and Medicine*, Vol. 8, pp.108–118, 1988; Walsh, J. T., Flotte, T. J., Deutsch, T. F., "Er:YAG Laser Ablation of Tissue: Effect of Pulse Duration and Tissue Type on Thermal Damage, "*Lasers in Surgery and Medicine*, Vol. 9, No. 4, pp. 314, 1989; and Walsh, J. T., Deutsch, T. F., "Er:YAG Laser Ablation of Tissue: Measurement of Ablation Rates, "*Lasers in Surgery and Medicine*, Vol. 9 No. 4, pp. 327, 1989.

A Ho:YSGG laser system is disclosed in Joseph Neev, Kevin Pham, Jon P. Lee, Joel M. White, "Dentin Ablation with Three Infrared Lasers," *Lasers in Surgery and Medicine*, 18:121–128 (1996).

The laser systems disclosed (Er:YSGG, HO:YSGG, and Pulsed CO2) all operate in the IR region of the electromagnetic spectrum and are pulsed in two different regimes: about 250 microsecond pulse durations for the ER:YSGG and HO:YSGG lasers, and about 150 microsecond pulse durations for the CO2 system.

While the disclosed removal rate is in the range of approximately tens of micrometers per pulse, the disclosed laser systems exhibit wavelength dependent absorption and result in high removal rates by operating at pulse energies in excess of 30 millijoules per pulse and often on the order of a few hundreds of $\mu$J per pulse. Enhancing material removal by increasing laser power is, however, accompanied by increased photothermal and photomechanical effects which causes collateral damage in adjacent material. In addition, increasing power leads to plasma de coupling of the beam, e.g., incident laser energy is wasted in heating the ambient in front of the target. High intensity pulses additionally cause very loud acoustic snaps, when the laser pulse interacts with tissue. These snaps or pops include a large high frequency component which is very objectionable to a user or, in the case of a medical application, to a patient. In addition to the psychological impact of such noise, these high frequency snaps are able to cause hearing loss in clinicians when repeated over a period of time.

U.S. Pat. No. 5,342,198, to Vassiliadis, et al. discloses an ER:YAG IR laser system suitable for the removal of dentin in dental applications. The laser produces a pulsed output having a beam with a pulse duration in the range of several tens of picoseconds to about several milliseconds. Although disclosed as being efficient in the removal of dentin and dental enamel, the mechanism by which material removal is effected is not understood. Significantly, however, the only laser systems disclosed as suitable for the process are those which operate at wavelengths (1.5 to 3.5 microns) that have proven to be generally effective for enamel interaction. Thus, the absorption characteristics of the material target are of primary concern to the removal rate. In addition, high energy levels are required to remove enamel and dentin, leading to the problem of thermal damage and acoustic noise.

Additional possibilities for the application of lasers to the field of dentistry in particular, and to hard tissue ablation in general, have been proposed by the use of excimer lasers that emit high intensity pulses of ultraviolet (UV) light.

Several such pulsed UV excimer laser systems, typically with pulse durations in the approximately 1 to 125 nanosecond range are disclosed in:

1. Neev J, Stabholz A., Liaw L. L, Torabinejad M, Fujishige J. T., Ho P. H, Berns M. W., "Scanning Electron Microscopy and Thermal characteristics of Dentin ablated by a short-pulse XeCl Laser", Lasers in Surgery and Medicine;

2. Neev J, Liaw L, Raney D, Fujishige J, Ho P, Berns M. Selectivity and efficiency in the ablation of hard Dental tissue with ArF pulsed excimer lasers. Lasers Surgery and Medicine 1991; 11:499–510;

3. Neev J, Raney D, Whalen W, Fujishige J, Ho P, McGrann J, Berns M. Ablation of hard dental tissue with 193 nm pulsed laser radiation: A photophysical study. Spie proceedings, January 1991; and 4. Neev J, Raney D, Whalen W, Fujishige J, Ho P, McGrann J, Berns M. Dentin ablation with two excimer lasers: A comparative study of physical characteristics. Lasers Life Sci 1992; 4(3):1–25. Both the short wavelengths and nanosecond range pulse durations used by excimer lasers contribute to define a different regime of laser-tissue-interaction. Short wavelength ultraviolet photons are energetic enough to directly break chemical bonds in organic molecules. As a consequence, UV excimer lasers can often vaporize a material target with minimal thermal energy transfer to adjacent tissue. The resultant gas (the vaporization product) is ejected away from the target surface, leaving the target relatively free from melt, recast, or other evidence of thermal damage.

Another important characteristic of UV excimer lasers is that materials which are transparent to light in the visible or near infra-red portions of the electromagnetic spectrum often begin to exhibit strong absorption in the UV region of the spectrum. It is well established that the stronger a materials absorption at a particular wavelength, the shallower the penetration achieved by a laser pulse having that wavelength. Thus, in many types of materials, a pulse typically only penetrates to a depth in the range of from about 10 to about 100 micrometers. By simply counting pulses, great precision can be achieved in defining removal depths. In addition, organic tissue is strongly absorbent in the UV wavelengths (193 nm for ArF, for example) therefore allowing the laser-tissue interaction region to be controlled with great precision.

Notwithstanding the relatively damage free material removal characteristics of UV excimer lasers, these systems suffer from several disadvantages which limit their applicability to biological tissue processing. The reports of damage free tissue removal result from evaluations performed on single pulses, or on pulses with a very low repetition rate (typically about 1 to 10 Hertz). Because of the low volumetric removal per pulse of excimer systems (material removed per unit time is poor), efficient material removal can only be accomplished by high pulse repetition rates. However, when the pulse repetition rate exceeds about 3 to 5 Hertz, considerable thermal and mechanical collateral damage is observed. While UV photons are sufficiently energetic to directly break chemical bonds, they are also sufficiently energetic to promote mutagenic effects in tissue irradiated at UV wavelengths, raising concerns about the long term safety and health of a system operator. The scattered light produced by excimer lasers also presents a significant threat to the clinician and/or the patient. Even low intensity scattered radiation, with wavelengths below 300 nanometers, is able to interact with the ambient environment to produce atomic oxygen and other free radicals. These can, in turn, react with the lens and cornea of the eye, producing cataracts, and produce burns on the skin equivalent to sun burns. As a consequence, excimer laser systems have been found to be most suitable for inorganic material processing applications, such as thin coating patterning or dielectric or semiconductor material etching.

In addition, the operational parameters of excimer laser systems are such that material removal remains a wavelength and beam energy dependent process (although weakly dependent on wavelength). Even when pulsed in the tens of nanoseconds pulse duration regime, excimer lasers are configured to deliver energy in the range of from about 10 to about 1000 millijoules per pulse. At the higher energies, excimer lasers suffer from the same problems caused by plasma decoupling and pulse to pulse interaction as IR lasers. Additionally, as pulse energy increases, so too does the intensity of the associated acoustic snap.

Neev et al. (University of California Case No. 95-313-1) U.S. patent application Ser. No. 08/584,522 described a Selective material removal processing Ultra Short Pulse Lasers (USPL) system in combination with a feedback system and with higher pulse repetition rates. This invention is directed to a system for efficient biological tissue removal using ultra short pulses. Such pulse durations are shorter than the characteristics electron-phonon energy transfer time, thus minimizing collateral thermal damage. The method also requires that plasma is formed and decayed so that a thin layer portion of the material is removed. The plasma formation step is then repeated at a pulse repetition rate greater than 10 pulses per second until a sufficient depth of material has been removed with little transfer of thermal or mechanical energy into the remaining material due to the shortness of the pulse duration. The preferred wavelength for that invention is in the range of 200–2500 nm. The laser specified in that patent application is a Chirped Pulse Amplifier (CPA) Solid-state laser.

That patent further specified that the laser system is comprised of a feedback means for analyzing material characteristics in response to interaction between the laser pulses. The envisioned feedback means comprises a spectrograph to evaluate the plasma formed by each pulse. The feedback means is operatively coupled to the laser. The laser operatively responds to the control signal such that the laser ceases operation upon receipt of the control signal. The feedback means also comprises an optical tomograph which optically evaluates the amount of target material removed by each pulse.

This invention should work well in many applications. Unfortunately, the equipment for the ultrashort pulse duration is very expensive (currently, over $100,000 and often two or three times that amount) and still requires many components and careful maintenance. The systems are also very large and delicate and require large volume for storage and expert maintenance at this stage of the technology. Also the interaction is not very selective nor highly sensitive to the targeted material type but rather ablate most materials. This, in turn, effects some risk of over ablating or removal of unintended structures. The highly interactive nature of the ultrashort pulse process possess additional problems to attempts to deliver the ultrashort pulse beam to the target. Most optical fibers as well as mirror and lenses could easily be damaged if ablation threshold is exceeded (either through narrowing of the beam spot size, an increase in pulse energy, or compression of the pulse duration). Thus ultrashort pulses are hard to deliver through most conventional delivery systems.

An additional problem is that ultrashort pulse lasers are currently achieved principally in the near IR region of the electromagnetic spectrum. This is a highly transparent region for most biotissue material. Consequently, some portion of the radiation propagates linearly into the material and is not confined to the surface. This additional energy propagating into the target may then encounter more absorbing structures (for example the blood vessels in the retina) and will then result in a secondary—unintended—ablative interaction, posing risk to the patients or to the material being processed.

U.S. Pat. No. 4,907,586 issued to Bille and Brown for "METHOD FOR RESHAPING THE EYE", disclosed a method for modifying tissue with a quasi-continuous laser beam to change the optical properties of the eye which comprises controllably setting the volumetric power density of the beam and selecting a desired wavelength for the beam. Tissue modification is accomplished by focusing the beam at a preselected start point in the tissue and moving the beam's focal point in a predetermined manner relative to the start point throughout a specified volume of the tissue or along a specified path in the tissue.

More particularly, the method describes a sequence of uninterrupted emissions of at least one thousand pulses lasting for at least one second. The pulses were specified lasting approximately one picosecond (1 ps) in duration and of less than 30 micro joules (30 $\mu$J).

The invention disclosed in U.S. Pat. No. 4,907,586 should work well for reshaping the eye, but is confined to the region of 1 ps and thus also involves the generation of ultrashort pulses and their relative low thermal and mechanical deposition of energy during the single pulse interaction. This device thus requires the use of expensive ultrashort pulses with all the specified limitations mentioned above. In addition, this invention is limited to relatively low energies of 30 $\mu$J, which require a very tightly focused beam to affect tissue ablation. The invention will thus not work well for larger areas or for high volume removal rates, which are required in many applications, e.g., dentistry, surgery, etc. This invention is also limited with regards to its ability to deliver pulses through optical fibers, hollow waveguides or conventional optics since the very shorted pulses of 1 ps are also very reactive and will interact with most material used as deliver media. Consequently, specialty optics has to be used and conventional lenses and mirrors as well as optical fiber and conventional hollow waveguides cannot be used.

In the present invention, the inventor has recognized that a much wider range of pulse durations of up to approximately several hundred microseconds will allow the thermal diffusion to remain confined to within a distance of only a few micrometer of the ablated crater. Thus, the present invention is concerned with pulses up to several milliseconds long. With a combination of short pulse to pulse separation and with new requirement on both the number and the rate of the incident sequential pulses, the present invention allows large volume removal or volume processing with substantially little damage to surrounding regions of the target.

The present invention thus allows the use of pulse laser systems that are substantially less expensive and in many instances safer and more efficient than those described by other inventions, while achieving unprecedented volume removal rate, high precision, high efficiency and minimal thermal or mechanical collateral damage.

SUMMARY OF THE INVENTION

The present invention specifically addresses and alleviates the above mentioned deficiencies associated with the prior art. More particularly, the present invention comprises a method for ablating a material. The method for ablating a material comprises the steps of directing a pulse of energy at the material and so as to permanently modify a quantity of the material. The pulse is specifically configured to increase a ratio of the quantity of the material which is ablated thereby with respect to the quantity of the material which is permanently modified thereby.

Ablating the material with an energy pulse configured specifically configured to increase the ratio of the quantity of the material which is ablated thereby with respect to the quantity of the material which is permanently modified thereby minimizes undesirable permanent modification of the material.

Preferably, at least one characteristic of the material to be ablated is first determined and then a pulse of the directed energy is defined which increases the ratio of the quantity of the material which is ablated thereby with respect to the quantity of the material which is permanently modified thereby. Thus, the characteristic(s) of the material at least particularly define the pulse which is used to ablate the material. For example, the characteristics of the material which may be determined may comprise thermal conductivity, effective electromagnetic energy depth, material energy gapped between valence and conductivity bands, material density or material strength, taken either alone or in combination with one another.

Although the directed energy pulse is described herein as being comprised of laser radiation, those skilled in the art will appreciate that various different types of direct energy, accelerated electrons, accelerated ions, various forms of electromagnetic energy, etc., are likewise suitable. The directed energy may also comprise light from either an LED, a fluorescent lamp, or an incandescent lamp, taken alone or in combination with one another, the directed energy pulse may comprise either coherent or incoherent electromagnetic radiation or any combination thereof.

The characteristic(s) of the material to be ablated may be determined in a variety of different ways, such as by directly sensing the characteristic(s) of the material, by looking up the characteristic(s) of the material in a reference, or by ablating the material with a pulse of the direct energy, determining the approximate quantity of the material ablated and also determines the approximate quantity of the material permanently modified. Thus, one way of determining the desired characteristic(s) of the material to be ablated is by first ablating a quantity of the material and then observing how much of the material is actually ablated versus how much of the material is permanently modified during the ablation process. This determination facilitates adjustment defining the pulse in a desired manner so as to minimize residual heat, thereby minimizing the quantity of the material permanently modified subsequent pulses.

According to a further aspect of the present invention, a plurality of pulses of energy are directed at the material so as to ablate a quantity of the material and so as to permanently modify a quantity of the material. The pulses have a sufficient pulse rate so as to increase the ratio of the quantity of the material which ablated thereby with respect to the quantity of the material which is permanently modified thereby. In this manner, the material is ablated with a plurality of directed energy pulses having a sufficient pulse rate as to minimize undesirable permanent modification of the material.

In a manner similar to that utilized for a single pulse, at least one characteristics of the material to be ablated is determined when utilizing a plurality of pulses. The characteristic(s) of the material to be ablated are then utilized to define the pulse rate of the directed energy so as to again increase the ratio of the quantity of the material which is ablated thereby with respect to the quantity of the material which is permanently modified thereby.

Of course, both a pulse of the directed energy and a pulse rate of the direct energy may be defined by the characteristic (s) of the material to be ablated such that the combination of both the specifically configured pulse and the pulse rate cooperate to increase the ratio of the quantity of the material which will be ablated by the plurality of pulses with respect to the quantity of the material which will be permanently modified thereby.

Thus, according to the present invention, a material is ablated by utilizing a laser. The laser is specifically configured for use with the material so as to cause a substantial quantity of the energy absorbed by the material to subsequently be removed therefrom with the material ejected during ablation. Removing a substantial amount of the energy absorbed by the material minimizes residual energy deposition while ablating, so as to mitigate collateral thermal damage to the material. Ablation of the material is preferably formed at a velocity greater than the thermal energy diffusion through the material so as to remove residual energy from the material.

The material is preferably ablated using a laser having a sufficiently high pulse repetition rate to cause a substantial amount of the energy absorbed by the material to subsequently be removed therefrom with the ejected material. The characteristic(s) of a laser beam pulse are based upon properties of the material so as to provide a depth of the material removed by the pulse which is approximately equal to an electromagnetic deposition depth of the material.

Optionally, the material is ablated utilizing a laser wherein characteristic(s) of the laser beam pulse are based upon properties of the material so as to provide a plasma. The plasma is generated by either multiphoton ionization or thermal ionization. The plasma effects an electromagnetic energy deposition depth which is approximate to a depth of the material removed by the pulse.

Optionally, doping agents are added to the material being ablated. The doping agents cause the laser to provide an electromagnetic energy deposition depth which is approximately equal to the depth of the material removed by the laser.

More particularly, according to the methodology of the present invention high precision, highly controllable, variable rate, material removal is provided by a pulsed electromagnetic radiation beam. The interaction between the pulse electromagnetic radiation beam and the material effects a material removal depth substantially equal to the energy deposition depth within the target material.

The method comprises the steps of providing an electromagnetic radiation source capable of generating an output beam comprised of a sequence of electromagnetic pulses, each pulse having a pulse duration in the range of approximately 1 femtosecond to approximately 10 milliseconds.

The sources operated and beam parameters of the electromagnetic radiation output beam are manipulated so that the electromagnetic pulse's power densities within the region targeted for energy deposition is in the range of approximately $10^7$ W/cm$^3$ to approximately $10^{18}$ W/cm$^3$ and is larger than the power density threshold for material ablation.

Thus, the material is ablated with electromagnetic energy from the source so that a substantial portion of the deposited electromagnetic energy is removed from the target material with an ejected portion of the material.

Ablation of the material is repeated at a pulse repetition rate greater than approximately 0.1 pulses per second so that a substantial portion of the cumulative residual thermal energy left in the material by the electromagnetic energy is removed by the cumulative ablation. The pulse repetition rate is preferably smaller than approximately 500,000 pulses per second. This process continues until a sufficient depth of the material has been removed.

The electromagnetic beam's energy deposition depth within the material defines a volume so that the power density within the volume is greater than the threshold power density for material ablation.

The pulsed electromagnetic radiation source preferably produces an output beam having a wave length in the range of approximately 10 nanometers to approximately 50 micrometers.

Each pulse of the pulsed force preferably has an energy in the range of approximately 0.001 microjoule to approximately 50 Joule. The output beam preferably has a diameter at the target material such that the target material experiences an energy fluence in the range of approximately 0.001 Joule per square centimeter to approximately 100 Joule per square centimeter.

The pulsed beam preferably exhibits a material removal rate in the range of approximately 0.01 micrometers to approximately 100,000 micrometers per pulse. The removal rate is preferably substantially constant.

According to a further aspect of the present invention, precise, highly controlled, variable rate material removal is provided by a pulsed electromagnetic radiation beam. A source capable of generating an output beam comprised of a sequence of electromagnetic pulses is provided. Preferably, each electromagnetic pulse has a pulsed duration in the range of approximately 1 femtosecond to approximately 10 milliseconds.

The source is operated and the beam parameters manipulated so that the electromagnetic pulse's power densities within the region targeted for energy deposition is in the range of approximately $10^8$ W/cm$^3$ to approximately $10^{18}$ W/cm$^3$ and is larger than the power density threshold for plasma formation.

The formed plasma is allowed to decay such that a layer of the material is removed. The removed layer of material carries with it a substantial portion of the deposited electromagnetic energy from the target regions.

The pulse source is operated so that once a critical electron density is reached within the formed plasma, the formed plasma substantially presents excess pulse energy form directly reaching the material and so that the formed plasma prevents excess pulse energy from substantially increasing the electromagnetic energy deposition depth and the depth of the material removed by ablation.

The pulse source is operated at a pulse repetition rate greater than approximately 0.1 pulses per second and less than approximately 500,000 pulses per second until a sufficient depth of material has been removed.

According to a preferred embodiment of the present invention, the laser beam defines a spot on the target characterized in that fluence within the beam spot is greater than the threshold fluence for plasma formation.

The plasma formation substantially prevents deep energy deposition in the material so that a substantial portion of the electromagnetic energy deposited in the material is removed with the material ejected.

The pulsed electromagnetic energy source preferably produces an output beam having a wavelength in the range of from approximately 10 nanometers to approximately 15 micrometers. Each pulse of the pulsed energy source preferably has an energy in the range of approximately 0.001 microjoule to approximately 100 Joule. The output beam preferably has a diameter at the material target such that the material experiences an energy fluence in the range of approximately 0.001 to approximately 100 Joule per square centimeter.

The pulse laser beam preferably exhibits a material removal rate in the range of approximately 0.01 to approximately 10 micrometers per pulse. The removal rate is preferably substantially constant without regard to material chromophore, material hardness or material state.

Optionally, the target material is substantially transparent to the linear propagation of the electromagnetic pulses and the beam is focused below the surface of the target material so that the beam intensity exceeds the plasma formation threshold only at approximately the point of focus and the material is substantially removed at that desired point below the surface. In this manner, material can be ablated in a manner which forms caverns or hollow volumes within the material. Thus, cavities having various different desired shapes may be so formed. This may be accomplished using either a single pulse, or a plurality of pulses, as desired.

Alternatively, the method for controlled variable rate material removal by a pulsed electromagnetic radiation beam comprises providing a source capable of generating an output beam comprised of a sequence of electromagnetic pulses, wherein each electromagnetic pulse has a pulse duration in the range of about 1 femtosecond to about 10 milliseconds and also comprises operating the pulse source and manipulating the beam parameters so that the electromagnetic pulses' peak intensity is in the range of approximately $10$ W/cm$^2$ to approximately $10^{16}$ W/cm$_2$ and adding to the target material absorption or scattering centers, defects, highly absorbing or highly scattering components, so that the electromagnetic radiation penetration depth is reduced and/or plasma is formed.

Preferably, the electromagnetic energies absorbed by the material to complete the material disintegration and explosive ejection of the targeted material deposition volume, so that substantially most of the deposited energy is removed from the target material with the ejected portion of the material. The pulse source is preferably operated at a pulse repetition rate greater than approximately 0.1 pulses per second smaller than approximately 500,000 pulses per second until a sufficient depth of material has been removed.

Further, according to the preferred embodiment of the present invention, plasma is formed and expanded, substantially preventing excess pulse energy from directly reaching the material and so that excess pulse energy does not substantially effect ablation depth. The plasma is preferably allowed to decay such that a layer of the material is removed and substantially most of the material radiation pulse energy deposited in the material is removed with the layer. The source is operated at a pulse repetition rate greater than approximately 0.1 pulses per second and less than approximately 500,000 pulses per second until a sufficient depth of material has been removed.

In a further alternative method for controlled, variable rate material modification, a pulsed electromagnetic radiation beam is provided by providing a source capable of generating and output beam comprised of a sequence of electromagnetic pulses, each electromagnetic pulse having a pulse duration in the range of approximately 1 femtosecond to approximately 100 milliseconds. The pulse source is operated and the beam parameter is manipulated so that the deposited volumetric power density within the targeted material is greater than the threshold power density for material modification, such that control of the power density is achieved by varying either one or more of the following parameters: the beam spot size at the target location, the duration of the electromagnetic pulse emissions, the energy of the electromagnetic pulse emissions, the wavelength of the electromagnetic pulse emissions, or by spatially and temporally varying the absorption and/or scattering characteristics of the material at the target region. The interaction energy transients caused by the electromagnetic radiation pulse are allowed to substantially decay such that material modification is effected. Such material modification preferably includes one or more of the of the following alterations: Chemical and physical changes, changes to visco elastic properties, changes to optical or thermal properties, chemical and physical breakdown, disintegration, ablation, melting, or vaporization.

The pulse source is preferably operated at a pulse repetition rate greater than approximately 0.1 pulses per second until a sufficient volume of the material has been modified.

The target material is preferably substantially transparent to linear beam propagation and the threshold volumetric power density is achieved at a desired target location below the surface and within the material volume. Again, scattering and/or absorption centers, defects, or highly absorbing components are added to the target material with spatial and/or temporal selectivity to specific, predetermined locations within the target material.

The pulse beam preferably exhibits a material modification rate in the range of approximately $0.01^3$ cubic micrometers per pulse to approximately $100,000^3$ cubic micrometers per pulse. The material modification rate is preferably substantially constant, depending substantially on the volumetric power density threshold characteristics of the material and on the target-beam characteristics thereof.

Thus, a method and apparatus is disclosed for fast, precise and damage-free material processing and modification using a high pulse repetition rate electromagnetic energy source. The pulsed interaction uses a parameter regime which minimizes residual energy deposition while ablating. Advantageously, removal of cumulative pulse train residual energy is maximized through the rapid progression of the ablation front which moves faster than the thermal energy diffusion. Removal of residual energy thus minimizes collateral thermal and mechanical damage in material processing and also minimizes pain and suffering during surgical procedures. The operating parameters for the system are achieved through the selection of material properties and beam characteristics which ensure localization of incoming electromagnetic energy into a deposition zone comparable in its depth and lateral dimensions to the depth and lateral dimensions of the volume of ablated material. The disclosed method identifies either high linear absorption or plasma-mediated interactions, or a combination of the two, as potential avenues for fulfilling the deposition depth—ablation depth near—parity requirements which enable high pulse repetition rate operation and thus ensure rapid material removal. The disclosed apparatus then describes a variable repetition rate system which allows highly adjustable material removal rates ranging from very rapid to very slow. A set of possible energy delivery and collection systems is then disclosed which allow highly accurate delivery, monitoring, feedback, control, and automation for extreme precision and unprecedented accuracy that can be offered simultaneously with the rapid rate of operation. Finally, a method and apparatus are disclosed for fast, efficient, precise and damage-free material modification, utilizing the threshold nature of plasma-mediated interaction and/or selectively induced, high absorption regions. Making use of the same apparatus with the option to spatially and/or temporally control the addition of "doping agents", to induce selective power deposition, precise and highly localized material removal and/or modification can be induced at any desired location within the three-dimensional space of the target region while substantially sparing adjacent regions of the target material from any collateral damage.

Further, a method for high precision, highly controllable, variable rate, material removal by a continuously emitting, continuous wave (CW) beam of electromagnetic radiation is provided. The interaction between the electromagnetic beam and the material is such that a material removal depth is approximately equal to an energy deposition depth within the target material. The method comprises the steps of: providing a source capable of generating an output beam comprised of continuously emitted electromagnetic radiation; and redistributing the beam in time and space to form at least one modified beam. This is accomplished by repeatedly selecting a portion of the beam in time and redirecting that portion of the beam so as to define a series of pulses. In this manner, a plurality of time sequential segments of the beam are redirected, preferably through an optical fiber. Thus, a short segment of the CW beam, enough to provide the desired pulse, is diverted from the remainder of the beam. Other portions of the beam may similarly be redirected such that the entire beam is utilized.

In effect, the beam is time sliced, such that for a given duration, a portion of the beam is directed to one optical fiber, and then for another period of time the optical beam is directed to another optical fiber. This process is repeated for a desired number of optical fibers (optimally until the entire beam is utilized) and after the beam has been directed to each of the optical fibers, the process repeats. In this manner, the beam is sequentially directed from one optical fiber to another, so as to define the desired number of separated pulsed beams. Each of the optical fibers directs the beam to a desired location where material ablation is to occur. Generally, each portion of the beam will be directed such that it is incident upon adjacent (optionally overlapping) areas of the material to be ablated such that the different portions of the beam cooperate so as to effect material ablation in an efficient and effective manner which minimizes undesirable modification of adjacent material due to overheating.

Thus, the beam is redirected so that either a single or multiple beams are formed and such that their energy distribution at any given location on the target material forms a sequence of electromagnetic pulses. Each electromagnetic pulse preferably has a duration between approximately 1 femtosecond and approximately 10 milliseconds.

Thus, the beam is modified such that the original beam is re-configured into a new single or multiple beams. In this manner, the energy of the original beam is utilized after having been redistributed in both time and space.

The source of electromagnetic energy is operated and the beam parameters are manipulated so that the electromagnetic pulse's power densities within the region targeted for modification are between approximately $10^4$ W/cm$^3$ and approximately $10^{18}$ W/cm$^3$ and are larger than the power density threshold for material ablation. The electromagnetic energy absorbed by the material is allowed to complete the material ablation process, so that substantially most of the deposited electromagnetic energy is removed from the target material with an ejected portion of the material, as discussed in detail above.

Such electromagnetic energy absorption is repeated, as desired so that ablation and energy removal occurs at a pulse repetition rate greater than 0.1 pulses per second, such that substantially most of the cumulative residual thermal energy left in the material by a pulse train is removed by the cumulative ablation. Thus, ablation is performed at a pulse repetition rate less than approximately 500,000 pulses per second until a sufficient depth of material has been removed with substantially no transfer of thermal or mechanical energy into the main material and substantially no collateral damage thereto.

The step of redistributing the beam preferably comprises deflecting sequential portions of the beam and redirecting them to a distinguished, separate locations upon the target material, so that the net affect at each location is that of a sequence of pulses of a specified or desired duration and a specified or desired pulse repetition rate.

In this manner, the switching device redirects sequential portions of the beam to separate locations so that the net affect at each location is that of a sequence of pulses of specific duration and the step of redistributing the beam comprises directing the beam to a device selected from a device such as a rapidly rotating mirror or other optical means for directing electromagnetic radiation, a Kerr cell, a Pockels cell, and acousto-optic modulator, an electro-optic modulator, or any other electro-optical, electrical, magnetic, or electromagnetic means for redirecting light.

The switching device sequentially redirects the original beam energy into at least one optical guiding device such as an optical fiber or a hollow wave guide light conductors. The optical guiding device then redistributes the beam to separate locations on the target material.

Preferably, the output of the single or multiple optical fibers or hollow wave guides is performed so as to focus the energy to a spot size such that the power density within the volume target is for material removal for modification is greater than the threshold power density for material ablation or the desired modification.

The step of redistributing the beam preferably comprises redirecting the original beam energy into a single or multiple lenses or other optical focusing devices and then allowing the newly redistributing beams to propagate to separate locations on the target material.

The pulse electromagnetic radiation source produces an output beam having a wavelength in the range of 10 nanometers to 50 micrometers.

The continuously emitting beam source preferably has an average power in the range of approximately 0.0001 Watt to approximately 500 KWatts. The output beam preferably has a diameter at the target material such that the target material experiences a power per unit area in the range of approximately 1 Watt per square centimeter to approximately $10^{14}$ Watts per square centimeter.

The pulse beam is preferably configured to provide a material removal rate in the range of approximately 0.01 micrometer to approximately 10,000 micrometers per pulse. The material removal rate per pulse is preferably substantially constant.

Each of the redistributed beams comprises a sequence of electromagnetic pulses, each pulse preferably having a pulse duration in the range of approximately 1 femtosecond to approximately 10 milliseconds and has a pulse repetition rate greater than approximately 0.1 pulses per second and less than approximately 100,000 pulses per second.

The redistributed beam preferably comprise a sequence of electromagnetic pulses which is directed to a target location adjacent one another. In this manner, the beams cooperate with one another so as to remove at least some thermal energy generated by preceding pulses and these adjacent beams.

The step of redistributing the beam preferably further comprises changing the beam wavelength via a device such as an optical parametric oscillator, and optical parametric amplifier, or a non-linear frequency converting crystal such as KTP or KDP. In this manner, the frequency of the beam is doubled, tripled, quadrupled, etc., as desired.

According to the preferred embodiment of the present invention, a device for high precision, highly controllable, variable rate, material removal by a continuously emitting, continuous wave (CW) beam of electromagnetic radiation wherein the interaction between the electromagnet beam and the material being characterized by a material removal depth which is substantially comparable to the energy deposition depth within the target material. The device preferably comprises an energy radiating device for providing a continuously emitted electromagnetic energy beam and a first controller for redistributing the energy beam into at least redistributed beam which is redistributed in space and time, i.e., time sliced.

A controller redirects the redistributed beams so that the energy distribution at any given location on the target material forms a sequence of electromagnetic pulses, each electromagnetic pulse having a pulse duration in the range of approximately 1 femtosecond to approximately 10 milliseconds. The device and its controllers are preferably operated such that the output electromagnetic power densities within the region targeted for modification is in the range of approximately $10^4$ W/cm$^3$ to about $10^{18}$ W/cm$^3$ and is larger than the power density threshold for material ablation. The electromagnetic energy absorption is permitted to continue until the desired material abrasion is complete, so that substantially most of the deposited electromagnetic energy is removed from the target material with the ejected portion of the material.

Electromagnetic energy absorption is repeated at a pulse repetition rate greater than 0.1 pulses per second such that most of the cumulative residual thermal energy which remains in the material due to the pulse train is removed by the cumulative ablation. The pulsed repetition rate is thus preferably smaller than approximately 100,000 pulses per second and continues until a sufficient depth of material has been removed with substantially no transfer of thermal or mechanical energy into the remaining material and substantially no collateral damage thereto.

The first controller preferably comprises a switching device which deflects sequential portions of the beam and redirects them to separate locations such that the net effect at each location is that of a sequence of pulses of specific duration and specific pulse rate. In this manner, rather than illuminating the entire portion of material to be ablated, different portions thereof are illuminated sequentially, thereby enhancing the ability of the cooperating beams to remove heat therefrom.

The first controller preferably comprises a switching device such as a rapidly rotating mirror, a Kerr cell, a Pockels cell, and acousto-optic modulator, an electro-optic modulator, or other electro-optical, electrical, magnetic, or electromagnetic means for redirecting light.

These, as well as other advantages of the present invention will be more apparent from the following description and drawings. It is understood that changes in the specific structure shown and described may be made within the scope of the claims without departing from the spirit of the invention. The method for ablating a material with a directed energy pulse, such as that of a laser, includes directing a pulse of energy at the material so as to ablate a quantity of the material and so as to permanently modify a quantity of the material, the pulse being configured to increase a ratio of the quantity of the material which is ablated thereby with respect to a quantity of the material which is permanently modified thereby. Alternatively, a plurality of pulses of energy are directed at the material so as to ablate a quantity of the material and so as to permanently modify a quantity of the material, the pulses having a sufficient pulse rate as to increase a ratio of the quantity of the material which is ablated thereby with respect to the quantity of the material which is permanently modified thereby. Ablating the material with an energy pulse or with a plurality of energy pulses configured so as to increase the ratio of the quantity of the material which is ablated thereby with respect to the quantity of the material which is permanently modified thereby minimizes undesirable permanent modification of the material.

BRIEF DESCRIPTION OF THE DRAWINGS

These and other features, aspects, and advantages of the present invention will be more fully understood when considered with respect to the following detailed description, appended claims, and accompanying drawings, wherein:

FIG. 2b, is a graphical representation of the time-dependent intensity profiles (in arbitrary units, au) of transmitted pulse-shapes for a successively higher intensity incident pulses, wherein increasingly higher plasma's electron densities lead to increasingly larger laser pulse reflection and truncation;

DETAILED DESCRIPTION OF THE PREFERRED INVENTION

Figure 1:
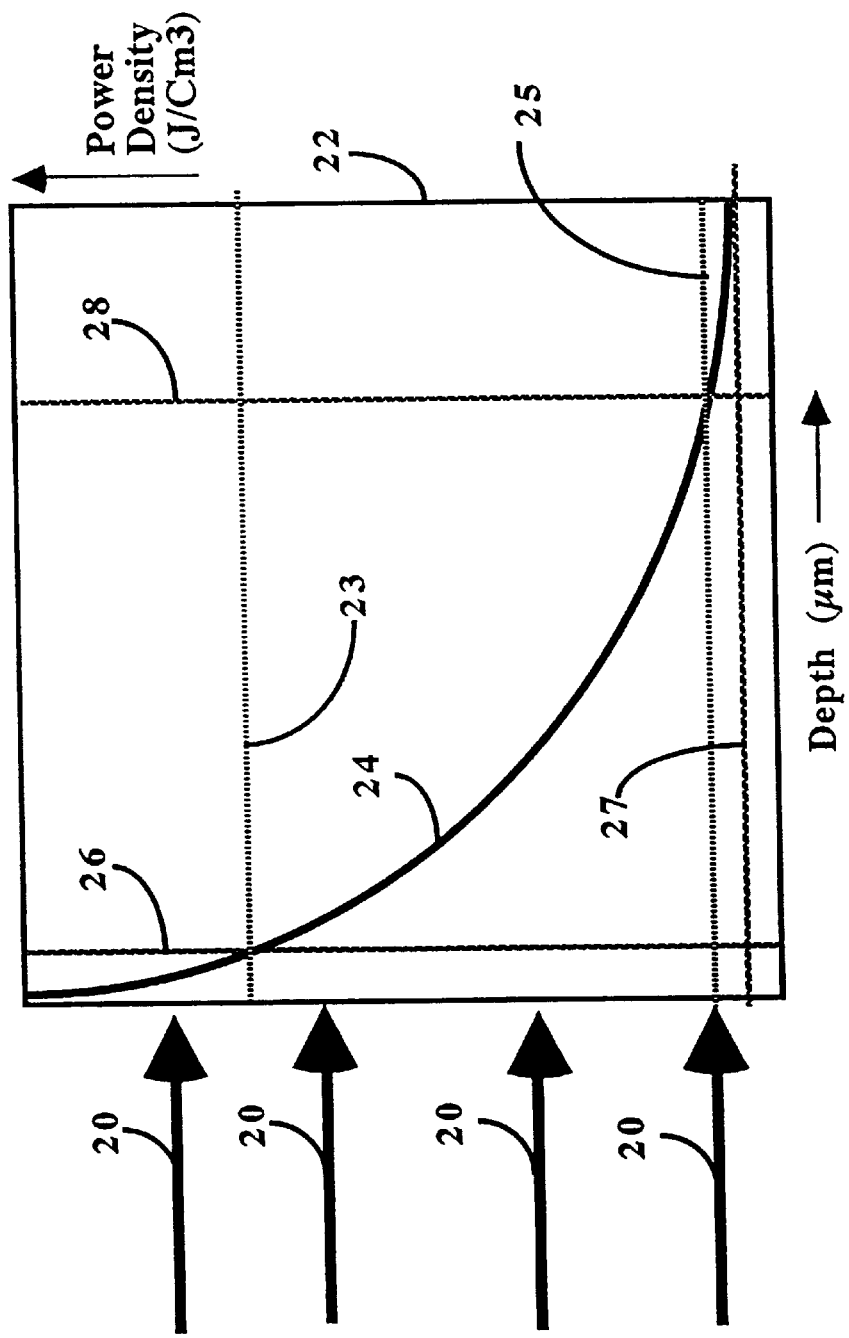
FIG. 1, is a graphical representation of the relationship between the depth of energy deposition and the depth of material removal, also showing an exemplary representation of the spatial distribution of the deposited power density as a function of distance into the target material.

The principles of operation for an exemplary material removal and modification system are described in detail below. The system comprises a source of pulsed electromagnetic radiation and complying with the requirements of the invention. In the following discussion, a laser source is used as an exemplary pulsed source of electromagnetic radiation. However, those skilled in the art will recognize that the invention is not limited to laser sources and that other pulsed electromagnetic radiation sources may serve equally well in the practice of the present invention. The principles of operation of such an exemplary laser system will now be developed in connection with the mechanisms for material and tissue processing such as, for example, the machining of silicon surfaces or the treatment and removal of dental tissue and materials.

The description of the operation of this laser system with respect to applications of silicon machining or dental tissue processing is used for exemplary purposes only and is not intended to limit the applications of the present invention. As will be described in greater detail below, the apparatus and methods for this invention have application for a wide variety of material modification, removal and processing. Additionally, this laser system has exceptional utility for biomedical, surgical, machining, and micro-machining purposes.

The inventor has identified an electromagnetic source-material operational parameter regime which provides interaction characteristics that are superior to conventional machining, other laser systems, and established material processing or material modification systems, and which provides material removal rates that are superior to or on a par with mechanical tools technology. Advantageously, the aspect of the present invention relating to the method's reliance on the system's ability to limit the amount of per-pulse-energy coupled to the material, and the system ability to remove most of the residual deposited energy generated by the interaction itself, results in a very significant reduction in the level of collateral damage while allowing large volume removal at very rapid rates.

The aspect of the present invention relating to a method for rapid material removal capabilities is based on the inventor's novel discovery regarding the relationship between material removal rates and characteristics of a single pulse—interaction with the target material. Specifically, the parameter regime of the present invention, ensures that most of the incoming electromagnetic pulse energy that is absorbed by the material is subsequently removed with the ejected material. Within this parameter regime, variable pulse application rates—including very high pulse repetition rates (up to about five hundred kilohertz) and, correspondingly, very high material volume removal rates—can be achieved.

The ability to vary operation rates continuously from the very high pulse repetition rates (on the order of a few hundred Kilohertz) to the very low (on the order of a single pulse every few seconds, or a fraction of a single Hertz), combined with the relatively small amount of material removed by a single pulse, corresponds to an unusually high degree of control over the material or tissue removal and/or modification, from the extremely rapid to the very slow.

This capability of the invention corresponds to many unusual and highly beneficial uses which include: high precision, superb accuracy, minimization and control of pain sensation (in biomedical applications of the invention), and very high degree of control over removal rates.

The inventor has identified four methods for advantageously defining the interaction parameters.

The first method for advantageously defining the interaction parameters comprises utilizing material properties and beam characteristics or parameters, which results in an electromagnetic energy deposition profile that concentrates the tissue-modifying energy in a zone with a depth of same order of magnitude of the depth of material removed by each pulse. This criteria shall, in the context of the present invention sometimes be referred to as "the principle of near-parity". The principle of near-parity between ablation depth and the depth of permanently modified tissue implies a high ratio of ablation depth to depth of permanently modified matter. This criteria should also be applied in combination with sufficiently short pulse duration to prevent significant thermal diffusion from the energy deposition zone prior to material removal. Pulse duration shorter than 1 µs, for example, means that all the pulse energy is deposited into a target water-like material before thermal energy in the deposited zone has time to diffuse more than about 1 pm away from the deposition volume. If, for example, the pulse energy is sufficient to raise the material temperature to above the boiling temperature, the material within the deposition zone will be vaporized and some of its heat will be ejected with the plume of debris. Alternatively, ionization threshold or threshold for explosive material removal, may be exceeded within in the volume, again, leading to material ejection and ejection of some of the heat with it.

Energy deposition depth which is localized in space and in time naturally leads to the generation of very high power densities within the target material. "Power density" is defined herein as the amount of energy per unit time per unit volume. High power densities play a crucial role in the initiation of the desired interactions, as will be explained in details below.

The shallow deposition, on the same order of magnitude of the depth of the depth of material removed by each pulse, in combination with sufficiently short pulse duration (to prevent significant thermal diffusion from the energy deposition zone prior to material removal), ensures that most of the deposited single-pulse energy in the material is removed with the ablation ejecta of that very same pulse.

Employing a pulse repetition rate of sufficiently large value ensures that, if and when longer total treatment times are needed, most of the residual cumulative pulse train energy coupled to the material is ultimately removed by the cumulative ablative effect of the rapidly moving ablation front. Such a scheme has been identified by the inventor to ensure removal of most of the deposited energy and to allow a variable pulse repetition rate interaction which includes pulse repetition rate of up to about several hundred thousand pulses per second.

As used herein "material properties" are defined as the material mechanical, thermal, optical and electromagnetic characteristics, for example, heat capacity, optical absorption, electrical conductivity etc. "Beam characteristics" are defined as the beam spot size at the target location, the beam pulse energy, the beam pulse duration, the beam pulse repetition rate, pulse-to-pulse separation time, etc.

The second method for advantageously defining the interaction parameters comprises utilizing material properties and beam characteristics so that a plasma is generated through either multiphoton ionization and/or thermal ionization. Properties of such an interaction (as discussed below) often ensure: a) shallow depth of energy deposition (in accordance with the above), b) plasma shielding and (above critical electron density value) increased rejection of subsequent incoming radiation, and c) removal of much of the deposited energy with ejected layer.

The shallow deposition, comparable in depth to the depth of material removed by each pulse, in combination with sufficiently short pulse duration (to prevent significant thermal diffusion from the energy deposition zone prior to material removal), ensures that most of the deposited single-pulse energy in the material is removed with the ablation ejecta of that very same pulse.

Employing a pulse repetition rate of sufficiently large value ensures that most of the residual cumulative pulse train energy left in the material is removed by cumulative ablative effect of the rapidly moving ablation front. Such a scheme has been identified by the inventor to ensure removal of most of the deposited energy and allows variable pulse repetition rate interaction which includes pulse repetition rates of up to about several hundred thousand pulses per second.

The third method for advantageously defining the interaction parameters comprises adding absorption centers, localized defects in the material, and/or highly absorbing or highly scattering components (collectively defined by the inventor as "doping agents") to the target material so that the electromagnetic radiation penetration depth is reduced and/or plasma is formed. Temporally and/or spatially marking the targeted material zone with a doping agent, prior to or during the incoming electromagnetic energy arrival time, in combination with sufficiently short pulse duration (to prevent significant thermal diffusion from the energy deposition zone prior to material removal) results in shallow incoming electromagnetic energy deposition depth.

The shallow deposition, comparable in depth to the depth of material removed by each pulse, in combination with sufficiently short pulse duration (to prevent significant thermal diffusion from the energy deposition zone prior to material removal), ensures that most of the deposited single-pulse energy in the material is removed with the ablation ejecta of that very same pulse.

Employing a pulse repetition rate of sufficiently large value so that, if longer total treatment time is needed, it ensures that most of the residual cumulative pulse train energy left in the material is removed by cumulative ablative effect of the rapidly moving ablation front. Such a scheme has been identified by the inventor to ensure removal of most of the deposited energy and to allow a variable pulse repetition rate interaction which includes pulse repetition rates of up to about several thousands pulses per second.

The fourth method for advantageously defining the interaction parameters comprises utilizing the power density threshold nature of the interactions (for example through pulse temporal and/or spatial compression), or utilizing preferential time-dependent and/or space-dependent marking of the target material, it is possible to chose material properties/beam characteristics combination so that only a pre-selected volume at or below the target material surface, is modified or removed. Employing such selected parameter combination with sufficiently short pulse duration which prevents thermal diffusion from the energy deposition zone prior to material removal or modification results in significant minimization of collateral damage.

Here, material modification pertains to altering the physical and/or chemical conditions of material without providing sufficient power densities to completely remove or ablate the targeted material. This condition for material modification will occur at power densities higher than those which allow linear propagation without sufficient energy deposition for irreversible changes to occur, yet lower than those defined by the ablation threshold. A selection of the appropriate time and space-dependent material properties/beam characteristics parameter will allow a time and space dependent interaction. The selected beam path can then allow the operator to define temporally and spatially pre-selected target regions, which will include unperturbed zones (where no irreversible changes occur), modified zones (where material physical or chemical characteristics have been modified but no material has been removed), and ablated zones (where complete or partial removal and/or vaporization of material has taken place).

Here, a criteria for high ratio of the extent of a desired and controlled material modification to the extent of undesired material modification is strived for.

Another advantage of the method of the present invention, is that longer wavelength, pulse laser systems can be used in many of the procedures currently employing lasers which operate in the ultraviolet region. Replacing ultraviolet lasers with the longer wavelength ultra-short pulse lasers of the invention would eliminate the risks associated with mutagenic radiation produced by short wavelength lasers, and the attendant dangers posed.

A further advantage of the present invention is that pulsed, solid-state lasers can be used in most, if not all, procedures currently employing various fluid lasers (for example dye-based lasers), as well as gas and excimer lasers which involve manipulation and handling of expensive and dangerous gas components. Replacing ultraviolet excimer lasers as well as other types of dye and gas lasers with the pulse solid state lasers of the present invention would eliminate possible exposure of operators to carcinogens and poisonous liquids and gasses.

Principles of Operation: High Ratio of Ablation Volume to Permanently Modified Volume Incident electromagnetic energy can propagate in some materials much as it does through free space, air, or any other transport media. Transport media is defined herein as the media which the beam has to transverse on its way from the source to the targeted material. Normally, the source parameters and the transport media properties are chosen so that minimal beam energy will be deposited or lost in the transport media. By definition, the desired alteration to the target material requires energy deposition at the designated volume. Once the electromagnetic pulse arrives at the target medium, more substantial energy deposition is accomplished through the interaction of the radiation with the media atoms and electrons. The interaction can be relatively weak in which case substantial amounts of energy are transported through the target material and are deposited in much deeper regions or, perhaps even, completely traverse the targeted material volume and emerge at the opposite boundary of the material. Radiation with a wavelength of 1.06 $\mu$m loses 1/e, (approximately one third) of its original energy in a length (sometimes called "penetration depth") which, for this wavelength propagating in water is on the order of 16 mm. If the interaction is strong, the radiation loses energy at a very rapid rate as it propagates into the material. Radiation of 2.94 $\mu$m radiation propagating through water, for example, drops to (1/e) (or about one third) of its incident energy value at a penetration depth of only about 1 $\mu$m or 0.001 mm.

Once the energy has been transferred from the beam to the material atoms, it will further propagate into adjacent, lower energy, regions of the material. This additional transport usually takes place through either mechanical or thermal energy propagation although some radiation transport is possible as well.

The practice of the present invention maximizes deposition of the incoming radiation within the area targeted for ablation or alteration, and minimizes deposition or further transport of the energy to adjacent region thus minimizing the depth of the zone of matter which has been permanently modified. Moreover, the inventor realized that if most of the deposited energy is removed with the ejected debris, very little energy is left within targeted material, thus allowing a large number of pulses to be deposited within the same area of the targeted material within a short time duration. The inventor recognized that the deposition of large number of pulses within a short time duration, which corresponds to high pulse repetition rate, is only possible because of the condition which the present invention imposes on the interaction, namely, that most of the energy deposited by a single pulse will be removed by the ablation products ejected from the material due to the action of the very same pulse.

The above discussion can be summarized by defining (1) $x_{irr}$, the depth of the zone of irreversible damage, as the depth to which most of the pulse energy capable of irreversibly modifying the target material has been transferred (either by direct interaction with the electromagnetic pulse or through subsequent thermal diffusion, or both), prior to the ablative removal of the material. "Irreversibly modifying" the material is defined as ejecting, ablating, and/or otherwise irreversibly changing material characteristics. We also define $X_{abl}$ as the depth of material ablatively removed through that very same incident pulse deposited energy. The condition for high ratio of ablation to permanently modified material depths amounts to requiring that the ratio $(X_{ab}/X_{irr})$ be as high as possible.

As the above ratio approaches one, this requirement can be expressed as $X_{irr} \sim X_{abl}$, which corresponds to near-parity between energy penetration depth and the depth of material ablated per pulse. The requirement that the ratio $X_{ab}/X_{irr}$ 1S as long as possible is of paramount importance to the practice of at least one embodiment of the present invention.

FIG. 1 illustrates the concept of parity between thermal penetration depth and the depth of material ablated per pulse. In FIG. 1, electromagnetic energy 20 impinges on a slab of material 22 from the left. The curve 24 depicts the power density as a function of distance (or beam propagation depth) into the target material and corresponds to an exemplary energy deposition profile within the material. If the line 27 represents the threshold for material modification and the line 23 represents the threshold for material ablation, then the vertical line 26 represents a material removal depth which is insufficient to meet the criteria of high ratio of ablation to energy deposition depths. Since the area under the curve 24 is proportional to the total amount of incoming energy deposited in the material, removal of the layer to the left of 26 clearly represent only a small fraction of the deposited energy. On the other hand, if the lower line 25 represents the threshold for material ablation, then the vertical line 28, represents the depth of material removal which corresponds to an exemplary depth which adequately meet the requirement of the above criteria, since ablation to this depth clearly removes most of the deposited energy.

The requirement for a high ratio of ablation volume to permanently modified volume can be achieved in several ways. One avenue to satisfy this requirement is to employ wavelength which results in shallow electromagnetic energy deposition and high power density within this volume—a power density which leads to near-parity of the ablated volume and the energy deposition volume. A second avenue is presented when plasma is generated in the course of the interaction between the pulsed energy and the targeted material. This avenue will now be described below.

Previously known and frequently used laser systems, characterized by the lack of a high ratio of ablation volume to permanently modified volume (usually operating in the low pulse intensity regime ranging up to 1,000 watts/cm$^2$ and often based on continuous emission sources), were demonstrated to be generally unable to remove substantial amounts of material without causing extensive collateral effect.

In conventional long pulse laser systems (for example, conventional low intensity Neodymium:YAG or a continuous wave CO2 or dye laser systems) much of the optical energy delivered to a material target site does not go into disrupting the structural integrity of the target material, but is transferred into the surrounding tissue as thermal, acoustic, chemical or mechanical energy. This energy propagates through the surrounding tissue as both transient mechanical energy and heat energy. These, in turn, manifest themselves as undesirable cracks in the material, material charring, discoloration, surface melting, chemical alterations, and, in the case of living animals and human beings, in the sensation of pain.

Conventionally, for long pulses or continuous wave sources, large penetration depths or low power density interactions, bulk material removal involves the heating of conduction band electrons by an incident beam of photons and the transfer of this thermal energy to the bulk resulting in melting, boiling, and/or fracture of the material in the region in which removal is desired.

Because the controlling rate for material removal depends on thermal response of the material lattice and the lattice's thermodynamic properties (heat capacity, heat of vaporization, heat of fusion, and the like), the minimum amount of energy required to effect an observable change in the materials properties, (the threshold damage fluence defined as the incident beam energy per unit area) is approximately proportional to the square root of the pulse duration.

In such systems, the total amount of material removed is limited by the amount of material removed with each pulse, the number of pulses per second, and the total beam application time (i.e., the total time that the material is allowed to be exposed to the beam). Also, the amount of material removed by a single pulse, is proportional to the volume effected by the electromagnetic energy deposition, thermal energy penetration, diffusion, and mechanical energy propagation due to a single pulse deposition event. As a consequence, high pulse energy has, in the past, been considered necessary in order to obtain adequate material removal characteristics.

Unfortunately, high per-pulse energies which are often required by conventional longer pulse or continuous wave laser systems are often the source of many undesirable side effects such as, extensive melting and boiling beyond the intended target volume, explosive vaporization and tearing at the boundaries, as well as fracture of the material surface.

Much improved and unexpected results are obtained, however, when material removal is performed with sources yielding high values of $X_{ab}/X_{irr}$ through, for example, plasma-mediated interactions. When laser systems are operated in a parametric regime where power densities are larger than plasma formation threshold, the physical mechanism of material removal radically changes as explained below.

Plasma is a highly ionized gas in which the number of free electrons is approximately equal to the number of positive ions. It is generated in the material by the incoming radiation through either multiphoton ionization and/or intense heating of the material leading to collisional ionization. Plasma-induced damage is typically confined to small volume bounded by the region of the beam's intensity profile which is above the ablation fluence threshold and with sufficient beam intensity to produce ionization.

The beam temporal and spatial power density distribution can be achieved in one of several ways: 1) the photons can be concentrated in a short time-duration bursts, where a shorter pulse duration yields a greater photon concentration, 2) the beam can be strongly focused to a smaller spot where the smaller the spot, the greater the photons spatial concentration, 3) the material absorption and/or scattering characteristics are such that most of the photons penetrating the material are confined to a small depth, and finally, 4) by adding highly absorbing and/or scattering doping to the material, the same effect of confining high photon energy deposition to a small volume can be achieved.

If a high photon concentration is achieved, through either one or a combination of the above avenues two effects may follow: 1) the radiation ceases to propagate linearly, and non-linear multi-photon absorption and multi-photon ionization lead to the production of free electrons, 2) a significant increase in thermal energy density and thermal ionization of the material also leading to the production of free electrons and ions. These two processes can and often do occur simultaneously.

The free electrons, then act as seed electrons which cause an avalanche process or an electron ionization cascade through collisional processes in which material conduction band electrons, oscillating in response to the laser optical field, transfer their energy to additional electrons and to the material lattice through phonon scattering. Once an electron acquires kinetic energy equal to or larger than the band gap energy for the materials, subsequent collisions with adjacent electrons and impact ionization promotes an additional valence electron into the conduction band. The resulting avalanche leads to destruction of the material lattice and to an irreversible change in the bulk material structure.

If the target material linear absorption at the selected source wavelength is low, the beam will propagate with little or no effect on the target material. Thus, regions where the beam power density is below that which are required for plasma generation will remain unaltered. Only those regions within the beam power density profile which are capable of creating plasma will interact with the targeted material and will result in material alteration and removal. As a consequence, damage occurs only in the material volume irradiated by sufficient power densities to produce ionization.

In addition, because the plasma-mediated interaction process is threshold-dependent and based on the principle that only material which experience above-threshold optical energy deposition is removed, melting or boiling is minimized and the energy deposition does not correspond to significant heating or thermoelastic stress.

Also, since most of the energy is deposited in a thin outer layer of the material, and since after the ablative interaction with the leading portion of the pulse, subsequent energy is coupled mainly to the plasma which shields the target material from non-ablative energy, most of the energy within the target material is removed with the ablated ejecta. This condition is part of the requirements for the practice of the present invention as the inventor described in the discussion above. Plasma-mediated interactions are, therefore, a class of interaction that naturally fulfill this requirement.

The amount of residual heat left in the material depends on the laser-material coupling characteristics. Once plasma is formed, its presence defines the coupling and shielding characteristics which are relatively uniform (with little dependence on material properties) for a given plasma density.

Thus, in the practice of the present invention, once the ablation characteristics for a given plasma electron density have been established, pulse duration can be adjusted so that additional source energy and plasma expansion will not result in excessive accumulation of residual heat and will not lead to rise in material temperature above a given limit (for example: the limit for material carbonization in biological tissue during surgery, or melting in silicon during a material processing procedure). Source maximum pulse repetition rates and maximum material removal rates can then be established based on these single pulse ablation characteristics and the single pulse minimal residual heat deposits.

As will be discussed below, an additional consequence of the method of the present invention is the ability to manipulate the power densities in the material through the manipulation of beam parameters and/or addition of material doping agents. This allows the user to achieve: a) a selective interaction, and, b) a relatively high level of insensitivity of the ablation threshold and the material removal rate to the laser wavelength, material chromophore, material structure, material state of hydration, and material state of oxygenation. Some of the basic concepts described above will now be developed.

The physical characteristics of an exemplary system for use in removing and modifying material, as illustrated by the present invention, will be best understood by initially referring to both FIG. 2 and FIG. 3.

Figure 2A:
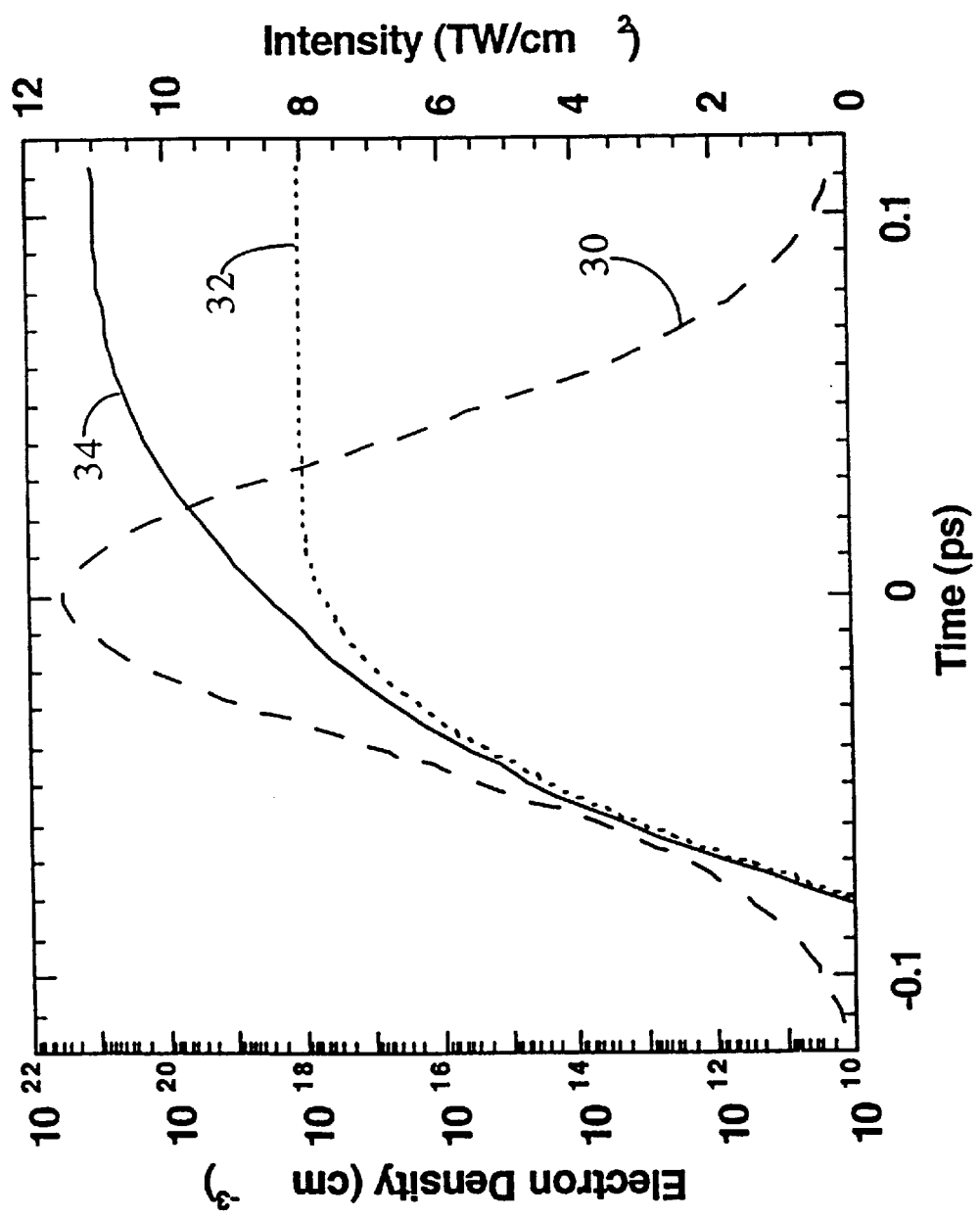
FIG. 2a, is a graphical representation of the time-dependent evolution of the plasma electrons density due to multiphoton and collisional ionization in relation to the incident pulse temporal profile.

FIG. 2a depicts the evolution of the plasma free electron density (which corresponds to the state of the plasma) as a function of time following the start of the interaction with the leading edge of the electromagnetic pulse. Production of free electrons by multiphoton ionization alone 32 (dotted curve) and by multiphoton and collisional ionization 34 (solid curve) is shown. For reference, the time-dependent intensity profile of the incident light pulse 30 (the "bell-shape" curve in the figure) is also shown.

As FIG. 2a clearly indicates, the leading edge of the pulse rapidly yields high power densities in the outer layer which generates plasma whose electron density increases over the leading portion of the pulse and gradually reaches a maximum level during the second part of the pulse. Note that while the time and intensity scales are linear, the electron density scale is logarithmic and the FIG. 2a indicates a very rapid rise in electron density. It is the use of plasma's electron density properties that, according to one aspect of the present invention, allows some of the unique interaction characteristics of plasma-mediated interactions as contemplated by the present invention.

As the electron density increases, reflection and absorption in the plasma increases correspondingly. Consequently, a large portion of the trailing segment of the pulse does not reach the target material.

In FIG. 2b the intensity profile of an exemplary, unperturbed, incident pulse 40 is shown as a dotted line. In the case of linear propagation through the material, the shape of the intensity profile is maintained. The only difference between a pulse transmitted through a vacuum and that transmitted linearly through matter is that in the linearly absorbed pulses the profile intensity is reduced (or attenuated). The shape of the pulse, however, is maintained. In the example of FIG. 2b, if a linear propagation through 1 mm of material results in 10% absorption, the beam intensity profile after propagating through the material will be approximately 7.2 A.U. at −0.1 ps, down from the 8.0 A.U. shown for the incident beam at −0.1 ps. For the same conditions, the beam peak intensity at time 0 ps will be 18 A.U. as opposed to the 20 A.U. shown for the incident beam at 0 ps, and so on. Every portion of the pulse intensity will be attenuated by the same proportion, i.e., 10% for this example.

An entirely different situation is encountered when the pulse interacts with the material non-linearly and plasma is formed. Here, because more free electrons are generated by higher intensities, the attenuation is proportional to the incident beam intensity and are not constant (for example 10% as in the example above) for every portion of the beam time profile, nor is the attenuation constant for different beams with different intensity profiles.

As one can see from FIG. 2b, an increase in the incident pulse intensity (which corresponds to an increase in the electron density generated within the plasma) results in a larger and more significant photon reflection and absorption by the plasma. These effects truncate the pulse and prevent most of the latter portion of the pulse energy from reaching the target. An increase in the incident pulse intensity results in a correspondingly larger portion of the pulse being shielded by the plasma and prevented from reaching the target. Thus, a higher intensity of the original beam results in a larger portion of the incident pulse being truncated.

If, for example, the incident beam intensity is progressively increased from intensity profile level $I_1$ (where the beam intensity is very week and propagates linearly) to an intensity level $I_5$, where the beam assumes its highest intensity, then a progressively larger portion of the incident beams will be eliminated through increased reflection and absorption by the plasma.

FIG. 2b illustrates this plasma shielding by showing the effect of the plasma on removing progressively larger portion of energy from the incident pulse. Thus, the curve 40 corresponds to the unperturbed incident beam while curves 42, 44, 46, and 48 show the elimination of progressively larger and larger portion of the original beam as the beam intensity is progressively increased from level $I_1$ to $I_5$. The portions to the right of each of the curves 42, 44, 46, and 48 represent the amount of energy absorbed or reflected by the plasma, while the portions to the left of these curves, correspond to the fraction of the incoming beam that is able to arrive at the material. Note that until the point where the plasma's electron density is high enough to initiate truncation, the beam intensity profiles of curves 42, 44, 46, and 48 share the same intensity profile of the original unperturbed beam (the left portion of each of these curves). It is only when plasma reflection and absorption are significant that the shielding effects truncate the beam into the shapes represented by the right-hand-side of each curve.

FIG. 2b also shows that as the intensity of the incident pulse increases truncation begins earlier in time and a smaller fraction of the beam arrives at the target material before shielding takes effect.

Finally, FIG. 2b also shows that when some critical level of electron density is reached, the fraction of the beam that can arrive at the target material before shielding takes effect becomes substantially constant. This is indicated by the fact that the shape of the intensity profiles remains essentially unchanged in response to an increase in the incoming beam energy. Thus, the curve 46 and the curve 48 in FIG. 2b remains essentially constant. This means that the excess energy packed into the incoming beam $I_5$ has been reflected or absorbed by the plasma to leave the portions of the beam allowed to penetrate into the target material—essentially unchanged.

Again, this saturation in the amount of energy that is able to arrive at the target material occurs because both $I_4$ and $I_5$ (the incoming beam profiles corresponding to the curve 46 and curve 48) are intense enough so that the critical electron density is reached substantially simultaneously for curve 46, and curve 48, and the subsequent additional beam energy in the more intense pulse $I_5$, either increases the free electrons kinetic energy (i.e., increases the heating of the plasma) or is simply being reflected.

Figure 2C:
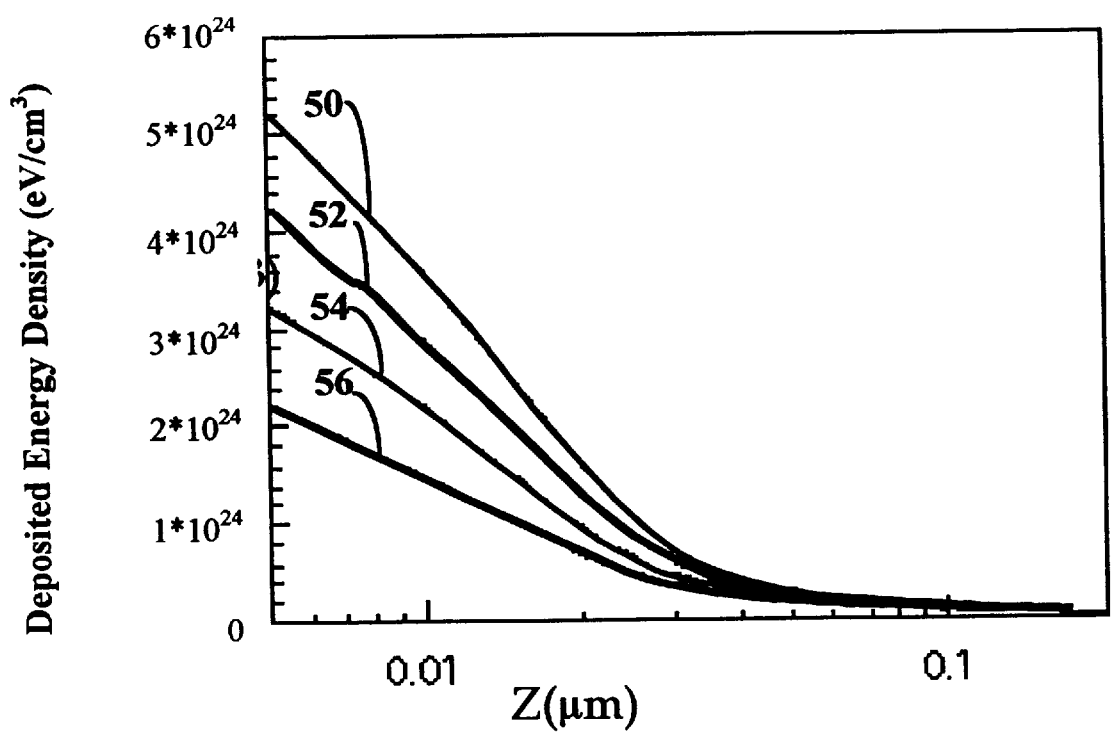
FIG. 2c, is a graphical representation of the free electron energy density as a function of depth, wherein increasing the incident pulse intensity yields larger energy densities, but not much thicker energy deposition layer.

FIG. 2c illustrates another useful feature of the plasma characteristics used in the present invention. As was indicated above, plasma shielding prevents excess energy from reaching the target material. Thus, once a high electron density has been generated, an increase in the incident laser pulse intensity results in an increase in the amount of reflection and absorption by the plasma electrons and a corresponding increase in their average energy. Thus, in FIG. 2c, an increase in the incident pulse intensity from level 56 to level 50 results in a corresponding increase in deposited energy density but not in a corresponding increase in the deposition layer thickness. In fact, as FIG. 2c clearly shows, the thickness of energy deposition corresponding to the lowest energy beam 56 is not much deeper than the deposition layer thickness due to the highest energy beam 50.

Thus, as FIG. 2c shows, the plasma shielding naturally ensures that the energy deposition layer does not become correspondingly thicker but is, instead, maintained at a relatively constant thickness. This relatively constant energy deposition depth was also which is relatively which is relatively insensitive to increase in incidence beam energy was also indicated by the ablation depth data (see discussion below), which clearly shows that increase in incoming energy does not yield a significant increase in the amount of material removed.

The present invention makes use of the effects described above. Simply put, it is these plasma characteristics which act as a natural limiting factor for the amount of light that can be directly coupled to the material, and it is the plasma properties that limit the thickness of the energy deposition layer and the depth of the material being affected. Thus, if the material and/or beam characteristics allow plasma and free electron generation, the interaction characteristics become relatively uniform. As was shown above, regardless of other material or beam properties, (such as the exact details of the material thermal, optical, and mechanical properties, or the beam wavelength characteristics), the interaction is dominated by the plasma electrons absorption and reflection exhibited in FIG. 2a to FIG. 2c. Therefore, as the inventor recognized, it is the plasma interaction properties that dominate the material removal and modification process.

While light penetration of and absorption by the plasma also depends on the wavelength of the incident radiation, and to some extent on other material and beam characteristics, this dependence, especially when multiphoton ionization is involved, is indirect and much weaker than in the linear case. Thus, plasma interactions with the incident light are more uniform and much less sensitive to beam and material parameters than in the case of linear interactions. As will be explained further, it is this unifying characteristic of the plasma-mediated interaction, that is used, according to one aspect of the resent invention, to improve material processing procedures and make the present invention relatively insensitive to material properties and material type.

Thus, FIG. 2a through FIG. 2c illustrated the advantages of the aspect of the invention using plasma-mediated interaction: once plasma is formed, the interaction ceases to depend on the specifics of the targeted material and becomes much less sensitive to the beam parameters. This significant reduction in sensitivity to beam parameters also means that once plasma formation is accomplished, excess beam energy is accommodated by the electrons in the plasma. In this case, excess energy is mostly rejected instead of reaching the material directly and increasing the heating and mechanical coupling to the material.

The examples and illustrations presented below, now show how some of the parameters required for achieving high volumetric power density, onset of plasma, and critical electron density, (namely, pulse duration, beam spot size, scattering, absorption and wavelength), can be used in the practice of the present invention, to take advantage of the above outlined unique characteristics of plasma-mediated interaction.

FIGS. 3a through 3f represent an additional aspect of the operation as described by the present invention, and manifested through the dependence of the material removal rates, on the beam power density at the targeted volume of material. The figures illustrate the observed removal rates dependence on the beam's fluence (beam energy per unit area), wavelength, and pulse duration. Through these figures we can understand the invention principle of controlled interaction through control of the volumetric power density and the plasma interaction regime.

The Laser beam power density at the target area defines the dominant ionization process, subsequent electron density, and ultimately, the plasma interaction regime, which, in turn, result, in unique ablation characteristics. For a final removal rate on the order of a few micrometer per pulse, the inventor identified the following approximate divisions into three characteristic interaction classes:

Class 1. Very high power density regimes, generated through either, very short pulses (less than about 10 ps) and/or very high pulse energy, and/or very high absorption. Regardless of the dominating mechanism, the resulting power densities at the target material are in the range of more than about $10^{15}$ w/cm$^3$. In this range multiphoton absorption plays a dominant role and ablation rates are very uniform and are relatively independent of the precise details of the material characteristics and the wavelength of the beam.

Class 2. Moderate power density regime generated through either, short pulses (from about 10 picosecond to about 100 nanosecond) and/or moderate pulse energy and/or moderate energy deposition depths resulting in power densities at the targeted volume in the range of from about $10^{11}$ w/cm$^3$ to $10^{15}$ w/cm$^3$, and characterized mostly by thermal ionization. In this regime the interaction process becomes more sensitive to material type and to beam wavelength. In this case depth of ablated material tends to be slightly larger than class 1 because of the deeper linear penetration prior to full development of the plasma. Here, ablation depth per pulse tends to range from a single to several micrometers in depth. Because of the lower power densities involved, ionization is slower and plasma shielding is not as effective as that of class 1. As a result, a deeper energy deposition is often the consequence This consequence may violate the inventor's requirement for approximate parity between deposition and ablation depth and may lead to larger residual energy left in the material and a more significant cumulative heating will follow. The possible development of some thermal and/or mechanical collateral damage is the ultimate outcome of the this class of interaction.

Class 3. Lower power density regime generated through either longer pulses (from about 100 nanosecond to about 10 ms) and/or lower pulse energy and/or larger energy deposition depths resulting in power densities at the targeted volume in the range of from about $10^7$ w/cm$^3$ to $10^{11}$ w/cm$^3$. Here, the interaction is even more sensitive to material characteristics and to the beam wavelength. The ablation rates fluctuate widely from about a fraction of a micrometer to over about five micrometer per pulse. At the same time both collateral thermal and collateral mechanical damage fluctuate significantly in response to the conditions for volumetric energy densities deposition and to plasma initiation and to how close conditions are to satisfying the parity condition discussed above. The ultimate characteristics of this class of interaction is a relatively less predictable material removal and modification performance of systems operating within this interaction class.

These divisions are rather imprecise and are made only for the purpose of general classification of the categories of the interaction classes, all of which are used in the practice of the present invention. Some overlap and increased interaction complexity may obscure this simplified classification.

Figure 3A:
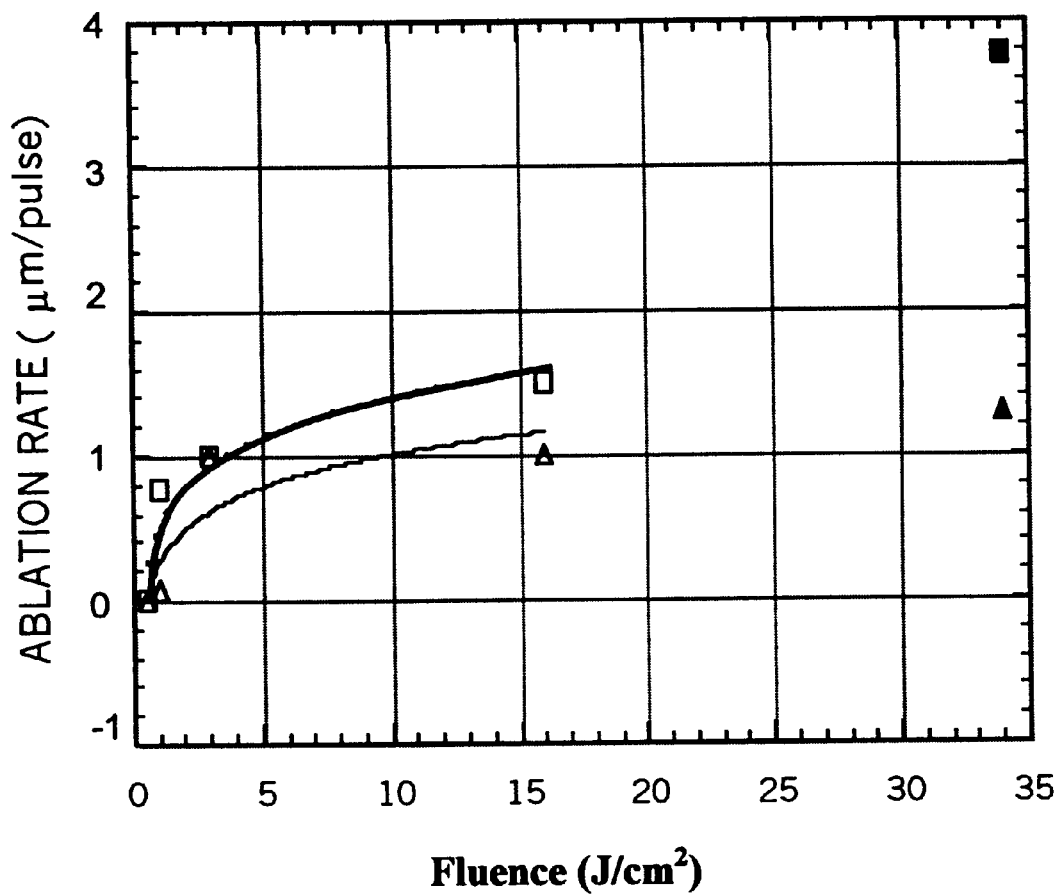
FIG. 3a, is a graphical representation of experimentally determined values of material removal rates in microns per pulse, plotted as a function of laser fluence, of two pulse regimes (350 fs and 1 ns) for exemplary dentin and enamel materials.
Figure 3B:
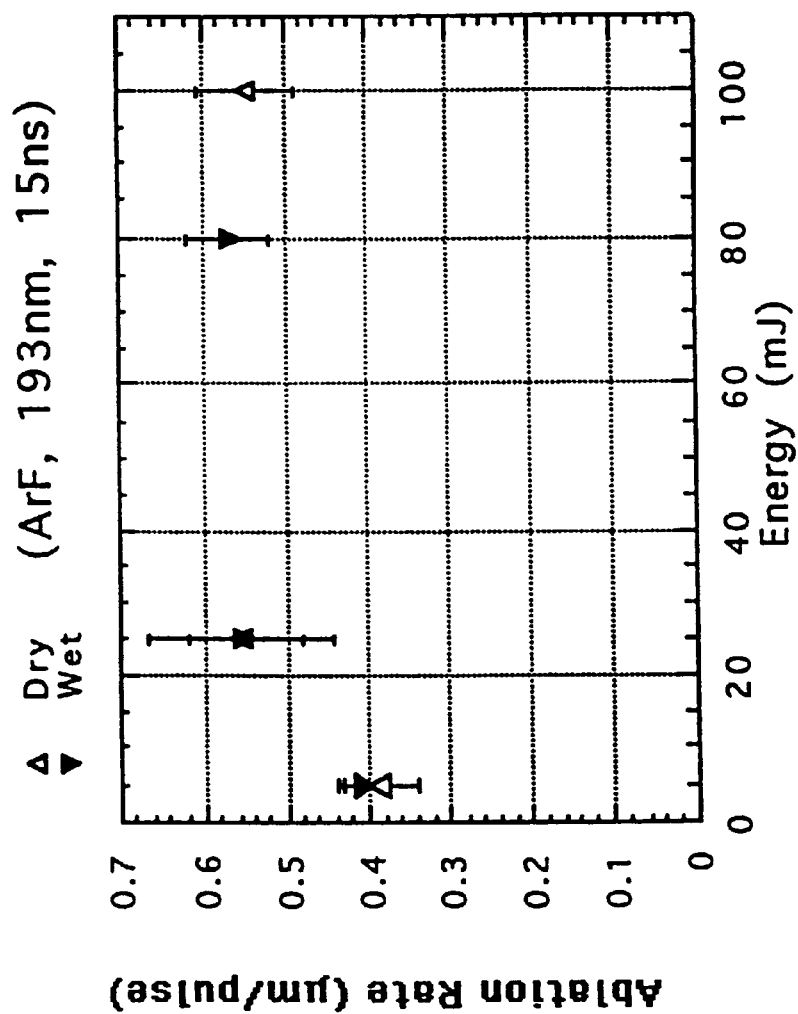
FIG. 3b, is a graphical representation of experimentally determined values of material removal rates in microns per pulse, plotted as a function of laser energy, of a 15 ns, 193 nm ultraviolet ArF Excimer laser for exemplary fresh and dehydrated dentin materials.
Figure 3C:
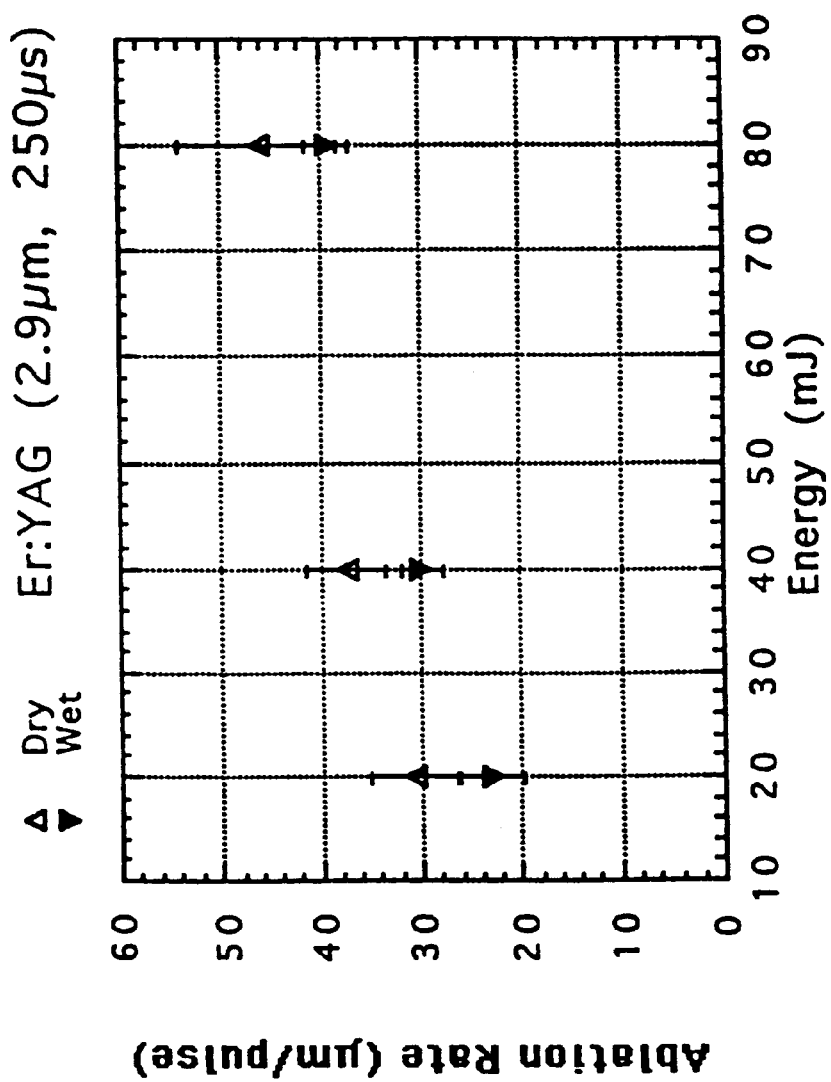
FIG. 3c, is a graphical representation of experimentally determined values of material removal rates in microns per pulse, plotted as a function of laser energy, of a 250 µs, 2.9 µm infrared Erbium:YAG laser for exemplary fresh and dehydrated dentin materials.

FIG. 3a depicts the ablation rates (in micrometers of material removed by a single pulse) for both an exemplary enamel and an exemplary dentin material, ablated by 60 fs laser of 1.05 micrometer radiation wavelength. Note that the range of fluence used for the 60 fs pulses corresponds to power densities in the range of about 0.1 $10^{17}$ to 5 $10^{17}$ W/cm$^3$. For purposes of identification, dentin is represented by 68 while enamel is represented by 65.

FIG. 3a also illustrates an important characteristic of plasma-mediated interaction which was pointed out in the discussion above: both enamel and dentin exhibit a clear ablation rates saturation pattern as pulse energy is increased.

From the ablation threshold at about 0.5 Joules per square centimeter, ablation rate increases rapidly to about 0.7 μm/pulse for enamel and 0.9 μm/pulse for dentin at a fluence level of about 1.7 Joules per square centimeter, where ablation for both tissue types stabilizes at about the same rate. Beyond this point, only a very small increase in ablation rate occurs with increases in fluence. Ablation rates of 1.5 microns per pulse are achieved for dentin material at 16 Joules per square centimeter. This represents only about a 50% increase in ablation rate for over an eight fold increase in fluence level, as compared to 1.7 Joules per square centimeter level.

The diminished return in ablation efficiency is a natural consequence of the plasma interaction characteristics. As the pulse energy is increased, a denser plasma is generated by the leading edge of the laser pulse. The denser plasma absorbs and reflects subsequent radiation, thus shielding the surface and preventing additional energy to be used for deposition.

For purposes of comparison, the ablation rates of dentin and enamel when processed with one nanosecond pulses at a fluence of 34 Joules per square centimeter (about 3 $10^{10}$ W/cm$^2$) were also studied. The nanosecond pulses were produced by the chipped pulse amplifier laser system that also produced ultra short pulses of 350 fs (i.e., the pulses were simply left uncompressed at their 1 nanosecond stretched value) and shared the same 1.05 μm radiation wavelength. This wavelength is characterized by a relatively deep linear penetration, (on the order of a centimeter). Combined with the much longer pulse duration (a factor of approximately 3,000 longer than the 350 fs pulses) the power densities generated by the one nanosecond pulses much lower and are approximately on the order of $10^{10}$ W/cm$^3$, or class 3 interaction.

Nanosecond pulses exhibit an ablation rate of about 4 microns per pulse for dentin, and about 1.4 microns per pulse for enamel, at the 34 Joules per square centimeter fluence level. The inventor has determined that a 3 Joule per square centimeter fluence was well below the ablation threshold of either dentin or enamel for nanosecond pulses, which threshold was determined by experimentation to be in the range of about 20 Joules per square centimeter.

The experiments with nanosecond pulses thus illustrate several important points about the principles of interaction: 1) if the intensity is too low no plasma is formed and no explosive interaction occurs; 2) above a certain threshold—probably around 20 J/cm$^2$ in the case of dentin, plasma is formed and interaction does takes place, and 3) that because light has had a chance to penetrate and heat directly a much deeper region of the target, significantly larger depth ablation is achieved. Since the initiation of plasma in this case is dependent on thermal ionization, much larger power densities are required and much larger quantities of heat must be generated throughout the larger deposition volume.

Also, absorption and scattering characteristics of the two types of materials play an important role in determining the energy densities, thus as is clear from FIG. 3a, the ablation rates for the same fluence level in the nanosecond regime are very different for dentin and enamel, with dentin ablation being almost a factor of four greater.

The role of linear absorption and scattering for pulse durations even longer than the exemplary one nanosecond discussed above, can be demonstrated by the results of FIG. 3b. Here, the pulse duration is approximately 15 ns and approximately 300,000 time longer than the 60 fs pulses of FIG. 3a. Significantly, however, the radiation wavelength here is in the far ultraviolet range at about 193 nm, where scattering and absorption are very large. Thus, in spite of the longer pulse duration (15 nanosecond as compared to the 1 nanosecond example presented above), large power density ($10^{12}$ to $10^{13}$ W/cm$^3$) are achieved due to the concentration of pulse power within a very shallow deposition depth (on the order of a micrometer) and many of the characteristics of the 60 fs class 1 interaction are observed here as well. Thus, similar to the 60 fs case, we observe the same ablation saturation effect (i.e., no significant increase in ablation depth with increasing pulse energy) due to rapid plasma formation at energies beyond 5 mJ per pulse (or fluence of 0.12 J/cm$^2$. Also, note that similar to the case of the 360 fs, the interaction and removal rates are not very sensitive to water content (since both water-saturated, as well as dehydrated, samples strongly absorb and scatter this far ultraviolet wavelength, thus easily generating the high power densities necessary for plasma formation.

For the purpose of demonstrating the practice of the present invention, it is also useful to consider the rather long pulse regime of 1 μs. In the exemplary system of FIG. 3c mid-infrared laser system of Erbium:YAG emitting light in the normal mode of oscillation with macro pulse duration of 250 μs and wavelength of 2.9 μm. The power densities corresponding to the approximately 1 μm absorption depth of this 2.9 μm wavelength and 250 μs macro pulse are on the order of $10^8$ W/cm$^3$, and can belong to the lower portion of class 3. This macro pulse of this system, however, consists of a train of about 20 micro pulses each of 1 μs pulse duration. The power density for these shorter micro pulses is thus on the order of $10^{10}$ W/cm$^3$, almost in the range of interaction class 2. Thus, as can be seen from the Figure, the ablation rate per micro pulse is on the order of 1 to 2 μm, and there is little sensitivity to water content. This illustrates the point that if the interaction is carried out under strongly absorbing conditions (as in the case of the Er:YAG laser radiation) which yield high volumetric power density, the result is ablation behavior similar to the nanosecond and even sub-picosecond systems.

Figure 3D:
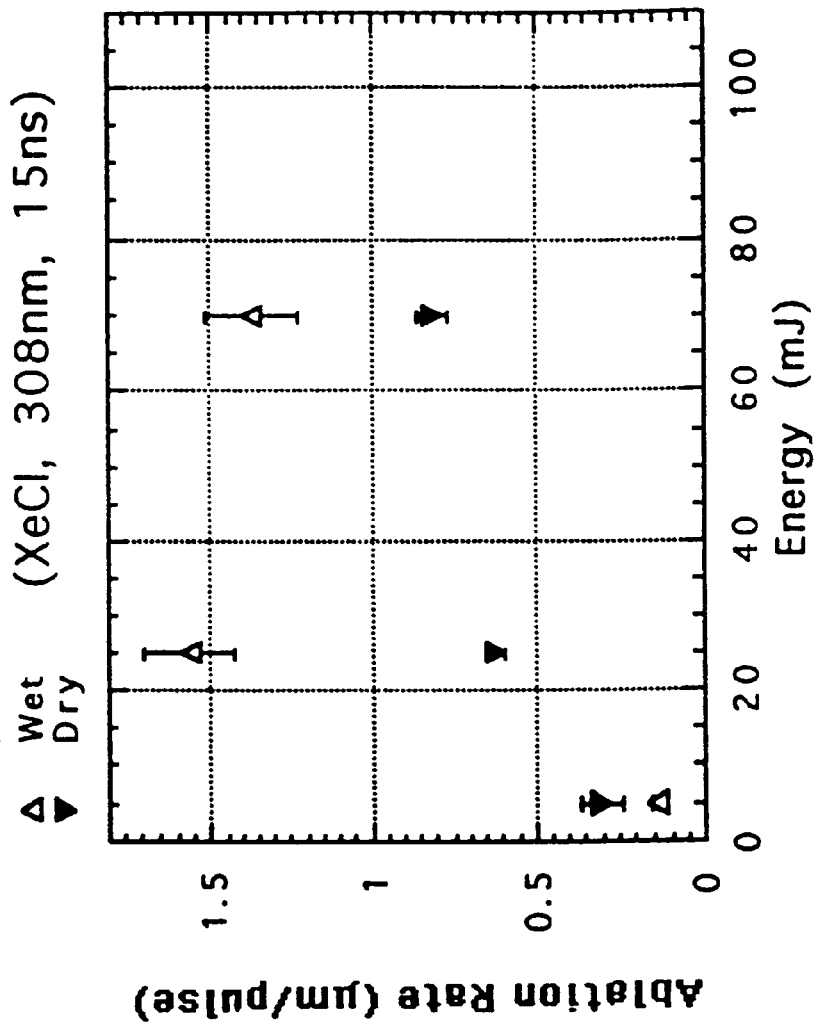
FIG. 3d, is a graphical representation of experimentally determined values of material removal rates in microns per pulse, plotted as a function of laser energy, of a 15 ns, 308 nm ultraviolet XeCl Excimer laser for exemplary fresh and dehydrated dentin materials.
Figure 3E:
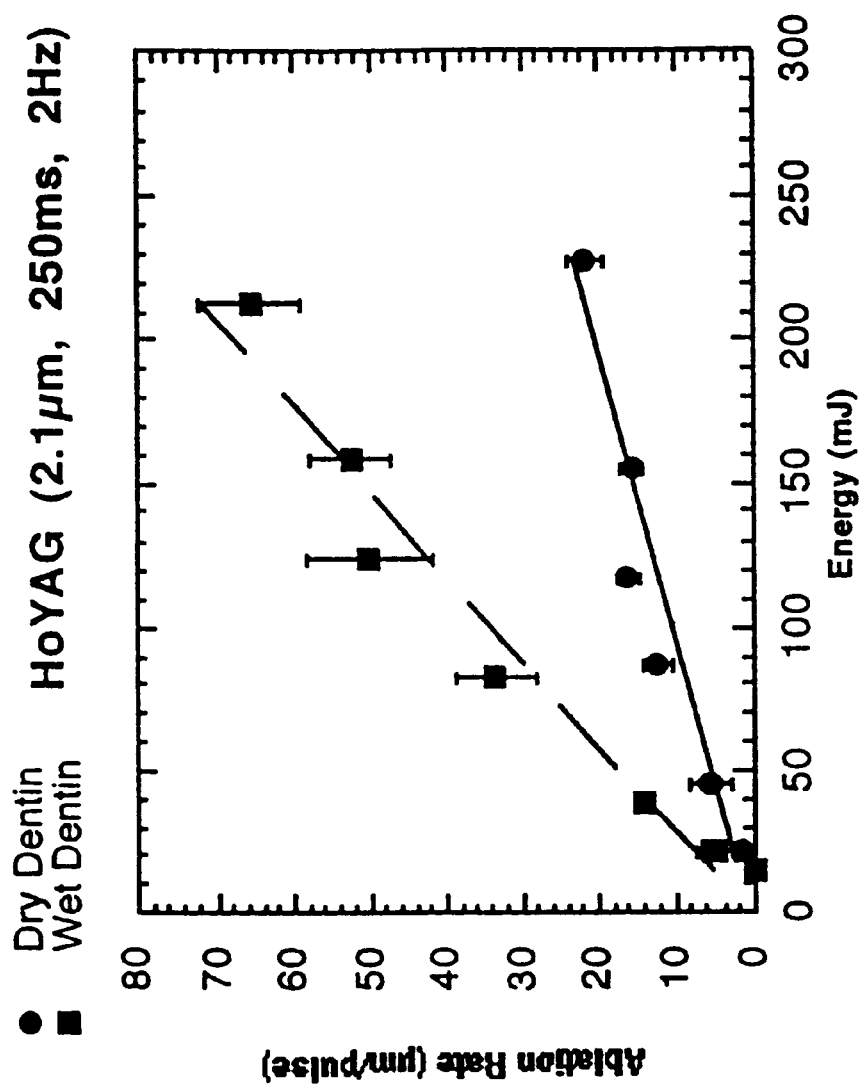
FIG. 3e is a graphical representation of experimentally determined values of material removal rates in microns per pulse, plotted as a function of laser energy, of a 250 µs, 2.1 µm infrared Holmium:YAG laser for exemplary fresh and dehydrated dentin materials.

An example of deeper penetrating wavelength is provided by FIG. 3d and FIG. 3e. Here, two plasma regimes are considered. FIG. 3d shows the XeCl system at 308 nm and 15 ns pulse duration. The beam intensity at the target is approximately $10^9$ W/cm$^2$ because of the relatively short pulse duration. The relatively deep penetration, on the order of 100 cm reduces the volumetric power density to about $10^7$ W/cm$^3$. On the other hand, the effect of relatively strong scattering in this ultraviolet range reduces the effective deposition depth and help raise the power density value back to $10^8$ W/cm$^3$ to $10^9$ W/cm$^3$. The results are similar to all those obtained with power densities of class 3 and remarkably similar to those shown in FIG. 3a for the one nanosecond Nd:YAG system (where power densities were on the order of $10^{10}$ W/cm$^3$ as well). As FIG. 3d and other data collected by the inventor show, there is a strong sensitivity to tissue type (e.g., 4 μm/pulse for dentin, and 1 μm/pulse for enamel at these $10^{10}$ W/cm$^3$ power density levels.) As FIG. 2e also shows, a distinctive ablation rate difference exists between high water content exemplary dentin material and between a dehydrated samples. Since in the case of hydrated dentin absorption is increased, volumetric power densities created at the surface also increase and plasma generation is enhanced and ablation rates are increased. As in the Nd:YAG ablation case, the scanning electron micrographs show a similar surface pattern which includes partial melting and surface cracks.

As a final example we consider yet another system of the relatively long pulse regime of 1 μs. In the exemplary system of FIG. 3e, a mid-infrared laser system of Ho:YAG emitting light in the normal mode of oscillation with macro pulse duration of 250 $\mu$s and wavelength of 2.1 $\mu$m. The power densities corresponding to the approximately 300 $\mu$m intermediate absorption depth of this 2.1 $\mu$m wavelength and 250 $\mu$s macro pulse are on the order of just below $10^7$ W/cm$^3$, and can be classified with the lower portion of class 3. This system macro pulse, however, consists of a train of about 20 micro pulses each of 1 $\mu$s pulse duration. The power density for these shorter micro pulses is thus on the order of almost $10^8$ W/cm$^3$, within the range of interaction class 3. The observed interaction are indeed inconsistent and strongly change as power densities are increased from below class 3 where little ablation and mostly heating, charring and cracking occur to above the class 3 threshold for plasma generation. When plasma is formed, ablation rate improves and increases linearly up to over 3 $\mu$m per pulse for the highest power densities tested for the water-contained samples. The inventor also noted the strong dependence on tissue type and water content (exemplary fresh dentin was ablated at rates 3 to 4 times higher than the exemplary dehydrated dentin, see FIG. 3e). Also noted was the typical class 3 ablated surface features which included some cracking melting and thermal loading.

Principles of Operation: Thermal Effects

Further advantages of the present invention are the control and influence that the operator is able to exert over thermal energy deposition in the tissue by the manipulation of plasma parameters. As was demonstrated above, the presence of plasma completely changes energy transmission and deposition in the material. As a consequence, the characteristic initial linear energy deposition and the subsequent reflection and dispersion of the incoming energy by the expanding plasma plume will ultimately be the most significant factors determining the amount of residual thermal energy left in the target material.

Figure 4A:
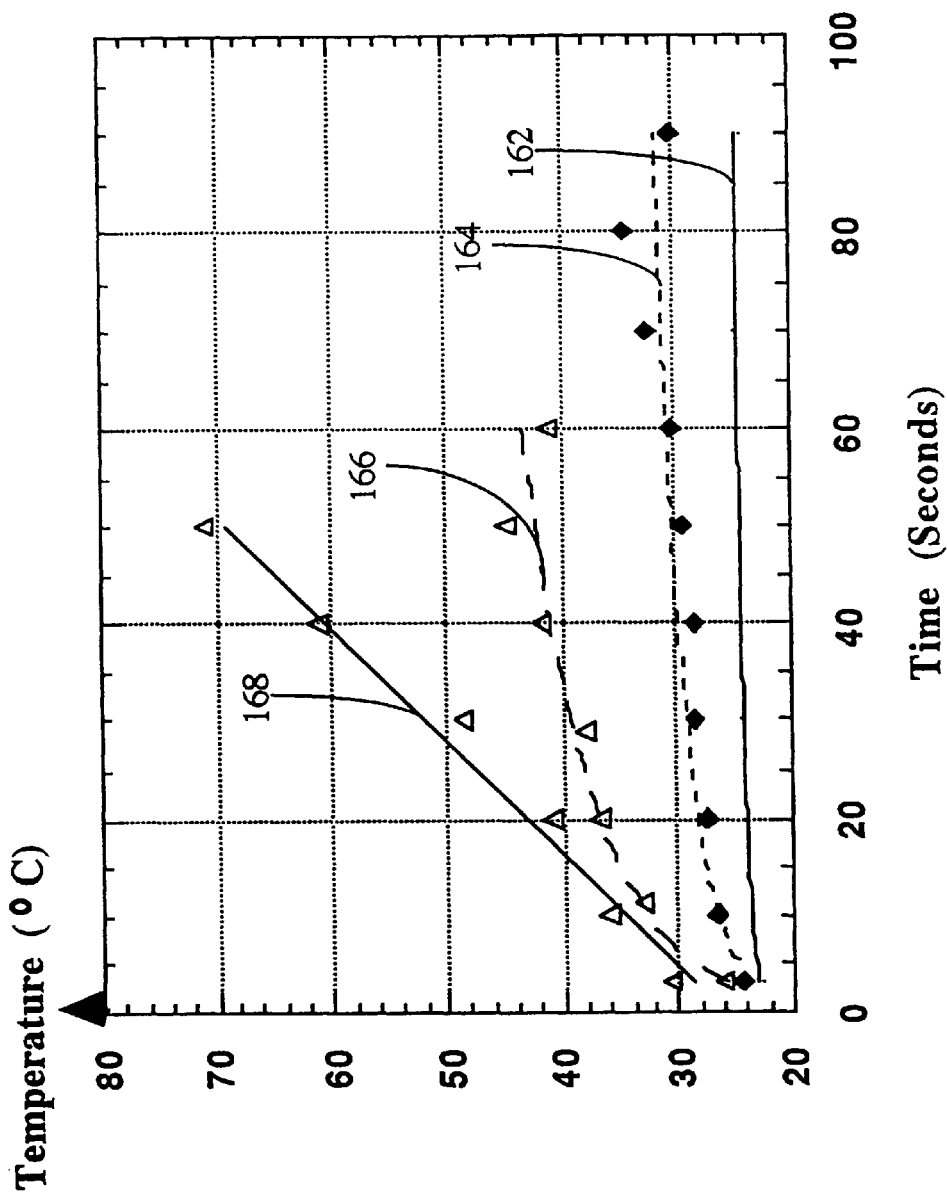
FIG. 4a, is a graphical representation of experimentally determined values of residual pulse heat, plotted as a function of time, for 350 fs laser pulses as compared to nanosecond laser pulses at a 10 Hertz repetition rate.
Figure 4B:
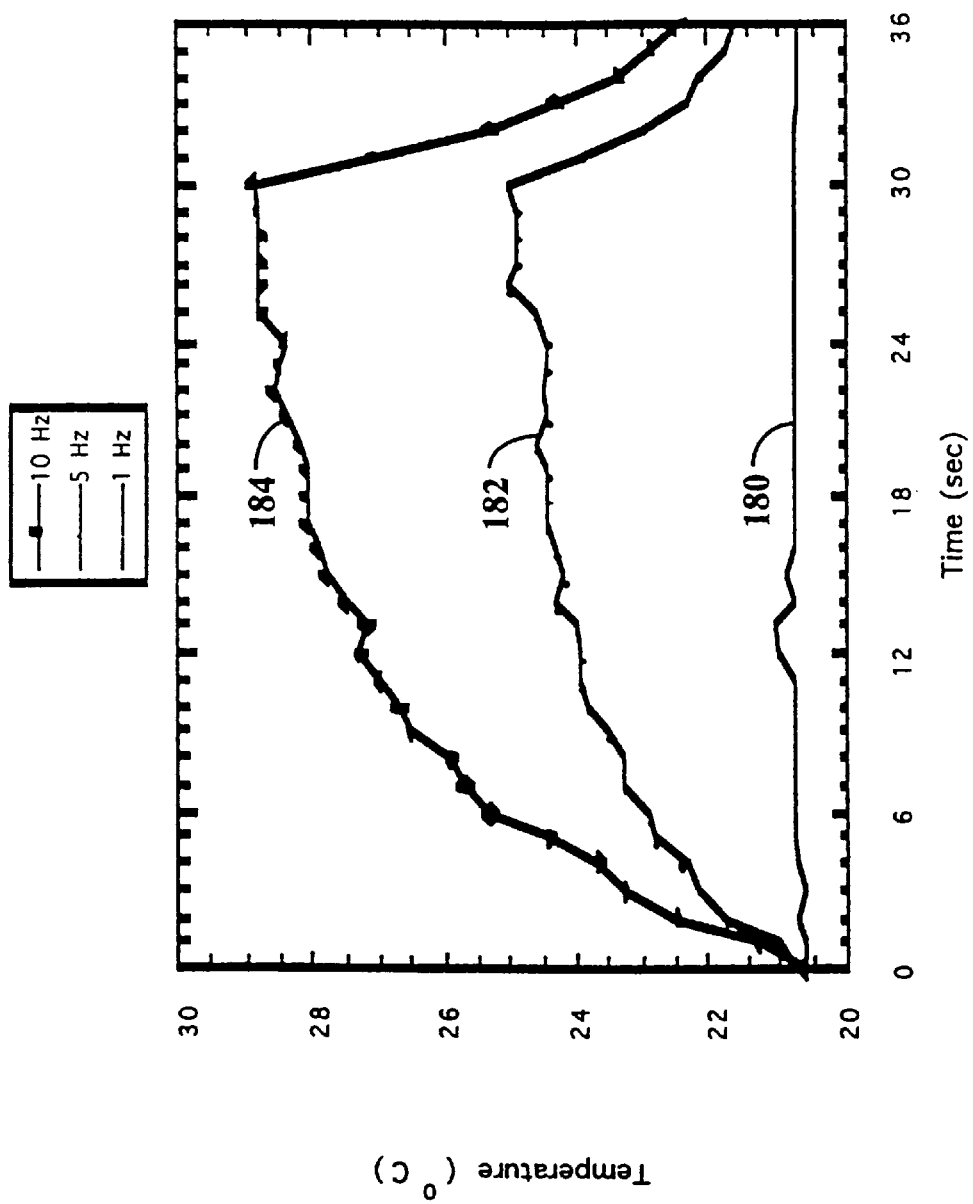
FIG. 4b, is a graphical representation of experimentally determined values of surface temperatures, plotted as a function of time, for 15 ns, 193 nm ultraviolet Excimer laser pulses for exemplary rabbit cornea material at 1, 5, and 10 Hertz repetition rate.

FIG. 4a and FIG. 4b illustrate the effect of the interplay between linear absorption and the onset of plasma on the residual temperature measured in exemplary dentin and rabbit cornea, respectively. FIG. 4a shows infrared camera temperature measurements corresponding to the ablation events depicted by FIG. 4a. Thus, FIG. 4a shows a graphical representation of thermographic measurements of the residual temperature increase, as a function of time, in exemplary dentin material processed with a laser having 1 nanosecond pulse duration and a fluence of 32 Joules/cm$^2$ 168, compared to an ultrashort pulse laser having pulse duration of about 350 femtoseconds at a fluence of 3 Joules/cm$^2$. Both pulse durations were delivered at 10 Hertz pulse repetition rates. As can be seen from FIG. 4a, the nanosecond laser system exhibits an 8° C. temperature differential over the femtosecond laser after only about 5 seconds operation. The residual temperature of the nanosecond laser continues to increase at a rate of about 1 degree per second. In contrast, the residual temperature of the femtosecond laser remains substantially within 2 to 3° C. of room temperature after application times in excess of one minute. The difference lies in the larger amount of energy needed by the longer pulse to initiate plasma, but also by the deeper optical energy deposition of the 1 ns system. With the longer pulses, linear propagation at this 1.05 $\mu$m pulse duration proceed until plasma generation occurs. Penetration depths are as deep as several centimeters and energy is spread much more evenly throughout the tooth, in significant violation of the inventor principle of high ratio of ablation depth to energy deposition depth as described above. This deeper lying energy is not removed by the ablative event and is then allowed to accumulate between consecutive pulses at the exemplary 10 pulses per second tested and result in the thermal build up observed for the 1 ns pulses in FIG. 4a.

For the 1 ns pulses, an increase in pulse fluence to 32 J/cm$^2$ yielded plasma and ablation. However, since a larger amount of volumetric power density was required to initiate the plasma, larger amount of energy is also left as residual energy in the 32 J/cm$^2$ pulse interaction with an exemplary dentin material. As a consequence, cumulative heat which is manifested in the surface temperature, is considerably larger. The case of the 1 nanosecond pulses at the relatively low absorption regime of the 1.05 $\mu$m light corresponds to class 2 in the classification described above.

A dramatically different situation is exhibited for the much shorter pulse of 350 femtosecond (also shown in FIG. 4a) Here, the class 1 interaction with high very high intensities of $10^{13}$ w/cm$^2$ lead to multiphoton ionization which was immediately followed by plasma generation. In the 350 fs case, ablation threshold for dentin is on the order of 0.5 J/cm2 and at the 3 J/cm2 interaction demonstrated by FIG. 4a, only 2 to 3° C. temperature increases are recorded even 60 to 80 seconds after the initiation of the interaction.

When the fluence of the 350 fs pulses is increased to 16 j/cm$^2$ the corresponding target temperature does increase to a 40° C. level as shown in curve 166 of FIG. 4a. This increase actually takes place due to plasma shielding where absorption of the excess pulse energy by the plasma raises its temperature and heats up the target material as well. On the other hand, lowering the 1 ns pulse energy by a half (to about 16 mJ) bring the fluence level to below threshold. Ablation ceases and, the material temperature (curve 164 in FIG. 4a) corresponds to linear absorption of the pulse energy by the very large penetration depth and volume. Consequently, the material temperature is significantly lower (about 30° C.).

The importance of the two mechanisms discussed above, namely, the role of the parity principle in ensuring removal of much of the deposited heat, along with the role played by the plasma as a means of controlling residual excess temperature, are further illustrated by FIG. 4b. Here the relatively low pulse fluence (0.25 J/cm$^2$) and pulse duration (15 ns) put the beam intensity at $10^7$ W/cm$^2$ or in class 2, as in the 1 ns interaction of FIG. 4a. However, since the beam wavelength in this case (193 nm) is highly absorbed in scattered by the exemplary rabbit cornea material, volumetric power density levels are significantly increased and result in rapid generation of seed electrons and plasma. As a consequence, the interaction is plasma mediated and shows the same interaction characteristics of the 350 fs pulses rather than the 1 nanosecond regime to which the pulse belongs. Similarly the temperature increase is only a few degrees and the heating shows the same temperature saturation behavior (or steady state behavior) for a time scale greater than about 10 seconds.

Figure 4C:
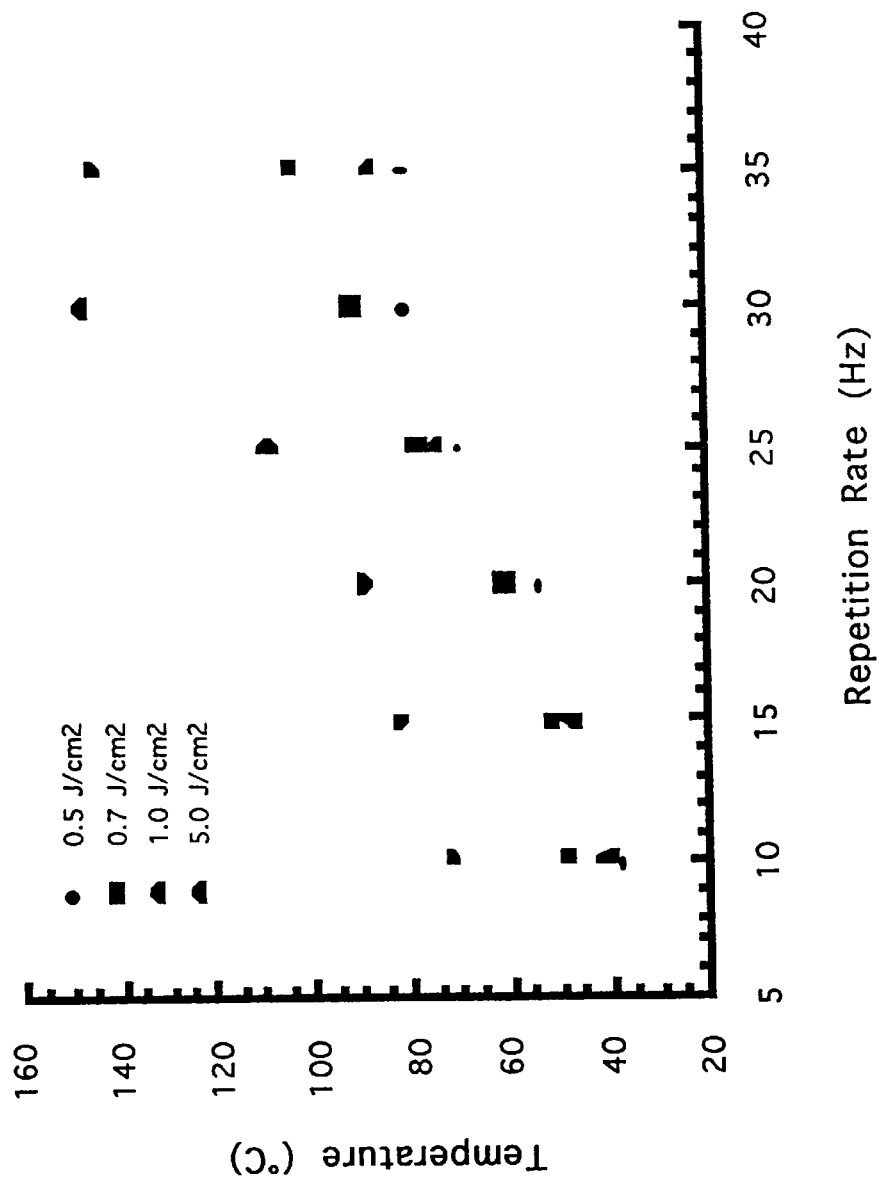
FIG. 4c, is a graphical representation of experimentally determined values of surface temperatures, plotted as a function of pulse repetition rates, for 15 ns, 308 nm ultraviolet Excimer laser pulses for exemplary dentin tissue material at 0.5, 0.7, 1.0, and 5.0 J/cm2 fluence levels.

The effect of plasma shielding is further illustrated by FIG. 4c for an exemplary 120 ns XeCl with 308 nm radiation. Here, as is clearly evident by the Figure, an increase in fluence level by 1,000% (from 0.5 J/cm$^2$ to 5.0 J/cm$^2$) results in a temperature increase of less than 70%. Such rejection of excess energy allows an increase of repetition rate by a factor of 7 with a temperature increase by less than a factor of 2. This aspect of the invention allows for the principle of high repletion rate operation which will be discussed below.

In conclusion, we see that the principle requiring high ablation depth to deposition depth ratio and the role of the physical ejection of much of the material with significantly elevated energy densities, are of critical importance to the practice of the present invention. Similarly, by reflecting and dispersing excess energy, plasma shielding too serve in all classes of power densities to minimize the amount of residual single pulse energy available for heating the material. Expressions of plasma effects and physical heat removal through ablation of much of the deposited energy are indeed seen in all three classes of source power density.

As the preceding discussion showed, the ablation rates of all three plasma classes are only on the order of a single micrometer per pulse. Thus, the application rate of about 1 to 10 pulses per second, found in most conventional and commercial lasers, is quite inadequate, because many material removal procedures require the removal of a large volumes of material in a relatively short period of time. As a result, despite the many advantages of the plasma-mediated interactions, the practical application of lasers within these three classes would normally remain unfeasible. In addition the inventor has realized that the application of high pulse repetition rates also serves to remove cumulative residual heat.

Principles of Operation: Heat Removal Through the Use of High Pulse Repetition Rate In accordance with practice of principles of the invention, these disadvantages are mitigated by the use of rapidly pulsed laser systems which can generate pulse repetition rates in the range of up to 100,000 pulses per second (100 kilohertz). Such high repetition rates are made practical because of two important factors: 1) the low residual thermal energy and low residual mechanical energy depositions which characterize the single pulse interaction in the practice of the present invention (this low residual energy deposition is a consequence of the inventor's principle of parity between single pulse energy deposition depth and depth of a single pulse ablation as discussed above); and 2) an intrinsic characteristic of sufficiently high pulse repetition rate which significantly help minimize cumulative heat deposition. The latter property will now be discussed below. With such high repetition rate systems, high material removal rates (up to several centimeter per second) can be achieved through the practice of the present invention, while maintaining the minimal collateral damage characteristics of a the single pulse interaction.

As explained above, high pulse repetition rate plays a crucial role in allowing the material processing method and apparatus as contemplated by the present invention to meet and even exceed material removal rate of conventional systems including mechanical instrument, chemical devices or conventional laser system. In addition, as was also pointed above, combined with low per-pulse material removal rates (for example, ablation depth on the order of a single micrometer pulse were discussed in the exemplary ablation of very short pulse lasers), very high precision can be achieved. This accuracy and precision in can be combined with the high removal rate only because the laser system can be electronically controlled by a feedback device which can stop an exemplary 1 KHz operation within a single pulse (i.e., within the 1 ms pulse-to-pulse separation). Such an exemplary system, thus, can remove 1 mm of material in one second to a tolerance on the order of 1 $\mu$m, an unprecedented combination of precision and speed.

Figure 5A:
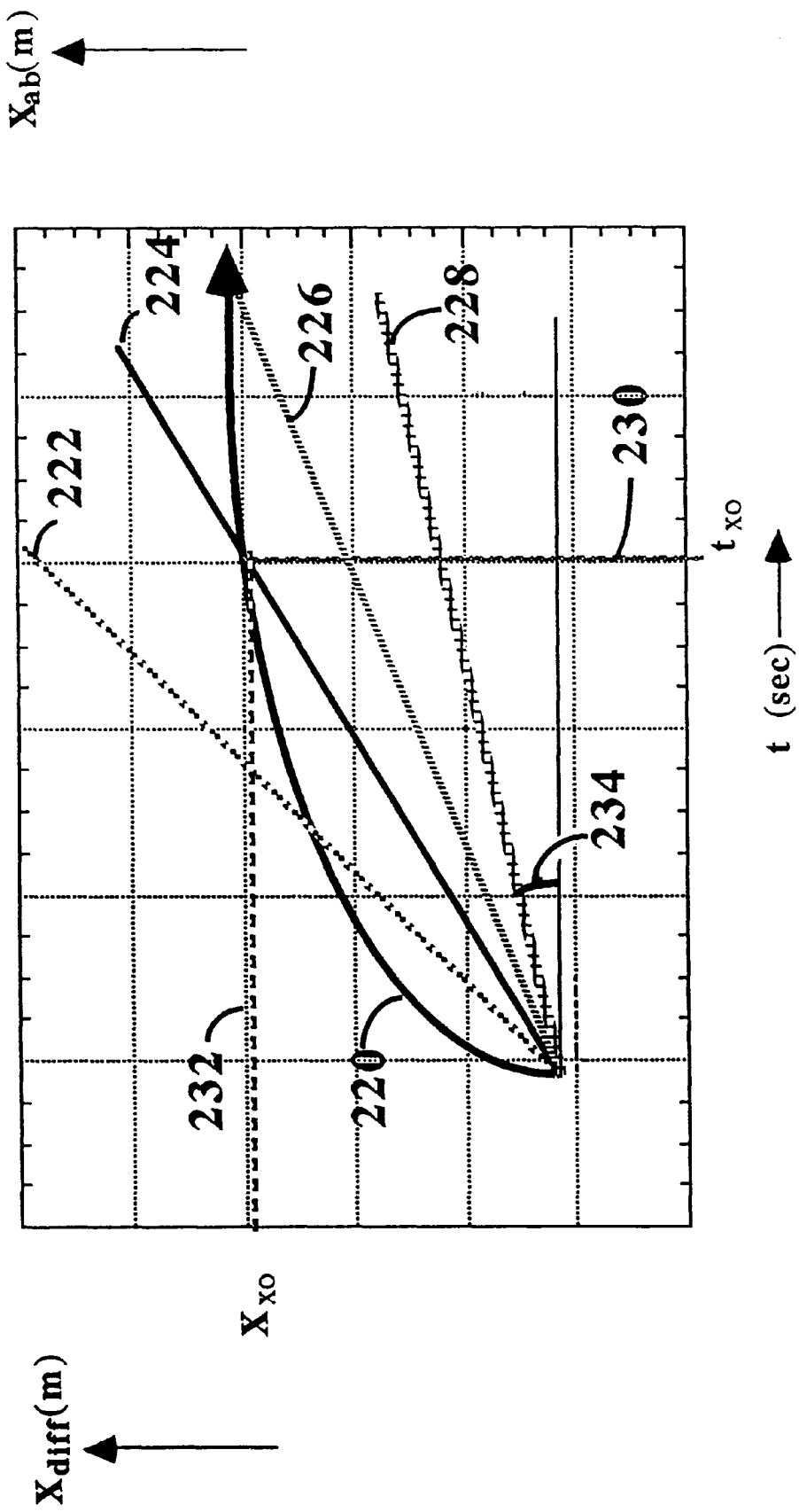
FIG. 5a, is a graphical representation of the evolution of the ablation front position and heat-diffusion front position as a function of time.

However, as the inventor recognized that high pulse repetition operation plays another unique and very important role in achieving a successful practice of the invention. Namely, high pulse repetition rates serve as an additional and very critical mechanism in removing residual heat accumulate by the total operation and application time ("ON" time) of the an ablation procedure. To understand this concept, which the inventor terms "self removal of cumulative heat by high pulse repetition rate operation", consider FIG. 5a. FIG. 5a the horizontal axis corresponds to the time axis, and the vertical axis correspond to distance. Curve 1 shows the location (depth) of the heat diffusion front as a function of time for an exemplary isotropic heat conduction parameters. Exact depth the heat has diffused to from the region of deposition is proportional to the square root of a proportionality parameter K and the time, t, $$X_{diff}=(K^{1/2}t^{1/2}) \quad (1)$$

The parameter K is proportional to the material thermal conductivity and is known as the "thermal diffusivity". It is equal to the "thermal conductivity" divided by the product of the material density and heat capacity. For an exemplary water or soft tissue can be roughly approximated as $10^{-6}$ m²/s. As can be seen from the FIG. 5a, the diffusion front 220, is a parabola curved about the time axis. It indicate very rapid initial heat diffusion which slows down very significantly as time progress.

The linear curves 222, 224, 226, and 228, in FIG. 5a, represent the position (or depth) of the ablation front below the initial surface. As can be seen from FIG. 5a, the ablation depth is directly proportional to time and can be described by the linear equation $$X_{abl}=(a_r v)t \quad (2)$$

Where the slope of the line, 5, is equal to $(a_r v)$, the product of $a_r$, the ablation rate per pulse and (nu) v, the pulse repetition rate. If, as we discussed above, a constant ablation rate per pulse of 1 $\mu$m/pulse is assumed, then the slope of the curves representing the ablation front of various pulse repetition rates are proportional to the pulse repetition rate. Thus, as can be seen from FIG. 5a, high pulse repetition rate will yield a steep slope and a low pulse repetition rate will yield a shallow line.

Significantly, FIG. 5a reveals a very important feature of the present invention. If the material processing system is allowed to operate long enough, the depth of the ablation front (or material removal) will ultimately surpass the depth of heat diffusion from the original pulses and the ablation itself will completely remove any residual heat that was deposited in the material by earlier pulse.

Since heat initially diffuses relatively rapidly, the heat from the most recent pulses will move faster than the ablation front and part of it will not be removed by later pulses if the system is stopped at some finite time. However, heat from earlier pulses will not diffuse as fast and will eventually be contained within a volume that will ultimately be completely removed by the system.

The point can be made clearer by considering an exemplary system operating at 1000 pulses per second for 3 second and to, for example curve 224 in FIG. 5a. In water from the first pulse to interact with the sample will diffuse a distance of 1 mm into the material at about 1 second. The ablation front, assuming ablation rates of 1 $\mu$m per pulse and 1000 pulses per second will cut 1 mm of material in 1 second as well. Thus, the point at which the ablation front overtakes the first-pulse heat diffusion front, designated in FIG. 5a as $X_{xo}$, and named by the inventor the "cross-over" depth", is approximately at 1 mm depth. The cross-over occurs approximately 1 second after the start of the interaction for an exemplary high water content tissue or material. This point in time is, consequently, named the "cross-over time" and is labeled $t_{xc}$.

If the exemplary system above is operated for 3 second, the heat from the first few pulses after 3 seconds of operation would be at some point $X_{diff}$ (3 seconds) along curve 220, but since 3 seconds is longer time than the 1 second $t_{xo}$, $X_{diff}$ (3 seconds) will be a shorter distance that the ablation front at t=3 sec as indicated by the fact that the position of curve 224 is higher than that of curve 226 for t>txo. Those skilled in the art will readily recognize that the heat diffusion front due to heat deposited by ALL pulses originated within the first 2 seconds of the procedure will be at some location $X_{diff}$ on curve 220 beyond $t_{xo}$, which will also be below the ablation front depth. This condition, thus indicate that all the volume of the material heated by pulses pulse number 1 to pulse number 2000 was removed by the ablation.

The situation is different for the last 1000 pulses in our exemplary 1000 Hz system. These pulses are characterized by the fact that the time remaining in the interaction is shorter than the time necessary for the ablation front to overtake their thermal diffusion position, $T_{xo}$. An exemplary pulse interacting with the material a time $t_{lp}$ before the source ceases operation, will have its heat diffuse to a position $X_{lp}$, which is deeper than depth of material removed by the (n $t_{lp}$) pulses left within the time interval $t_{lp}$ before the source ceases operation.

As FIG. 5a shows, however, even these last few pulses have some of their residual heat removed by the subsequent pulses. Clearly, pulses just behind pulse 2000 will have most of their heat removed by the subsequent, nearly 1000 pulses, while pulse number 3000 and the last few pulses in the sequence—will have none or very little of their residual heat removed by subsequent pulses. Interestingly, the inventor also recognized that the fraction of the deposited heat left by each one of the last 1000 pulses in the exemplary 1000 Hz system, is proportional to the ratio of the distance between the depth of thermal diffusion and the position of the ablation front (i.e., the distance between position $X_{diff}$, given by curve 220 minus the position Xab given by curve 224, ($X_{diff}$–Xab)), and the total diffusion depth, $X_{diff}$. Furthermore, the total amount of cumulative heat not ablated by the exemplary laser system is proportional to the area bounded between curve 220 and curve 224 to the left of $t_{xo}$.

FIG. 5a also shows that if for high pulse repetition a steeper slope will mean that $t_{xo}$ occurs earlier and smaller proportion (in comparison with the total amount of cumulative heat deposited in the material will be left. For very slow ablation rate, on the other hand, txo may not occur in pratical times (for example t<5 second, a reasonable upper limit time scale for an exemplary dental application system), and only small potion of the deposited heat will be removed by the ablation front as indicated by curve 228 in FIG. 5a. This situation invariably occurs with the low pulse repetition rate of conventional surgical and material processing system. The ability to operate in the high pulse repetition regime and to ablatively remove much of the residual heat thus represent a major advantage of the present invention over conventional tools and conventional laser system. The ability to remove most of the heat was also confirmed by Scanning electron micrographs studies and by infrared Thermographic measurement of ablation temperatures as discussed below.

Figure 5B:
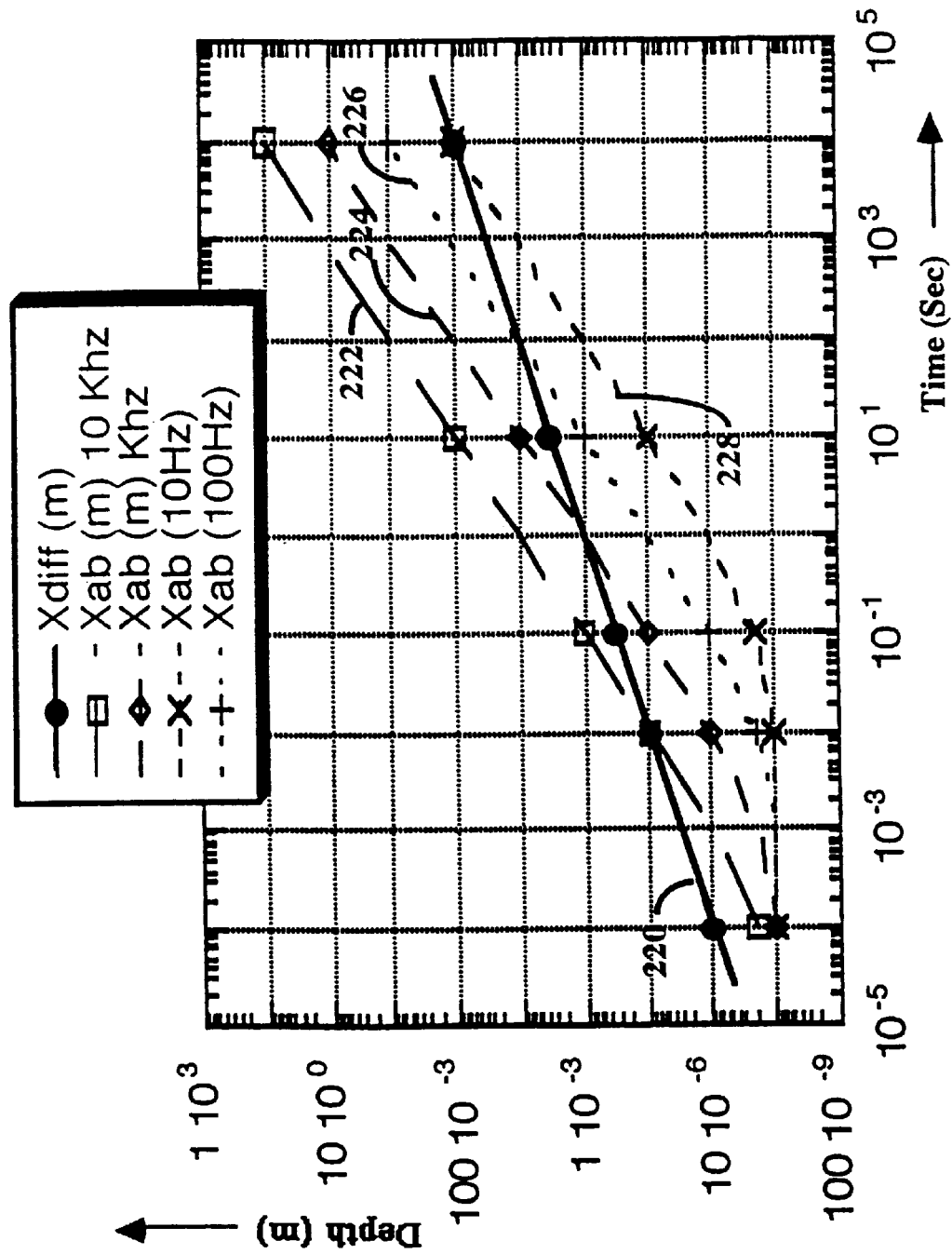
FIG. 5b, is a graphical, log—log representation of the evolution of the ablation front position and heat-diffusion front position as a function of time for water-like system being ablated at an assumed rate of 1 µm per pulse, by a system operating at 10, 100, 1000, and 10000 Hertz pulse repetition rates.

FIG. 5b reproduces the concept of FIG. 5a for actual computed values off our exemplary systems operating at 4 different repetition rates ablating and depositing heat in a water-like system. In order to illustrate the effects described above over a large range of time logarithmic scales were used and, consequently, the diffusion curve 220 appear linear and the ablation front appear curved. Non the lest the cross over point can be clearly identified. FIG. 5b clearly shows that the ablation front position of pulse repetition rate of 100 Hz does not reach the diffusion front position until 100 second after start of interaction. The 100 second time scale is clearly too long and not a practical time scale for almost all operations or procedures. Yet in terms of operating pulse repetition rate regimes of conventional laser sources, 100 Hz is usually considered very high and outside of safe operating regime due to considerable thermal loading and risk of collateral damage.

Figure 5C:
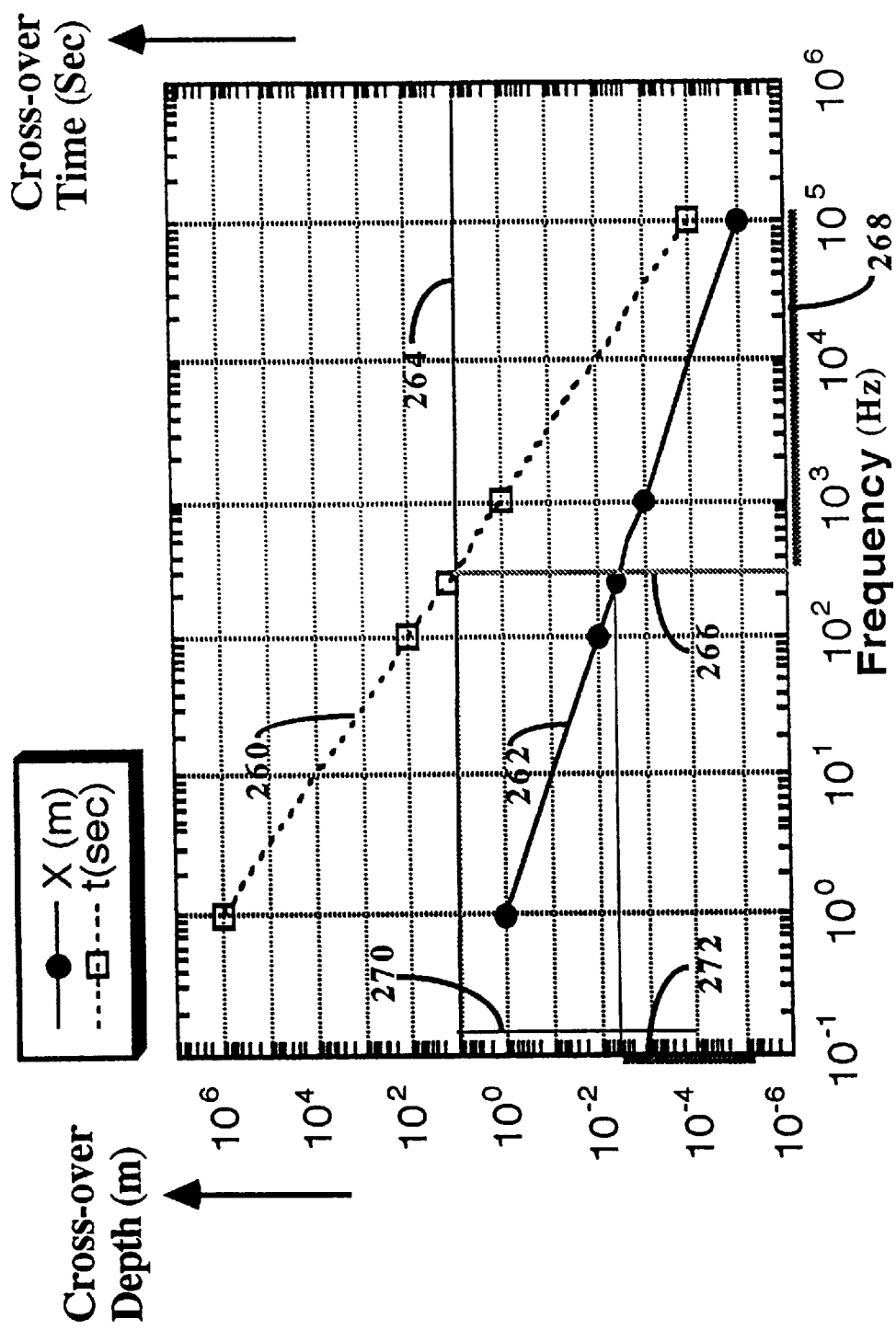
FIG. 5c, is a graphical, log—log representation of the cross-over depths and cross-over times, i.e., the depth and time at which the ablation front surpass the thermal diffusion front, as a function of the source pulse repetition rates.

To take advantage of the total cumulative heat removal of high repetition rate system one would want to operate at pulse repetition rates that bring one quickly to the regime beyond the Cross over operating point. The Cross-over times and depths can be given in terms of the thermal diffusivity and the ablation rate and expressed as a function of the source pulse repetition rates n. FIG. 5c shows the calculated values for both the cross-over time and cross-over distance as a function of source pulse repetition rate (or frequency of pulses in Hz). The values were calculated, again, assuming a water-like media and an assumed ablation rate of about 1 $\mu$m per pulse. In order to fit in one figure the behavior for a wide range of pulse repetition rates (ranging from 0.1 Hz to one megahertz) the graphs were plotted on a logarithmic-logarithmic scale. The x-axis corresponds to pulse repetition rates (or source frequency, in Hertz), and the y-axis is shared by the cross over depths (in meters) and the cross-over times (in seconds). Both share the same numerical values and range from $10^{-6}$ to $10^6$. The cross over times, $t_{xo}$, are given as a function of source frequency (or pulse repetition rates) and can be found on the linear curve 260, while the crossover depths, $X_{xo}$, for a given pulse repetition rate can be found on the linear curve 262. Practical procedure length of time require that a procedure will be limited to less than about ten second of a continuous application duration. This upper limit for procedure time which is indicated by the line 264.

The ten second maximum application time implies that material removal procedures (for the exemplary system considered) carried out at pulse repetition rates lower than about 300 Hz will never cross-over and the ablation front will never surpass the initial diffusion front. The approximate limit at 300 Hz that corresponds to the ten second procedure limit is indicated by the vertical line 266.

The 300 Hz pulse repetition rate bench-mark is important in cases were large volume removal is intended. As FIG. 5c shows, this pulse repetition rate implies a cross-over depth of about 3 mm. For any volume with depth larger than 3 mm, several exposure will have to be applied, no complete heat removal of earlier pulse train is possible, and larger fraction of the incident energy will remain as residual heat. As a consequence, larger amount of heat will remain in the target material with the possibility of generating collateral damage. However, if only small volume are targeted for removal (i.e., small in the sense that the desired removal depth is shorter than the cross-over depth), then lower frequency are acceptable since the total number of interacting pulses is, (by the definition of the procedure's goal), limited.

The duration of plasma plume (on the order of a few microsecond) and the need to avoid pulse-to-pulse plasma shielding, among other things, thus dictate an operating pulse repetition rate regime between about 300 Hz and about 100,000 Hz. This range of pulse repetition rates is indicated on FIG. 5c by the thick dotted line 268.

The range of about 300 Hz to about 100,000 Hz of pulse repetition rates defines the practical pulse repetition rates that should be applied for large volume removal large in the sense that the desired removal depth is larger than the cross-over depth. For this range the cross-over times range 270, is from about ten seconds to about 100 µs, respectively. The cross over depths curve 262 defines the range of cross-over depths corresponding to this pulse repetition rate range. The cross-over depths range 272, stretches from approximately 3 mm at 300 Hz to about 10 µm at 100,000 Hz.

Finally, in considering the practical application of the present invention, one must recognize that while high pulse repetition rates ablate much of the cumulative heat left in the tissue, very high repetition rate also translate to very rapid material removal rates. Application of 100 KHz system for one second will result in 10 cm of material being removed. To avoid removal rates that are exceedingly fast, exposure time would have to be limited (by adjusting a controller) to, for example 100 µs or 5 ms intervals so that removal will be automatically stop at 50 to 500 µm and allow the operator to reapply the procedure to achieve incrementally larger volume removal.

Figure 5D:
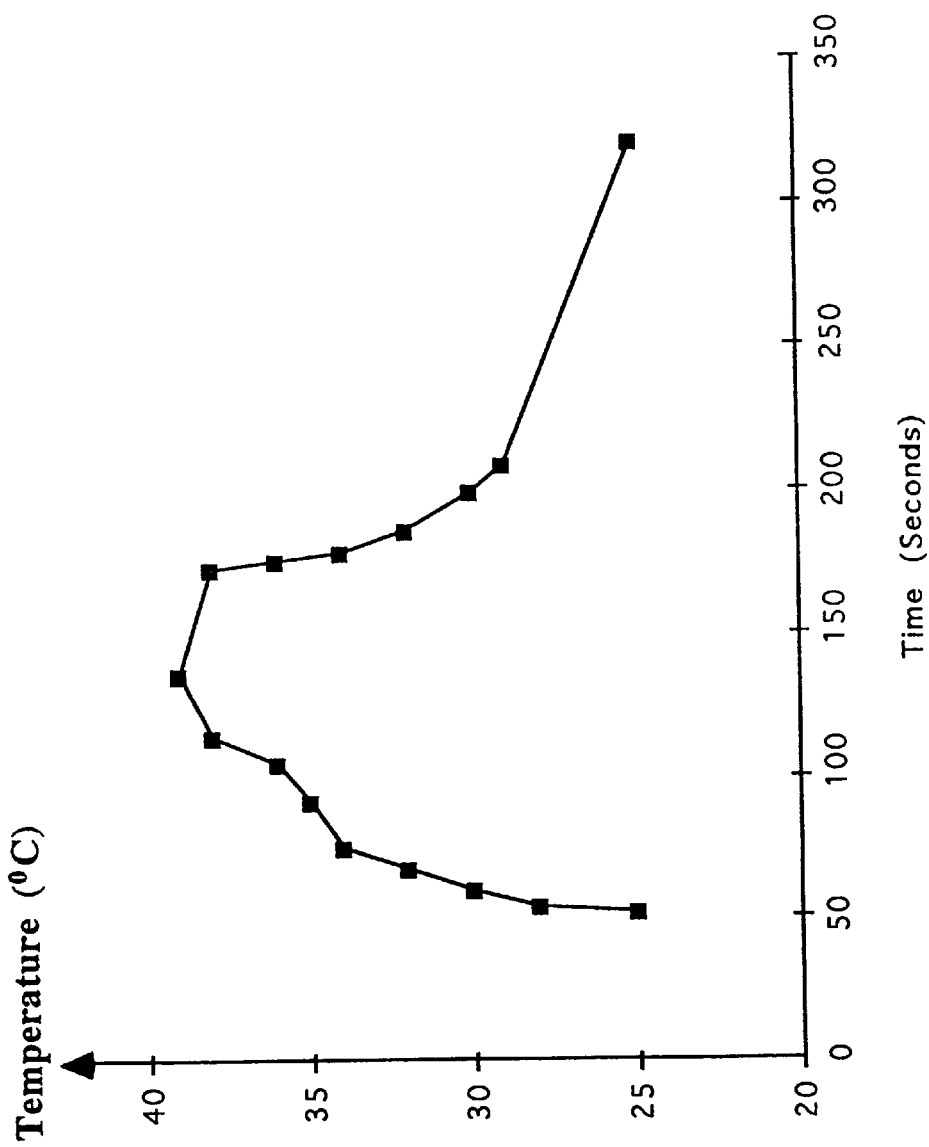
FIG. 5d, is a graphical representation of experimentally determined values of residual pulse heat, plotted as a function of time, for 600 fs laser pulses operating at a 1000 Hertz repetition rate.

FIG. 5d shows an experimental confirmation of the minimal temperature increases produced by an exemplary 1000 Hz system. The figure depicts a graphical representation of residual temperature as a function of time of a laser operating in accordance with the invention at a repetition rate of 1000 Hertz. The pulse duration is 60 femtoseconds at a fluence of about 2.0 Joules/cm was used. As can be seen from FIG. 5d, the residual temperature increases only slowly to about five degrees 8° C. over room ambient after 20 seconds application time and to a maximum increase of 14° C. after 90 seconds of application time.

A general estimate of the relative amount of heat removed due to the principle of operation concerning high pulse repetition rate ablation of earlier pulses residual heat, can be obtained from the following example. If the exemplary 1000 Hz, system considered above, operated with an exemplary 3 mJ/pulse to remove approximately 1 µm of material with each pulse, is used to drill through 5 mm of an exemplary dentin material, we need only consider the heat due to pulses applied $t_{xo}$ seconds before the end of operation (see FIG. 5a). $t_{xo}$ is approximately 1 second for the exemplary system considered, and at 1000 Hz, only the last 1000 pulses need be considered. The total amount of energy emerging from the exemplary 1000 pulses of the system considering is thus 3 Joules. A reasonable percentage of this incident energy that is eventually coupled to the material as residual heat can be estimated at 10 percent. Thus the total amount of energy couple after the drilling of 5 mm exemplary dentin is approximately 300 mJ. As was discussed above in connection to FIG. 5a, even out of this remaining 300 mJ energy only a fraction, proportional to the ratio between the area bounded between curve 1 and curve 3 to the left of $t_{xo}$ and the total area under curve 1 and to the left of $t_{xo}$, is left actually left in the tissue. From FIG. 5a this ration can be roughly estimated at about one third. Thus, only about 100 mJ of energy will remain as a residual heat in the exemplary dentin. This compared to (3 mJ/pulse) * (5000 pulses)=15 Joules actually applied by the beam for the actual drilling of the entire 5 mm depth.

For comparison with an exemplary conventional laser system, a 2.94 µm wavelength, Er:YAG operating at an exemplary 10 Hz with, 100 mJ per pulse incident energy, packed into 250 µs long pulse each capable of removing 30 µm with each pulse. To drill through 5000 mm of dentin, approximately 170 pulses are needed which, at 100 mJ/p correspond to 17 Joule of total energy. Again, using the same 10 percent coupling ratio, an estimated 1.7 Joule is estimated to remain in the tissue as residual heat energy. This amount of energy is 17 times as large as that of the exemplary 1000 Hz system. Indeed, infrared thermography and scanning electron micrographs clearly shows charring, cracking and carbonization for ablation of dentin with an exemplary 10 Hz Er:YAG system.

Thus since the total amount of energy applied to the material by this entire exemplary procedure (15 Joules by the exemplary 1000 Hz system and 17 Joules by the Er:YAG system) and since the residual thermal energy left in the tissue was assumed to be the same in both system (10 percent of incident), is almost the same, the example above serve to dramatically illustrate that it is the high repetition rate system ability to ablate and remove its own heat, that make an important contribution in limiting the amount of cumulative residual energy and limiting collateral damage due to that residual thermal energy. Again, these conclusions are confirmed by infrared temperature measurements of FIG. 5d above compared to the several hundreds of degrees Celsius measured for 9 Hz ablation of an exemplary Er:YAG system, and by surface examination of the ablated crater (including scanning electron micrographs) clearly showing damage free surfaces for the 1000 Hz system in contrast to the tremendous charring, burning and cracking of the Er:YAG system.

For even higher pulse repetition rates, for example 10 KHz $t_{xo}$ is about 0.01 second so that only approximately the last 100 pulses need be considered. At the maximum pulse repetition rate contemplated by the invention, namely 100 KHz, t xo is about $10^{-4}$ seconds and thus only approximately the last ten pulses effect tissue cumulative heat.

The discussion above considered water-like material with K approximated at about $10^{-6}$ m$^2$/s. However, in the practice of the invention in material processing, however, a large number of exemplary target materials may be contemplated. In general these may be divided into two broad categories of dielectric and conductors. The thermal conductivity of dielectric is similar to that of water. Conductors thermal conductivity can be higher by about three orders of magnitudes. If, for example, an exemplary aluminum is considered, the time required by the thermal diffusion front to reach a depth of 1 mm may be estimated at about 0.001 second. In such instances, even if the ablation rate per pulse is maintained at about 1 µm/pulse (and in general the ablation rate in metals are often 2–3 time lower than dielectric, i.e., 0.3–0.5 µm/pulse) and even at the highest pulse repetition rates if 100 KHz, the ablation front will be able to catch up with the thermal diffusion front only at about Xco of 10 mm and txo of about 10 seconds. With 10 seconds of 100,000 Hz, one million pulses will constitute the residual cumulative heat pool (before ablation begins to remove additional pulses energy. (e.g., pulses 1000,001 to 1,500,000). Thus too much heat will be deposited in the material to make the high repetition rate removal of heat, impractical. A better approach for the conductor case would be to take advantage of it's fast thermal diffusion which allow the ablated material to quickly rid itself of the excess heat, by either using a target consisting of a large thermal mass to dissipate the heat, or having the a heat sink in thermal contact with the target conductor material.

As the discussion above showed, for dielectric, the ablation processes as contemplated by the practice of the present invention, result in highly localize, self-terminating, shallow energy depositions. The inventor has determined that by manipulating absorption and scattering characteristics, the pulse electromagnetic energy source can used in the practice of the present invention, will allow per-pulse removal of only a thin layer of material "Thin" is measured in comparison to the total depth of desired material removal, which, for a typical removal depths required for an exemplary hard dental tissue procedure will be typically on the order of 1 micrometer, and for a typical depths required for microchip processing may be one tens of that (or about 100 nanometer). Thus, varying the number of pulses provides a means of controlling the volume of material removed to within a single pulse precision.

For example, if the laser systems were contemplated as substituting for a paradigm mechanical dental drill, the system would be required to drill dental tissue at a rate approximating the 300 micron per second removal rate of the mechanical drill. From the discussion of plasma-mediated pulse ablation rates, in connection with FIGS. 3a through 3e, above, it is clear that a 300 micron per second removal rate can be easily achieved by operating the laser system of the invention at a repetition rate of between about 100 to 300 pulses per second (100–300 Hertz). In fact, in view of the discussion above it is clear that with the capabilities of the a laser system contemplated by the invention, much larger removal rates are possible and, indeed, may be advisable.

Characteristically, conventional and prior art laser systems are unable to operate at such high repetition rates because of the high degree of residual heat and significant thermal loading in the ablation area. In these systems, as was discussed above, linear optical propagation allows deep penetration into the target material and significant heat remains in deeper layer of target and is not removed by the ablation event. Rapid operation of these systems results in very significant accumulation of heat.

Lasers conventionally used for the removal of hard and/or soft tissue operate in the infrared region of the electromagnetic spectrum, have pulse duration in the range of about 10 nanoseconds to in excess of 350 microseconds, and exhibit characteristic removal rates of exemplary dentin-type material of about 20 to 50 microns per pulse. IR lasers are additionally known to cause objectionable charring of target material, such as exemplary dentin, when operated at pulse repetition rates as low as 2 to 3 Hertz. Thus, it will be apparent that conventional pulsed IR systems are only capable of effecting material removal at a maximum rate of about 150 microns per second. The addition of air and/or water cooling mitigates the excessive heat problem but complicates the system operation. Even with cooling removal rates, such systems are limited to about 300–400 $\mu$m per second, well below the 700 $\mu$m per second observed with the mechanical drill.

Thus, it will be apparent that a laser operating in accordance with practice of the invention is able to comprise a material removal system that results in minimal thermal loading in the ablation target area and thus can tolerate pulse repetition rates as high as 100,000 Hertz, without the need for any type of additional target cooling mechanism, for periods of time substantial enough to effect volume material removal. It is also apparent that such a system cannot be realized by conventional laser systems operating with low ablation-to-deposition depths ratio, and/or low pulse repetition rates, if any significant volume removal or modification is required.

In summary, high ablation-to-deposition depth ratio, operating at high repetition rates have several advantages over conventional systems. As energy coupled to the material decreases and is confined to shallow deposition zone, the material removal system of the invention becomes more efficient. Minimal collateral damage occurs because of the high ablation-to-energy deposition ratio ensures residual energy removal instead of residual energy build up which leads to collateral damage. The ablated material carries away a large fraction of the energy deposited by the laser. Indeed, the minimal collateral damage and low residual thermal energy left in the material due to the single pulse interaction, combined with the inherent additional energy removal associated with the high pulse repetition rate of the laser systems in accordance with the invention, allow pulse repetition rates far in excess of those achievable with conventional systems, thereby allowing substantially greater bulk material removal rates.

Finally, since the invention relies on high pulse repetition rate for large volume material removal, the mass of the material removed by a single pulse as practiced by the present invention is very small, (in many cases which can be conceived in practice "very small" means on the order of single micron), very little recoil momentum or mechanical transients will be generated by each single pulse. Since mechanical transients travel at the speed of sound (or faster, in the case of shock waves) pulse-to-pulse accumulation at the repetition rates considered by the invention will not be significant and will not effect the remaining material adversely.

Principles of Operation: Use of Doping Agents and Selective Marking of Targeted Regions Within the Material As was discussed above, a key to the practice of the present invention is meeting the parity requirement for equivalence between the depths of deposition and ablation. As was also shown above, one class of interactions that fulfill this requirement include the ablation processes which follow the generation of plasma, because plasma characteristics ensure generation of high power densities within very shallow deposition depths.

In many instances the material/beam parameters are such that this requirement is fulfilled naturally. However, As part of the contemplation of the present invention, it is possible to convert systems with relatively deep optical penetration and/or lower power pulse energy, and/or longer pulse duration into efficient plasma-mediated material processor. The principle of operation for converting a linearly absorption system into a system that meet the criteria for the principle of parity can be understood with the aid of FIG. 6a.

Figure 6A:
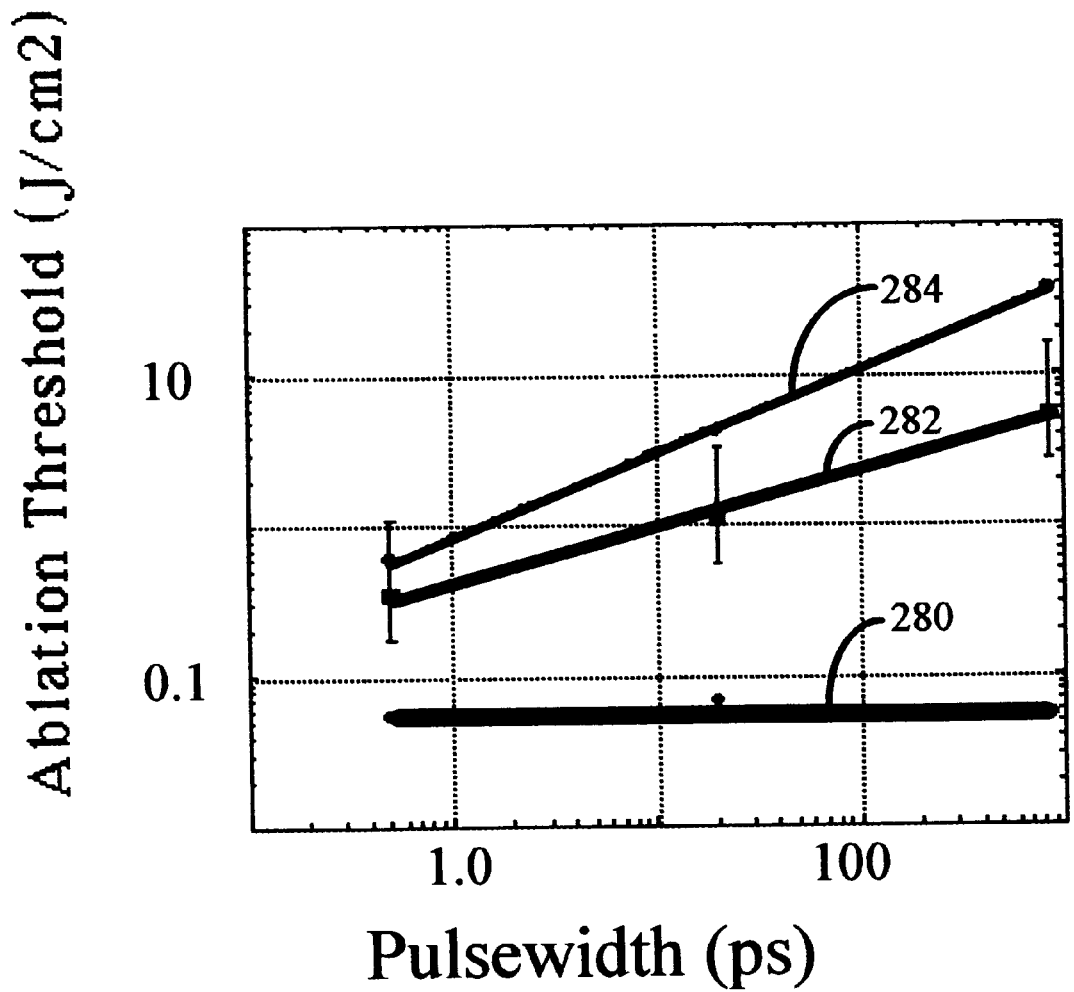
FIG. 6a, is a graphical representation of experimentally determined values of ablation thresholds plotted as a function of pulse duration for materials having different absorption characteristics, depicting the dependence of ablation threshold values on pulse duration for weakly absorbing material, and the lack of dependence of ablation threshold of pulse duration for material with strong absorption characteristics.

FIG. 6a illustrates the role that a doping agent with high absorption coefficient can play in allowing plasma generation at lower power densities. The figure shows the ablation threshold fluence (in J per cm$^2$) for three types of absorbers. The upper line 284, corresponds to week absorber with characteristics absorption coefficient of 0.01/cm. The intermediate line 282 correspond to absorption coefficient of 22/cm and the lower curve 280, corresponds to a very strong absorber with absorption coefficient of 1000/cm or penetration depth of about 10 $\mu$m.

As both the curve corresponding to a weak absorption 284, and the curve corresponding to intermediate absorption 282, show, since plasma mediated ablation depends on achieving high power densities and the subsequent generation of sufficiently high electron density in the plasma, greater fluence is required to achieve ablation threshold if the pulse duration is longer. On the other hand, the FIG. 6a also shows that if a strong absorber like the one represented by the curve 280 is used (for example a doping agent or a naturally colored and highly absorbing target), the ablation threshold is essentially uniform and independent of the pulse duration. In the strong absorber case, concentration of photons in shallow deposition layer and high power density are achieved for all pulse duration and ablation naturally follows.

If the material absorption characteristics are such that high energy concentrations and energy densities are generated, either multiphoton ionization or thermal ionization will quickly initiate seed electrons followed by an electron avalanche and plasma-mediated processes. As was already explained above, once plasma is formed, ablation characteristics are relatively uniform. This effect is illustrated by the lower curve of FIG. 6a. This curve corresponds to ablation threshold of a highly absorbing material.

As stated above, the upper two curves (284 and 282) correspond to a material which is relatively transparent to the 1.054 $\mu$m radiation of the exemplary laser pulse tested. Here long pulse duration combined with deep beam penetration results in relatively low volumetric energy densities and does not yield plasma-mediated interaction. Instead, heating and vaporization are the main ablation mechanism. These damage processes require much larger total energies over the much larger volume of interaction and thus translate into higher damage threshold as shown in FIG. 6a.

On the other hand, at shorter pulse duration (<10 ps), even with relatively transparent target materials, the beam volumetric power densities become high due to the very short time duration of the pulse which concentrates the same amount of energy in a much shorter length of time. The result is volumetric power densities sufficient to generate plasma and interaction characteristics (in this case ablation threshold) which corresponds to that of the naturally occurring highly absorbing materials.

Figure 6B:
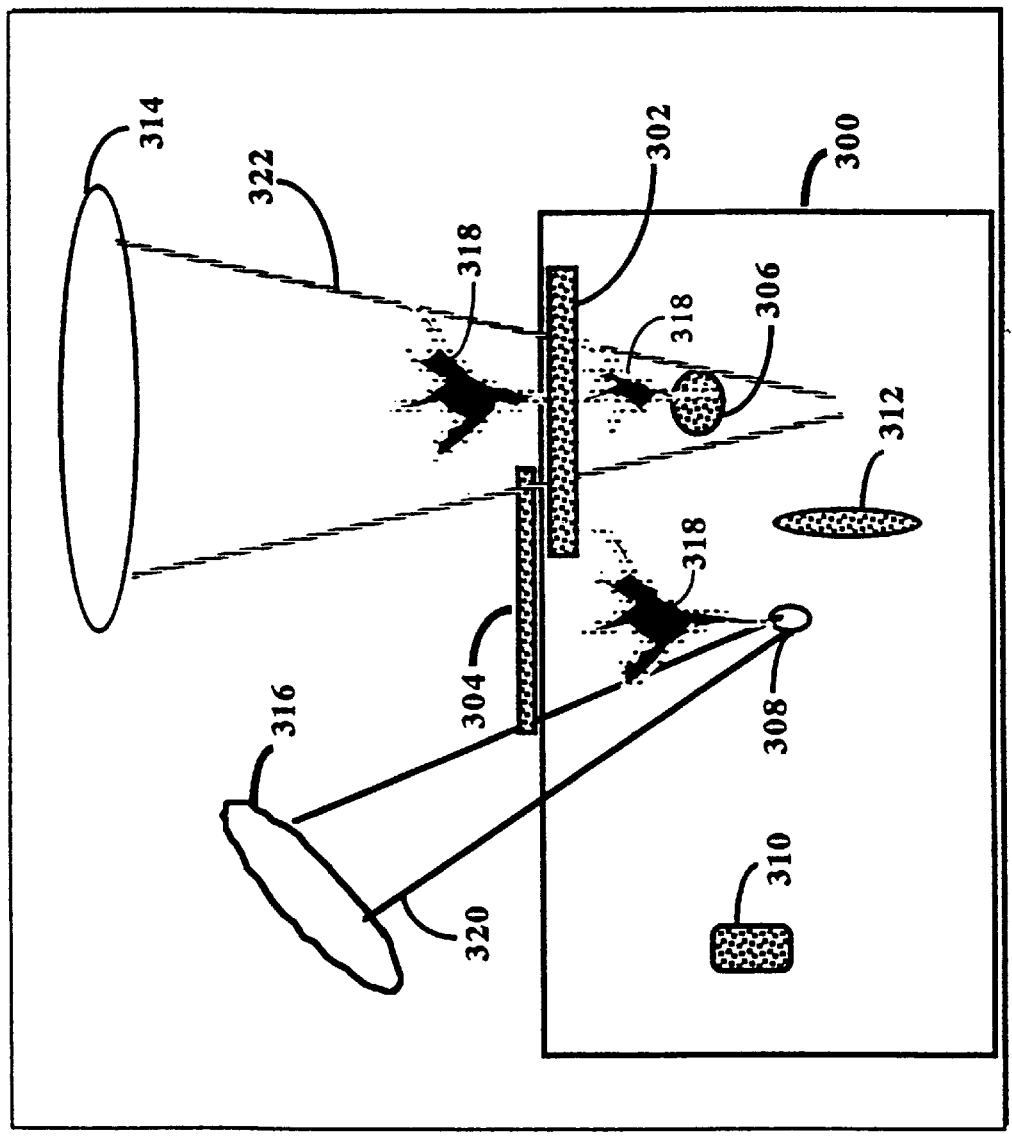
FIG. 6b, is a simplified block level schematic diagram of various selective, target-specific interaction configurations with two-dimensional surface and/or three-dimensional volume marked targeted material.

The desired conversion, as contemplated by the present invention, of a system with a naturally occurring high penetration depth into a system of with very shallow depth of energy deposition which easily fulfill the parity requirement can be made both time and space dependent and can be achieved in several different ways:

i) Through the deposition of an absorbing agent on top of the material surface, or within a predetermined thickness layer of within the material surface prior to initiation of treatment. This concept is illustrated in FIG. 6b. The high absorption agent is deposited on top of the surface in an external layer 304, or, alternatively, is allowed to penetrate the material surface and be absorbed within a layer of predetermined thickness 302. The beam emanating from the lens 314 would normally not interact with the native target material 300 (as indicated by the dotted line representing the beam penetration into the target material) However, with the application of a highly absorbing agent (such as an exemplary black china ink or microscopic carbon particles), the beam emanating from the lens 314, will now be strongly absorbed by an externally applied doping agent at 304, the absorbed doping agent layer 302, or the doping agent applied to locations within the material volume at 306. Targets 310 and 312 represent additional exemplary target shapes which can be marked through auxiliary doping and then removed by or modified by the beam.

Once the beam whose power densities within the native target material, is below interaction threshold, encounter either one of doped volumes, high absorption of the pulse radiation into the tissue will ensure initiation of ablation within the high power density volume, and/or plasma initiation because of the high energy level deposited in the small layer of the absorbing agent. Ablative interaction with the absorbing agents are indicated by the symbol 318.

Often small residual modifications to the surface follow the interaction with the laser source, act as subsequent absorbing agents and perpetuate the process at any desired pulse repetition rates. Consequently, all the advantages and unique characteristics of the plasma-mediated ablation as contemplated above, also apply in this case.

Figure 6C:
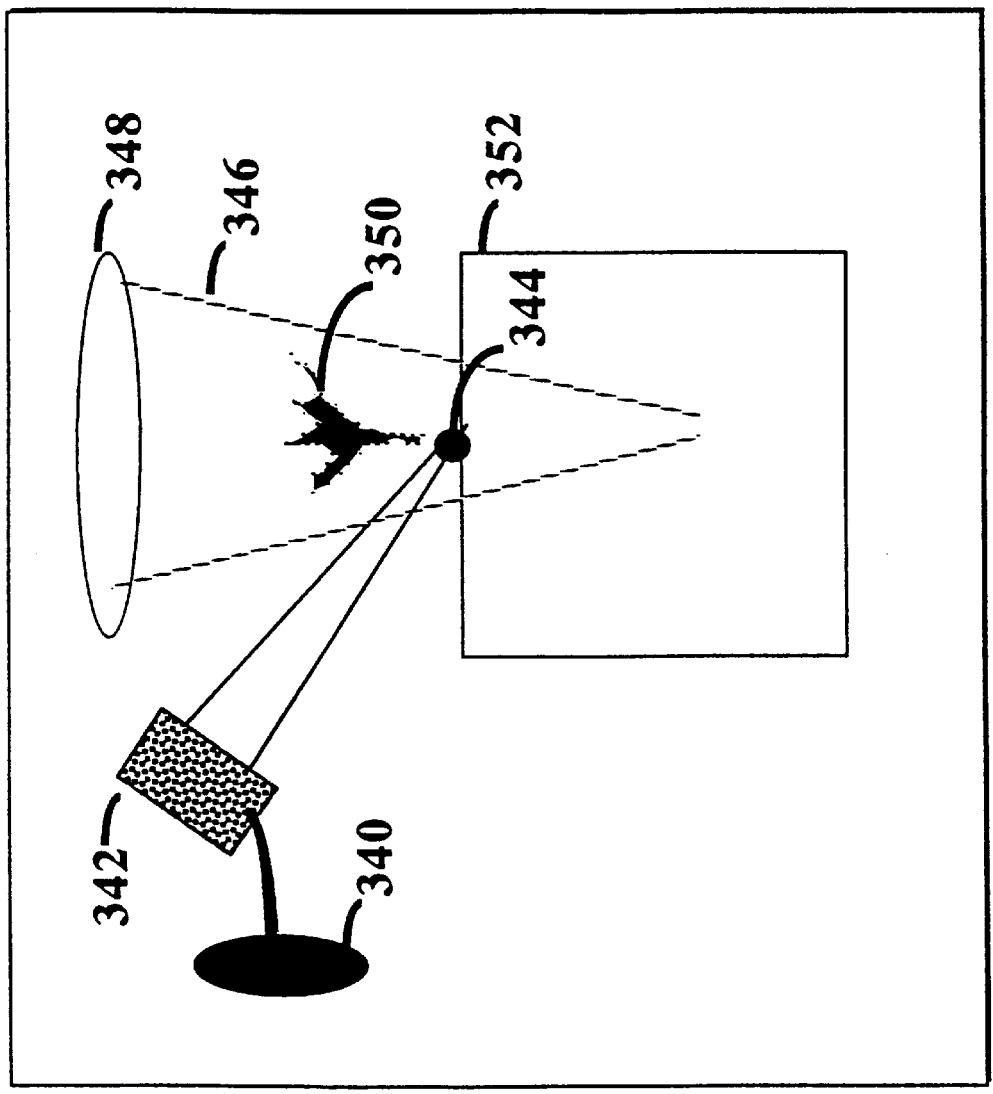
FIG. 6c, is a simplified block level schematic diagram of an absorbing-agent dispenser apparatus suitable for depositing a highly absorbing substance at a pre-selected region of the material in order to induce selective, highly-accurate, beam-target interaction suitable for practice of principles of the invention.

Finally, in some cases where focusing inside the target volume is possible, plasma-mediated interactions can be initiated without the application of a doping agent, simply by focusing the beam to spot sizes which allow concentration of power to above the threshold power density for initiation of interaction with the material. This condition is illustrated in FIG. 6b by the beam emerging from lens 316 and focused down to above the threshold power density at a predetermined targeted location 308 well within the targeted material. Again, once power density inside the targeted volume is above the threshold power density an interaction is initiated as indicated by the symbol 318.

ii) In some cases and material types, the modified absorbing layer created by the absorbing agent will be completely removed by one or more pulses and it will be necessary to apply the absorbing agent after one or several pulses. To this end, it is contemplated by the practice of the present invention to construct an absorbing agent deposition device which will very accurately and synchronously to the pulse laser operation, eject an absorbing agent source onto the targeted area. For an exemplary 1 KHz, 1.05 $\mu$m radiation source, such an ejection source will have to eject a drop of absorbing agent sometime after the completion material ejection due to previous pulse action, but within the 1 ms time interval between the pulses. FIG. 6c shows an apparatus for a repeated, synchronous (with the laser pulses) application of a highly absorbing agent to the targeted material surface. In the figure the ejector 342 draw the absorbing agent from a reservoir 340 and direct a drop of a predetermined volume into the desired interaction location 344. The ejector can be, in principle, similar to an exemplary ink jet injection technology available from the commercial ink jet printer industry. The beam 346, emanating from the lens 348, will normally not interact to modify or ablate the material 352. The presence of the absorber spot 344, however, will now ensure strong interaction 350 at the targeted location.

iii) Finally, material can be temporally and spatially prepared and/or injected with absorbing agents at predetermined location within the three-dimensional volume of the target material. Such preparation will then be selectively activated by the penetrating laser in order to create highly precise material removal or modification in three dimension. Injected or prepared high-absorbance at locations 306, 310, and 312 in FIG. 6b illustrates selective deposition of absorbing agents of various shapes which can assure time- and space—dependent, selective interactions within the three-dimensional material volume.

Principles of Operation: Non-ablative Material Modification

The method of the present invention also offer the possibility for a controlled, variable rate material modification by a pulsed electromagnetic radiation beam. The interaction between the pulsed electromagnetic radiation beam and the material is characterized by a modification threshold volumetric power density, which is a function of the target material properties.

The principle of non-ablative beam modification is based on the fact that between the threshold for material ablation and the very low power density which leave the material unaffected, there is a transition power density range whereby the beam energy deposition characteristics yield sufficiently high power densities to induce irreversible changes within the target volume, but do not result in ablation, or explosive events. Specifically, at very low power densities there will be no modification or any irreversible changes in the target material. However, as the power density is increased, irreversible changes may occur before the threshold for complete ablation takes place. In soft tissue this may corresponds to coagulation or evaporation of water molecules with no ionization or a large number of molecular bonds are broken. In crystals such changes may correspond to changes in crystalline structure and substations. In hard tissue or porous, water saturated lattices this may appear as dehydration of the material and/or partial melting of the lattice. In an exemplary dentin hard tissue material as well as for ceramic-like materials, quartz and fused silica, the inventor has determined that the threshold for ablation with a 0.35 ps source is on the order of $10^{12}$ w/cm$^2$. For soft tissue this ablation threshold is somewhat lower—on the order of $10^{10}$ to $10^{11}$ w/cm$^2$. It is thus possible to select beam-target parameters yielding power densities below these limits yet sufficiently high for irreversible material modification.

In general, such irreversible modification may include one or more of the following alterations: chemical and physical changes, changes to viscoelastic properties, changes to optical or thermal properties, changes in chemical properties, changes in physical properties or physical breakdown, partial or complete melting of the targeted region, melting, and partial or complete vaporization of the targeted volume.

Using a source capable of generating an output beam of a sequence of electromagnetic pulses each having a pulse duration in the range of about 3 femtosecond to about 10 millisecond; such a beam can be directed toward the target at or below the surface. The beam may, for example be redirected by a lens or reflective optics so that it converges spatially as it nears the target area. Once the beam converges into a threshold volume, the resultant power density may be sufficiently high to induce irreversible modification. The beam conversion, on the other hand, may be designed so that power densities may never reach the threshold for ablation.

Also clear is the fact that as the pulse duration decreases from the upper 10 ps range to the femtosecond range, the beam power densities are generally high because of the shortest of the pulse duration. Thus, small changes in spot size (as the beam converges toward the target) will result in large changes in the power densities and may increase their values beyond the threshold for modification or ablation. The ultimate result is then much increased sensitivity to spatial location and increased spatial resolution with decreased pulse duration.

Selective locations within the target material volume surface may possess properties that enhanced their scattering and/or absorption. A collimated or slightly converging beam impinging on the target material may continues its propagation through the material below modification threshold until they encounter such high absorption regions where energy deposition is increase and deposited power densities are increased above the modification threshold. Such selective location may occur naturally or may be inserted or induced artificially, by the operator.

Finally, in some cases it is also possible to modify the pulse frequency components temporal distribution so that as the incident pulse transverse the material, slower moving components that were arrange to initially lead the pulse, are being overtaken by faster, initially trailing frequency components. Such a velocity dispersion effect will shorten the pulse duration as it transverses the material volume. This effect can be design to yield the shortest pulse duration precisely at the target region, thus resulting in increasing the power density at that location above the modification threshold, or if so desired, above ablation threshold.

Once a single pulse modification interaction has occurred, allowing mechanical or thermal transients caused by the electromagnetic radiation pulse to substantially decay would make subsequent pulse interaction possible. Operating the pulse source at a pulse repetition rate greater than 0.1 pulses per second until a sufficient volume of the material has been modified would allow large volume modification.

Alternatively, scanning and moving either the beam or the target in three dimensional space would allow the operator to generate virtually any modification pattern desired. Combination with control and feedback devices (to be discussed below) along with such translation mounts and temporal control over the beam source on/of times and pulse repetition rate can provide a completely automated method for generation of such material modification patterns.

Taking advantage of various intensity profiles of the beam and utilizing the threshold nature of the modification interaction, modification cross section smaller than the diffraction limits can be obtained because only portion of the beam spot size may reach the above-threshold power density values. In a Gaussian beam profile, for example, power densities at the center of the beam significantly exceed those in the wing. Making further use of non-linear absorption which are very sensitive to the beam power density distribution, modification cross section as small as 100 or even 10 nanometer can be envisioned.

Thus, material modification rate can possibly be varied from the range of from about $0.01^3$ micrometers cube per pulse to about 100,0003 micrometers cube per pulse, said modification rate being substantially constant depending substantially on the volumetric power density threshold characteristics and on the source electromagnetic beam characteristics.

Figure 7:
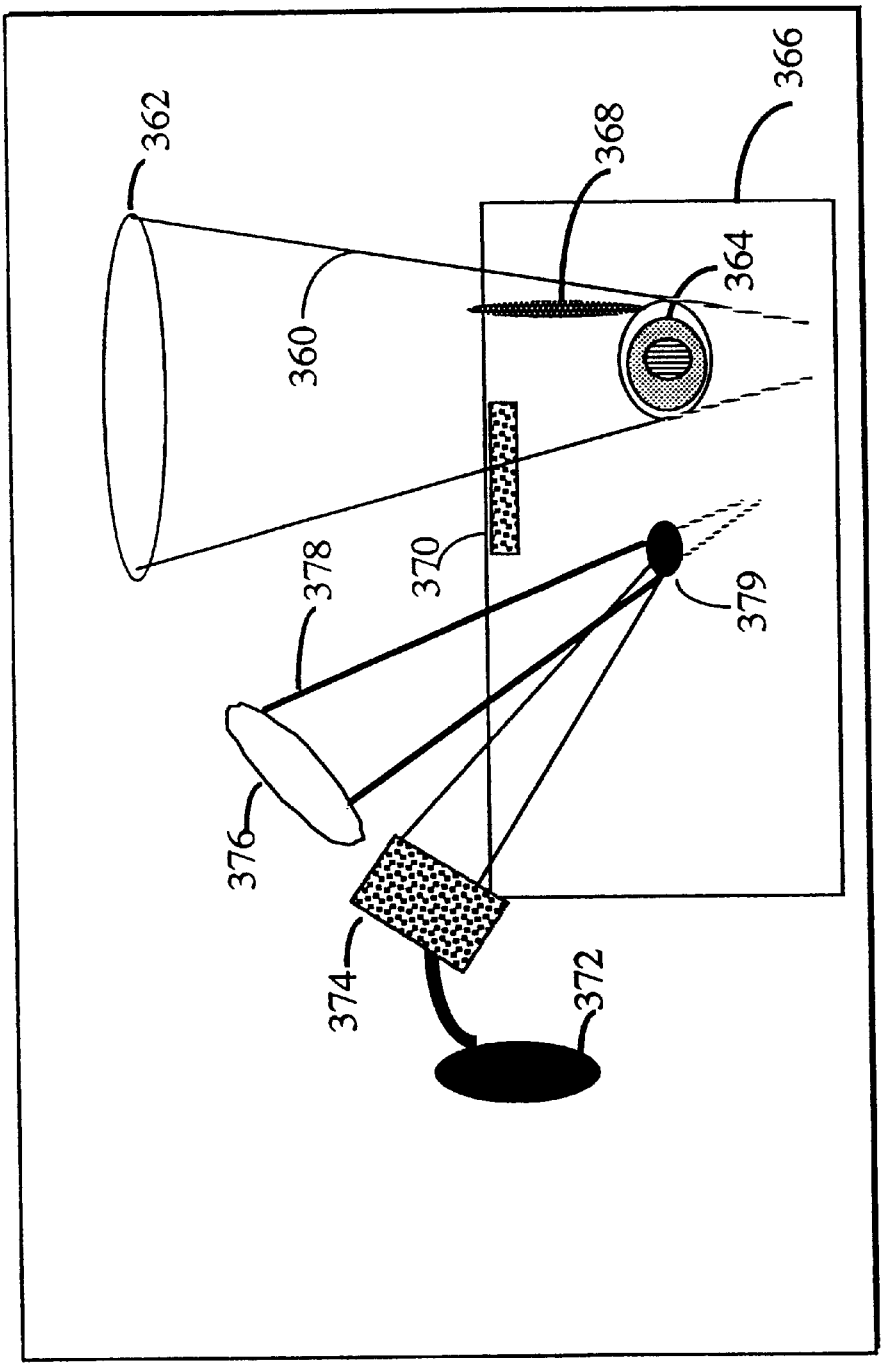
FIG. 7, is a simplified block level schematic diagram of an exemplary apparatus for three-dimensional material modification suitable for practice of principles of the invention.

The principle of operation of the material modification system according to the practice of the present invention can be further understood with the help of FIG. 7.

In FIG. 7, the beam 360, emanating from the lens 362 is impinging on the a target at power density which are below the threshold levels for either material modification or material ablation. As the beam converges, its power density increases until it reaches the threshold for material modification. Modification can include any type of permanent changes to the target volume visco-elastic, mechanical or thermal properties. The dashed lines continuing from the beam 360 below the modification target zone 364 indicate that had the material threshold for modification not been exceeded the beam would have continued past the modification zone 364 undisturbed. The three concentric circles inside the volume indicate that material modification can correspond to changes in material densities and the creation of compression zones within the modification volume 364—zones where the modified material density might vary spatially. While material modification may not entail material removal, an escape chamber 368 may be drilled by the ablating system itself, or may be provided by other means in cases where ablation or vaporization of part of the modified volume of material is desired.

In addition to achieving above modification threshold by spatially focusing the beam, modification threshold can be reached by changing the pulse duration as a function of time through dispersion effects (pulse compression) or through the injection or application of high absorption agents to allow the beam power density to reach above-modification-threshold levels. Pulse compression can be achieved through reverse dispersion when the arrangement of the pulse frequency components is such that faster propagating light frequency components spatially trail the slower components. When arriving at the material the faster components will catch up with the slower components thus compressing the pulse duration. Knowing the frequency dependent of the light propagation speed within the material can allow the designer to predict the exact location at which a desired amount of pulse compression will occur. Thus compression then will bring the pulse power density above the threshold for modification and initiate the interaction. Such and effect can of course be used for bringing the beam power density above ablation threshold at predicted pre-selected time and location.

Also shown in FIG. 7, is a high absorption agent applicator, indicated by the dye reservoir 372 and an injector 374. In this case application to the surface 370 or to a deeper lying region 380 can be accomplished. When an above-modification-threshold beam 378 emanating from the lens 376 arrives at 379, absorption will increase the deposited power density within the intended volume and modification will occur. The dotted lines at the end of the beam 378 indicate that the beam would have continued its path uninterrupted had it not encounter the deposited absorber which forces selective modification of the targeted region of the material.

Principles of Operation: System Construction

In the practice of the present invention a pulsed output beam having a selectively variable output pulse duration from about 3 femtoseconds to approximately 10 millisecond at a variable pulse repetition rate from about 0.1 to about 500 Kilohertz, with a minimum pulse-to-pulse separation of a minimum of about one $\mu$s to allow ejected debris and plasma from previous pulses to clear the target area.

As was pointed out above, a key element in the practice of the present invention is the selection of parameters such that pulse characteristics will ensure removal of most of the deposited energy by the ablation (high ablation depth to energy deposition depth ratio), coupled with high pulse repetition rate so that on a time scale of a practical total exposure time (i.e., on the order of single treatment event, longer than, for example, 1.0 seconds) the overall material removal will ensure ejection of most of the deposited energy.

Depending on the target material and the type of processing required, the energy per pulse can range from about 1 nanojoules to over about 50 Joules, while the beam spot size can vary from about 0.1 micrometers to over 5 centimeter in diameter. Adjusting and focusing the output beam spot size, energy, and pulse duration should create a fluence at the target in the range of $10^2$ W/cm$^2$ to $10^{16}$ W/cm$^2$.

Several classes of pulsed laser systems are capable of generating at least some of the parameter requirements described above and thus serve as a radiation source for some of the applications envisioned in the practice of the present invention. Those having skill in the art will recognize that the pulsed laser classes known as flash lamp pumped normal mode lasers, Q-switched lasers, pulsed excimer lasers, mode locked lasers and chirped pulse amplified lasers may serve as a suitable source for the practice of the invention. This list, however, is only partial, and in principle, additional pulsed sources of electromagnetic radiation capable of producing output parameters which fulfill the requirement specified by the present invention, may serve equally well in the practice of the present invention.

In one possible embodiment for the longer pulse regimes, a flash-lamp-pumped solid state laser may be equipped with a variable pulse width controller permits the laser operator to vary the pulse width of the flash lamp from a microsecond range to the 1 ms in increments on the order of several microsecond. This capability will allow optimization of the performance through temporal variation of the laser pulse. The electronic pulse controller can be designed to provide for continuous, batch, single shot, or external triggering capable of controlling the repetition rate in 1 Hz increments up to several KHz repetition rates.

Shorter pulses can be generated by Q-Switching. Rotary, acoustic-optic, and electro-optic Q-switching are only a few possible mechanisms for generating pulse in the nanosecond to the microsecond range.

Shorter pulse yet may be provided by mode-locking and using chirped pulse amplifiers or through saturable absorbers technologies well-known to those skilled in the art.

Figure 8A:
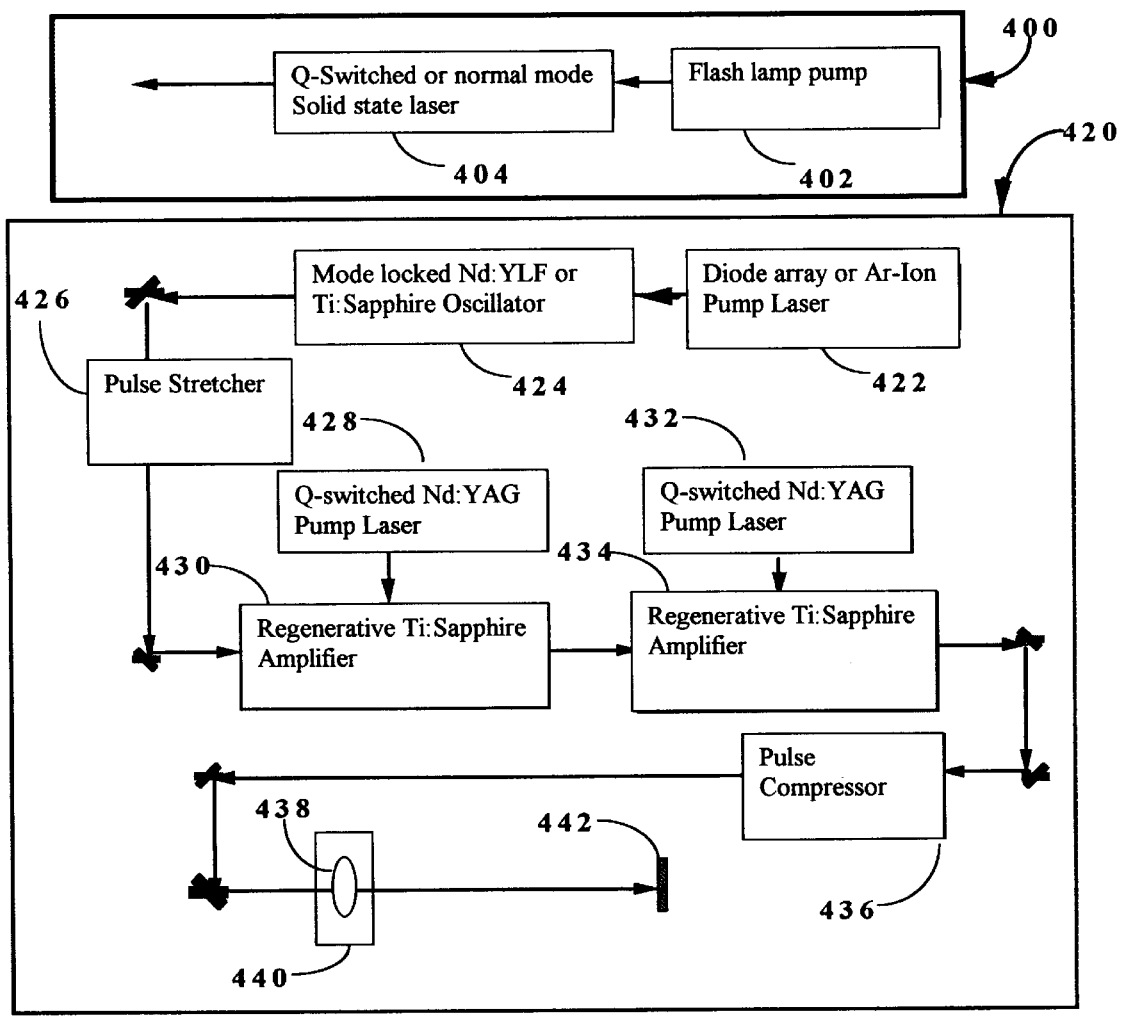
FIG. 8a, is a simplified block level schematic diagram of exemplary pulse laser systems suitable for practice of principles of the invention.

A diagram of an exemplary, high repetition rate laser system, suitable for practice of principles of the present invention is depicted in FIG. 8a. The exemplary laser systems depicted represents a laboratory-model prototype devices in accordance with principles of the invention. As such, the laser system depicted in FIG. 8a and described below comprises a degree of complexity and control variability suitable for laboratory experimentation, but which may exceed what is necessary for practice of the invention.

The exemplary laser systems depicted in FIG. 8a includes a parameters regime which has been determined by the inventor to be efficient in ablating most types of material. Some of the exemplary laser systems depicted in FIG. 8 has been shown to efficiently ablate most material. As will be described in greater detail below, any type of laser system, capable of operating within the parameter regime described above, can be employed in practice of the invention.

Several additional classes of pulsed laser systems are capable of generating at least some of the parameter requirements described above and thus serve as a radiation source for some of the applications envisioned in the practice of the present invention. Those having skill in the art will recognize that Q-switched flash lamp pumped or diode pumped lasers may serve as a suitable source for the practice of the invention. Other possibilities may even include a continuously emitting source of electromagnetic energy (for example, continuously emitting laser sources known as continuous wave (CW) lasers). Such sources output may be modified by various means to result in electromagnetic beam characteristics which effectively fulfill the requirement of the present invention.

Some possible laser system configurations are depicted in FIG. 8. The first system, depicted by the components inside the box 400, in FIG. 8a corresponds to the a pulse regime ranging from about a single nanosecond to about several millisecond range. It can include an exemplary flash-lamp pump 402 pumping an exemplary Q-switched solid-state laser 404, with pulse duration ranging from the nanosecond to the microsecond, or an excimer laser 406 in the nanosecond to the several hundreds nanosecond range, and up to several KHz of pulse repetition rate. An exemplary flash lamp pump 402, pumping a normal-mode solid-state laser (not shown) which would fit in the location 404, generating pulse duration from about the microsecond to about the several millisecond range.

The second system 380, corresponds to a the shorter pulse duration regime. It is capable of producing pulses in the range from about 3 femtoseconds to over 5 nanosecond. This system produces a pulsed output beam having a selectively variable output pulse duration which can be changed continuously over the about 3 femtoseconds to over 1 nanosecond range. It is also capable of producing a variable pulse repetition rate from about 0.1 to over several KHz by selecting the proper pump laser 389 for the regenerative amplifier. The energy per pulse, obtainable from the exemplary shorter pulse regime laser system is variable from about 1 nj to over 50 millijoules, deliverable in a beam having a spot size variable from about 5 micrometers to over 1 centimeter in diameter.

Although, as this discussion demonstrates, any type of laser system, capable of operating within the parameters described above, can be employed in practice of the invention, the shorter pulse regime laser system, 380 of FIG. 8*a*, preferably comprises a mode-locked oscillator 384 which operates to provide pulses having the same or shorter durations than the desired final pulse duration. The mode-locked oscillator 384 is pumped by a solid-state laser, a diode array, or an Argon-ion pump lasers 382. Commercially available oscillators, providing 100 femtosecond pulses, as well as laboratory built oscillators, providing 15 femtosecond pulses, have shown themselves suitable for practice of the invention. Both oscillator embodiments often employ Titanium-doped sapphire as the lasing material and utilize the well known Kerr effect for mode-locking, although the well known acousto-optic effect is often also suited for mode-locking. The pulses produced by such oscillators are typically low in energy, particularly on the order of about 1.0 nanojoules.

These low energy pulses are then stretched in time by over about four orders of magnitude (a factor of ten thousand) by a grating pulse stretcher 386. The pulse stretcher 386 suitably comprises a diffraction grating to disperse the various frequency components of the broad-bandwidth pulse produced by the oscillator. By transmitting the various frequency components along different paths through an imaging telescope, pulses are lengthened in time by an amount $\Delta L/C$, where $\Delta L$ is the difference in the optical path length between the various frequency components and c is the speed of light.

The stretched pulse is then amplified by several orders of magnitude, preferably to the millijoule range, in an amplifier stage. The amplifier stage may comprise any one of various types of laser amplifiers familiar to those skilled in the art. Most commonly, however, a regenerative amplifier, wherein a pulse is able to make multiple passes through a single amplifier media is used. The regenerative amplifier employs Titanium-doped sapphire (Ti:sapphire) as the gain medium. Because of the short storage time of Ti:Sapphire, a second, pump laser 389 of FIG. 8*a*, is used to pump the Ti:Sapphire gain medium. Such a pump laser can be a frequency-doubled, Q-switched, Neodymium-yttrium-aluminum-garnet (Nd:YAG) laser. The energy required to pump the Ti:Sapphire regenerative amplifier 388 is typically greater than five times the energy output of the regenerative amplifier.

The repetition rate of the system is determined by the repetition rate of the pump laser 389. By changing the repetition rate of the pump laser, operation at repetition rates up to and in excess of 1000 Hertz can be achieved. Switching of the pulses into and out of the regenerative amplifier 388 is accomplished with conventional pulse switching technology based on the well-known Pockels effect for polarization rotation. Pulses are switched out of the regenerative amplifier when saturation is achieved.

The regenerative amplifier 388 produces pulses of up to about 10 millijoules in energy. These pulses can be sent directly to a pulse compressor 390 or, alternatively, further amplified, by an additional Ti:Sapphire regenerative amplifier to increase the pulse energy.

Following amplification, the stretched and amplified pulse is compressed by a variable length pulse compressor 390, employing a diffraction grating. In a manner similar to the pulse stretcher 386, pulse compression occurs by controlling the optical path of the various frequency components of the laser pulse through the compressor. Different frequency components are directed along different paths by the angular dispersion of the grating. By controlling the dispersive path length taken by the various frequency components, a variable duration output pulse is obtained.

The exemplary laser system 380 has demonstrated a final pulse duration which is adjustable in the range of between about 60 femtosecond and about 1000 picosecond. The laser pulse is directed to a material target 394, through a focusing lens 392, by a delivery system which may comprise an open beam transport system, an articulated arm, an optical fiber, or a hollow core optical wave guide. If desired, the delivery system may be adapted to provide additional stretching or compression of the pulse duration. The spatial profile of the final pulse is then modified by the lens system 394, assuming its final shape, the beam then continues towards the target 394. Suitable focusing elements may be comprised of refractive (lenses) or reflective (mirrors) elements. A typical exemplary focusing element may consist of a simple large f-number single lens for focusing the beam onto the target area in a spot size greater than 1.0 micrometers. Spot size is easily adjusted either by moving the target away from best focus, or by simply changing the delivery lens/mirrors configuration.

This exemplary laser system 380 of the present invention is thus able to produce a continuously tunable output by changes in optics and adjustments. Operation at the second harmonic (350 to 532 nanometers) is accomplished by passing the beam through a thin potassium di-deuterium -phosphate (KD*P) crystal after compression. The KD*P crystal is cut for type-I phase matching and is typically between 0.5 and 4 millimeters in length.

Although the high repetition rate laser systems has been described with reference to the exemplary q-switched laser, flash-pumped normal-mode solid-state laser, mode-locked and chirped-pulse amplified solid-state laser, embodied in FIG. 8*a*, it will be understood by those having skill in the art that many different laser systems, operating in various portions of the electromagnetic spectrum and capable of providing pulses having durations of from about 3 femtoseconds to about 10 ms, at repetition rates of up to 100,000 Hertz, are within the contemplation of the present invention. What is desired from such systems is that the amount of material and residual energy left by a single pulse is small, that the ratio of the single-pulse ablation depth to energy deposition depth is high, and that, if high material volume removal rate is desired, the system pulse repetition rates is sufficiently large that substantially much of the residual energy accumulated in the target is removed by subsequent pulses within the pulse train so that most of the deposited energy is completely removed by the ablation process itself, with the entire procedure yielding substantially no collateral damage to surrounding material.

Figure 8B:
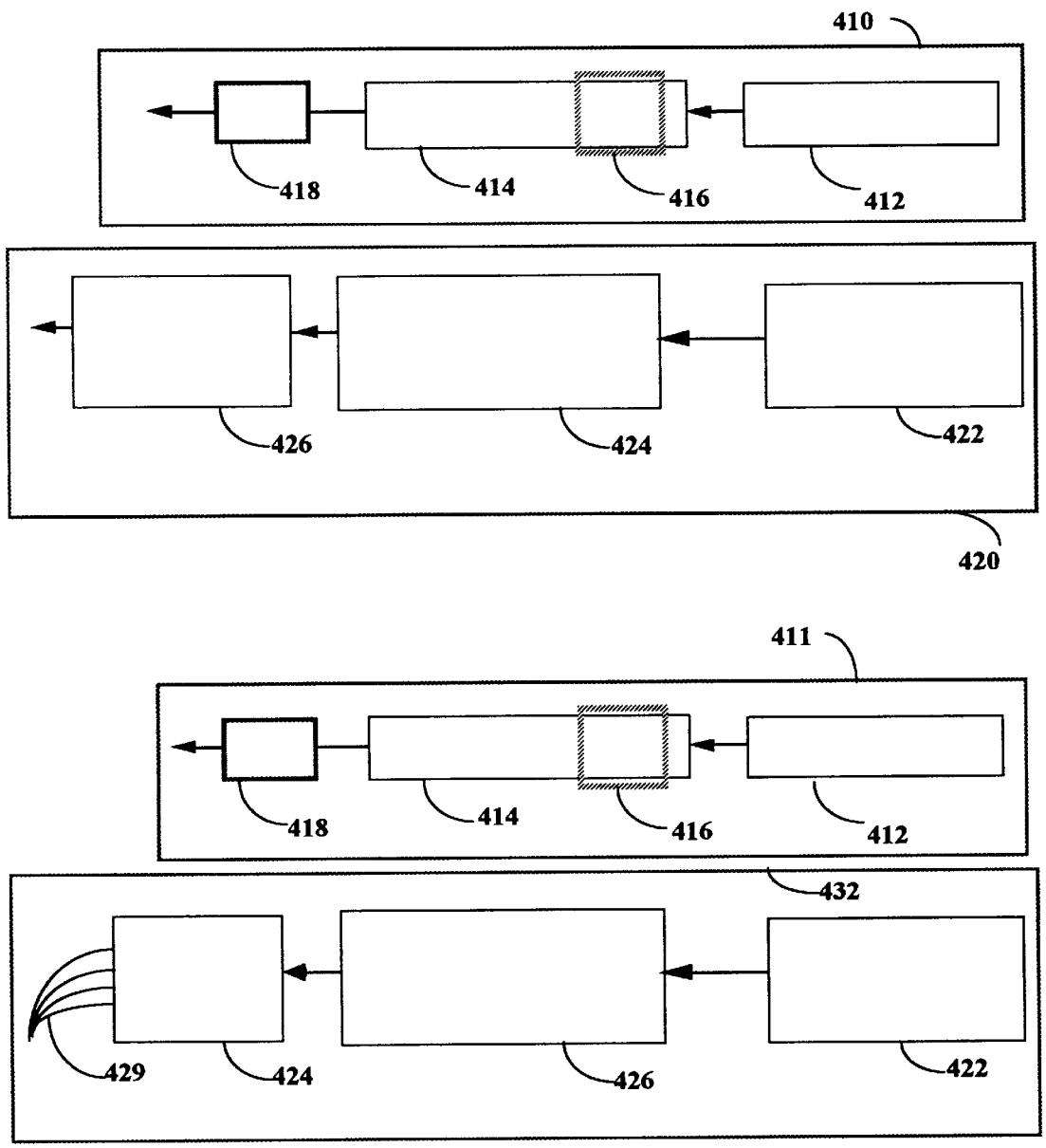
FIG. 8b, is a simplified block level schematic diagram of exemplary continuous wave and pulse laser system with components for modifying output radiation frequency, phase, as well as temporal and spatial energy distribution.

FIG. 8b illustrate additional systems. 410 is a solid state pulsed system which is pumped by a CW or a Quasi-CW laser source. For example, a pulsed or a CW flash-lamp may serve well as a pump source. A CW or a quasi-Cw diode source can also serve very well for this purpose. Such diode laser sources may be arranged as diode arrays and diode bars as well as stacks of bars to produce substantial pump power of up to kW of continuous power. Such sources 412 may be used to pump a Solid-State crystal 414 with Q-switching 416 (such as an acousto-optic, electro-optic, or other means for producing a Q-switched output pulse characteristics in accordance with the requirement of the present invention). The output of these crystals than can be modified to longer wavelengths using an Optical Parametric Oscillator (OPO) 318. Alternatively, the output may be further modified by passing the beam from 314 through a thin potassium di-deuterium-phosphate (KD*P) crystal. The KD*P crystal is cut for type-I phase matching and is typically between 0.5 and 4 millimeters in length. Additionally other non-linear crystal such as KTP may serve equally well for many applications requiring output frequency conversion.

FIG. 8b also illustrates other possible preferred embodiments. The system 420 may consists of a CW electromagnetic source 422. Any continuously emitting (CW) electromagnetic energy source may serve for this purpose. For example a CW laser source such as a Carbon Dioxide, an Ar$^+$ ion, a Tunable Ar$^+$ ion—pumped Dye laser, a Krypton Gas laser, a Ruby laser, or even a non-coherent radiation source (such as, for example a Xenon flash lamp). A CW diode source can also serve very well for this purpose. Such diode laser sources may be arranged as diode arrays, diode bars, as well as stacks of bars to produce substantial pump power of up to kW of continuous power. Such source 422 output may then be temporally and spatially modified in an output modifying device 424 to produce a pulsed output characteristics in accordance with the requirement of the present invention.

Modifying the Continuous Wave (CW) output beam characteristics so that they conform to the operating characteristics described by the present invention can be understood with the help of FIG. 8c and will be described below. The beam modifier 424 is shown in FIG. 8b: In the device 420 it is shown before the phase/wavelength modifier, while in 421 it is shown placed behind the phase/wavelength modifier. Those skilled in the art will recognize that the differences and advantages may be in the ease of delivery and manipulation of the output but may both be used equally well.

Figure 8C:
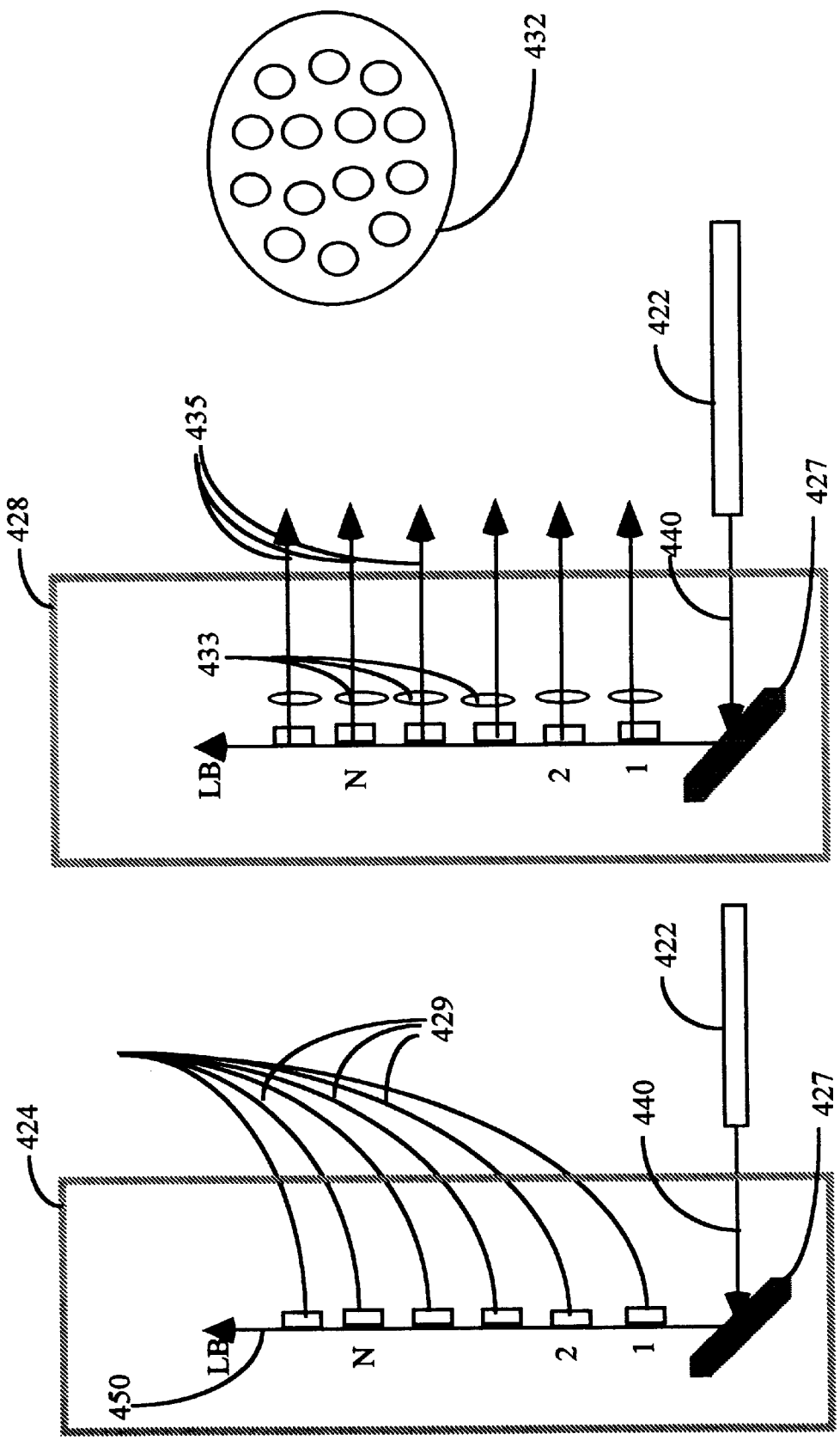
FIG. 8c, is a graphical representation of a system for modifying continuous wave source to yield multiple beams output characterized by variable pulse repetition rate in accordance with the requirements of the present invention.

The principles of operation of an output modifying device 424 is now described using FIG. 8c.

The source Continuous Wave output 440 is directed towards a beam modifying device 424 containing a reflector 427 which direct the beam towards a series of switches 1, 2, 3 . . . N . . . The switches allow the beam to continue uninterrupted except for a short time duration τ when they turned on to allow reflection of the beam of light towards their respective fibers 429 whose output at the target may look like 432 of FIG. 8c. Alternatively, the switching devices can also reflect the beam 440 directly towards a specific location on the target (or through a lens which focus the deflected beam onto the target) for time duration τ. Following the period τ for which the switch is on, the switch is turned off again and the beam 440 continue to propagate directly thorough switch 1 and the rest of the switches. At some later pre-determined time switch 2 is turned on and it reflects a portion of the beam 440 for a period τ towards its own coupled fiber or directly to the target (or a lens which focus the beam onto a unique location on the target) at which time it is turned off. This procedure is repeated for all switches 1,2,3, . . . N and then the entire sequence is repeated all over again.

Again, the energy from the continuously emitting beam 440 is directed with a delivery system to a selected separate spatial location on the target. The delivery system can consist, for example, of an optical fiber, an optical fiber and lenses combination, a hollow wave guide and lenses, and a combination of lenses and mirrors.

The output laser beam 440, is then directed by a beam-switching device 427 as shown in FIG. 8c. Such a beam switching device may, for example, comprise the well known Pockels Cell, the well-known Kerr Cell, a rapidly rotating mirror. It may also consist of other mechanical, optical, electrical, magnetic, electromagnetic or any other means of rapidly switching out a portion of the electromagnetic beam so that a pre-determined time duration can be precisely selected.

Alternatively, the source CW beam 440 can be directed towards a slightly different beam modifying device 428 containing of sequence of optical switches 1,2,3 . . . N which sequentially redirect the CW beam towards the lenses 433 which then focus their respective beamlets into a pattern similar to 432 where each spot size is small enough to allow power densities (energy per unit volume) above the threshold for material ablation.

Figure 8D:
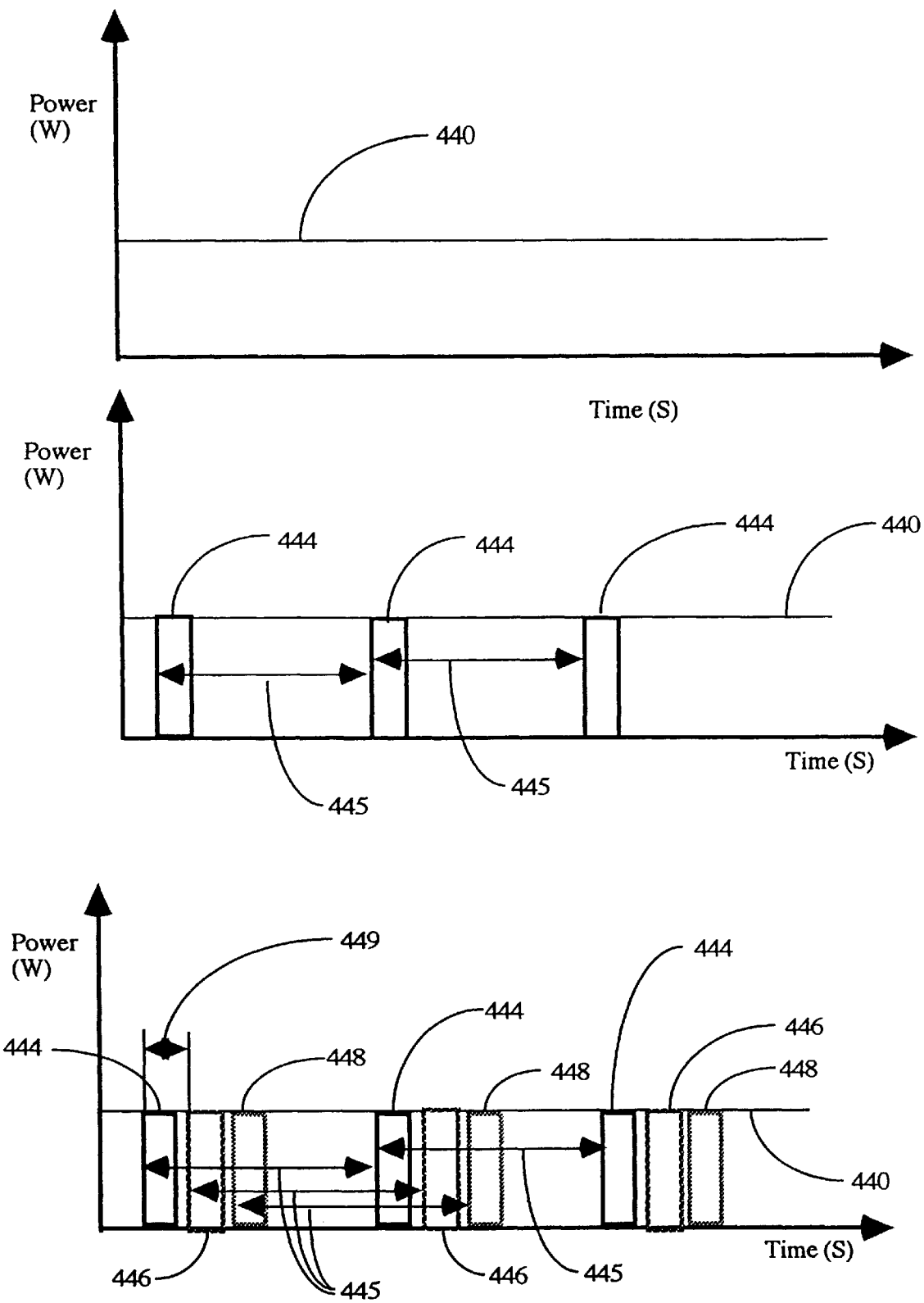
FIG. 8d, is a graphical representation of a method for partitioning the output of a continuous wave source in order to generate a multiple beam output where each one of the multiple beam output is characterized by a variable pulse repetition rate in accordance with the requirements of the present invention.

The output from such a sequential switching device is shown in FIG. 8d. At the top of the figure, the output of a continuous wave source, 440 is shown as a function of time. The output 444 from one of the switches (for example, switch #1) is shown in the second set of axes. This short output 444 lasts for a time duration τ while the corresponding switch is turned on. The time duration 444 can, for example, be as short as one nanosecond or even shorter. The remaining energy of the output is not used at that particular target location until an interval of time 445 has passed. The time interval 445 corresponds to the inverse of the desired output pulse repetition rate. The pulse repetition rate is selected in accordance with the requirement of the present invention. For example, to achieve a 1 KHz pulse repetition rate the fiber 429 coupled to switch #1 (see FIG. 8c), a time interval 445 of about 1 ms must be allowed to pass before the next beam output is used for the specified time duration 444.

Additionally, other portions of the output beam, for example portion 446 and 448 in FIG. 8d, can be used in addition to the first portion 444. Many sequential portions 444, 446, 448 . . . can be used as long as these segment selection does not overlap (for example there is no time overlap between portion 444 and 446) and as long as the energy output from each beamlet and fiber-optic conduit 429, comprises a pulse train with a generated pulse repetition rate and pulse duration characteristics as described by the present invention.

The modified portions (444, 446, etc.) can be generated from the CW electromagnetic beam 440 using the modifier 424 containing a beam switching device 424 for selecting and redirecting portions of the continuous emission output beam 440. Such modified portions 444, 446, etc. can then be directed to desired target locations.

Directing Such modified portions 444, 446, etc. to adjacent target locations to generate beamlet ablation pattern 432 shown in FIG. 8c, creates some additional benefits as described below.

In a preferred embodiment, the segments 444, 446, etc. of the CW beam 440 can be directed to the opening of an input coupler of a number of fiber optic cables leading these pulse trains to adjacent locations in the target area.

In a second preferred embodiment, the segments 444, 446, etc. of the CW beam 440 can be directed to the opening of focusing devices so that these newly created beamlets of pulse trains conforming to the requirement of the present invention, can be directed to adjacent locations in the target area.

In a second preferred embodiment, the segments 444, 446, etc. of the CW beam 440 can be directed to the opening of an input of articulated arms or Hollow Wave Guides so that these beams of pulse trains which conform to the output characteristics in accordance with the requirement of the present invention, can be directed to the same location or to adjacent locations.

Figure 8E:
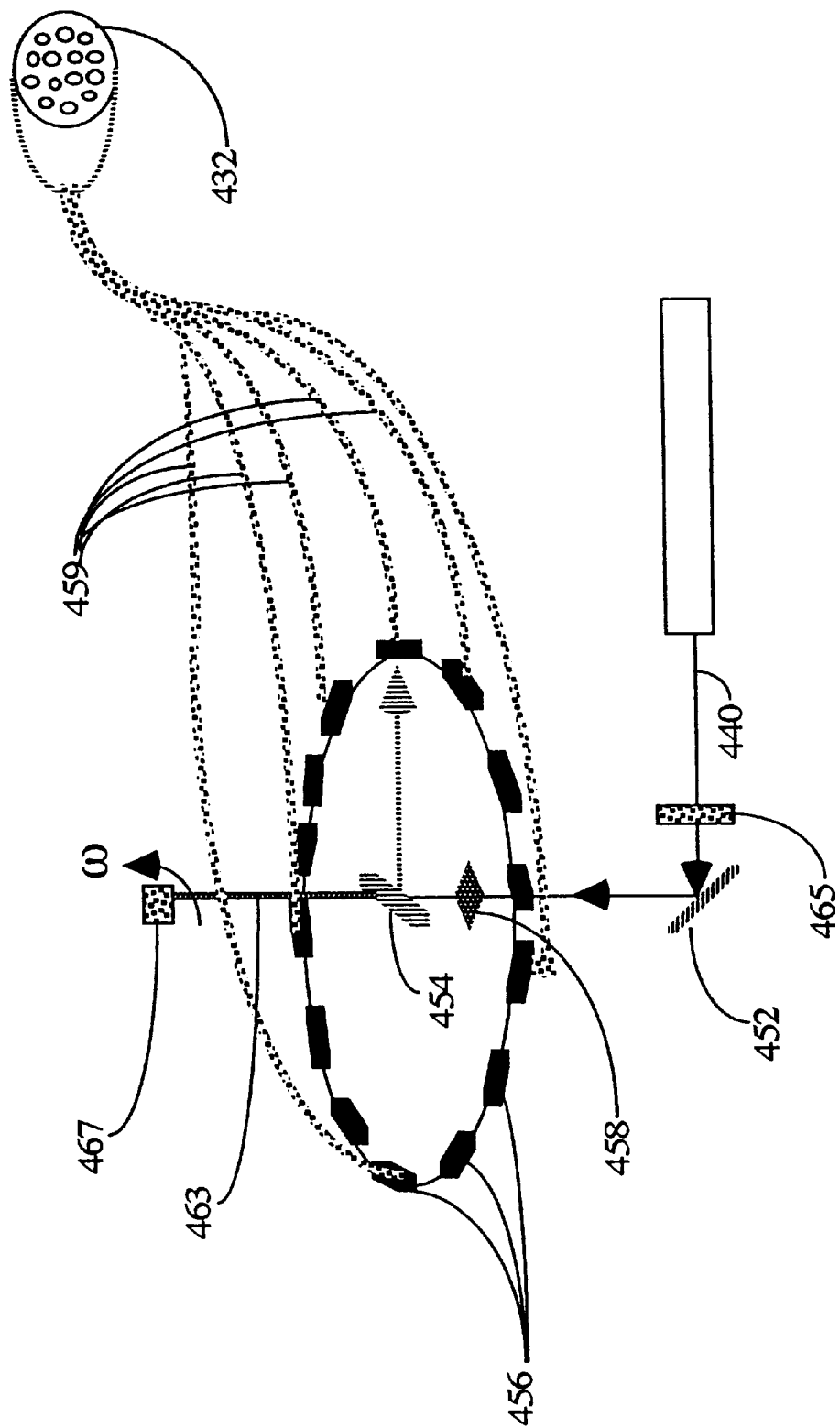
FIG. 8e, is a graphical representation of a spinning mirror method for partitioning the output of a continuous wave source in order to generate a multiple beam output deliverable to couplers arranged in a circular configuration, where each one of the multiple beam output is characterized by a variable pulse repetition rate in accordance with the requirements of the present invention.

Additional preferred embodiment of the present invention utilizing an optical fiber bundle 429 can be understood with the help of FIG. 8c and FIG. 8e.

The beam from the electromagnetic energy source 422 (see FIG. 8c) is redirected into the output modifier 424 through 1,2,3 . . . N couplers to the optical fibers 429. The switching (or redirecting) optics 327 can be made for example from Kerr or Pockels cell switches, non-linear crystals, or even mechanical mirror which deflect the light into 1,2,3, . . . N couplers which couple the energy from the original beam 440 into the couplers and the optical fibers 429.

The source energy may be deflected for a period of from 1 ps and up to 10,000,000 $\mu$s in accordance with the requirement of the present invention. These (see FIG. 8d) selected time-segments 444, 446, 448, etc. (for example a time segment of duration $\tau$), are sequentially directed into sequential, separate and different optical fibers. When each of the pre-selected 1,2,3, . . . N, fibers has received a single time-segment of energy, an "off time" of $\Delta t$ is allowed to pass before the next cycle of sequential time segment is redirected into the same set of N fibers at exactly the same sequence. The off time interval $\Delta t$ is selected so that $(\tau N)+\Delta t=(1/PRR)$ where PRR is the desired pulse repetition rate as specified by the present invention.

The result is an output from each and every fiber in the bundle. The output of each fiber in the bundle is a sequence of pulses each of durations $\tau$ and of pulse repetition rate PRR, equal to the inverse of the time interval 445 of FIG. 8d.

An additional preferred embodiment is shown by the Rotating Mirror arrangement of FIG. 8e. This exemplary depiction of the preferred embodiment shows the CW beam 440 from the source being directed to a mirror 452 which redirects the beam to a rotating mirror 454. The rotating mirror, in turn, redirect the light towards a series of couplers 456 arranged around the circumference of a circle. The couplers couple the rotating light to either optical fibers 459 openings, to hollow waveguides, or to a set of articulated arms or mirrors to redirect the beams energy so that a sequential multiple beam pattern is formed at the target. The spinning mirror 454 is located at the center of the circle. The mirror, may, for example, be suspended from a driving high precision motor by a spinning rod 463. The combined array of fibers/beamlets output may assume the shape 432 in FIG. 8e.

To show how the spinning mirror arrangement of FIG. 8e allows for the generation of pulsating beamlets sequence of figure of FIG. 8c, consider the a mirror spinning with a rotational velocity $\omega$ of 1000 cycles per second. With the aid of a focusing lens 458 the CW beam 440 is focused onto the couplers 456 so that its beam size is 100 $\mu$m and is focused onto each fiber opening for a dwell time of 1 $\mu$s.

The linear velocity of the beam at the fiber opening (on the circumference of the circle) must then be $V=(100 \mu m/1 \mu s)=100$ m/s With $V=\omega R$ (where R is the radius of the circle of couplers, V=100 m/s and the rotational velocity, $\omega$=1000 cycles per second). Thus, R is approximately 1.7 cm and the circle circumference is approximately 10 cm.

In another preferred embodiment (FIG. 8e) the driver 467 which drive the spinning mirror 454 can be a high precision stepping motor electronically synchronized with a shutter 465. The CW beam is allowed to pass through the shutter 465 for a time duration $\tau$ (for example $\tau$ can be 344 in FIG. 8d) when the Mirror 454 is pointing to towards one of the coupler 456 for a time duration $\tau$. Following this desired exposure, the shuttered 465 is turned off and the mirror 454 which was stationary for the time duration $\tau$ is moved by the stepping motor 463 to the next coupler 456 and fiber 459. After a period $\Delta T$ (for example 345 in FIG. 8d) the shutter 465 is opened again for a period $\tau$ and the beam is allowed to couple again with the next coupler 456. As will be evident to those skilled in the art, the shutter 465 can also be constitute a deflecting mirror or any other optical switch.

A 10 cm circle has room for approximately 1000 fibers each 100 $\mu$m in diameter. 1000 fibers each 100 $\mu$m in diameter cover an area of approximately 0.075 cm². This cumulative fibers and beamlets area is large enough to cover a rectangle whose side is 2.7 mm long—a practical spot size for many applications in material processing and tissue ablation.

In all preferred embodiments the fiber assembly, hollow waveguides, or focus free beams may then be directed into the target so that an ablation spot pattern like the exemplary assembly of holes 432 in FIG. 8c is formed.

The time-space tailoring of the CW source beam into an array of adjacent pulsing beams (each necessarily time-delayed with respect to the other) as described above carries some additional advantages regarding the minimization of thermal and mechanical collateral damage. The advantages are due to the arrangement of the fiber and focused free-beams in a configuration of adjacent shapes that looks like 432 in FIG. 8c and are fired in a sequential manner as illustrated in FIG. 8e.

Advantages of a Fiber Bundle and Focused Free-beams in Configuration of Adjacent Beams Using a Continuously Emitting CW source and dividing the CW energy 440 (see FIG. 8d) into several beamlets of duration t characterized by a certain pulse repetition rate (for example 444 and 445 respectively, in FIG. 8d) which are then either directly or through fiber/hollow waveguide delivered to the target, carries some additional advantages. It should be noted, however, the benefit of these advantages can also be realized through the use of an inherently pulsed-source (i.e., a source that emits pulse train rather than CW emission) as long as the source pulse repletion rate is larger than the requirement of the present invention and some of the pulses in the source's pulse train can be deflected out of the pulse train and manipulated to be brought to adjacent locations on the target in a manner described bellow.

Figure 8F:
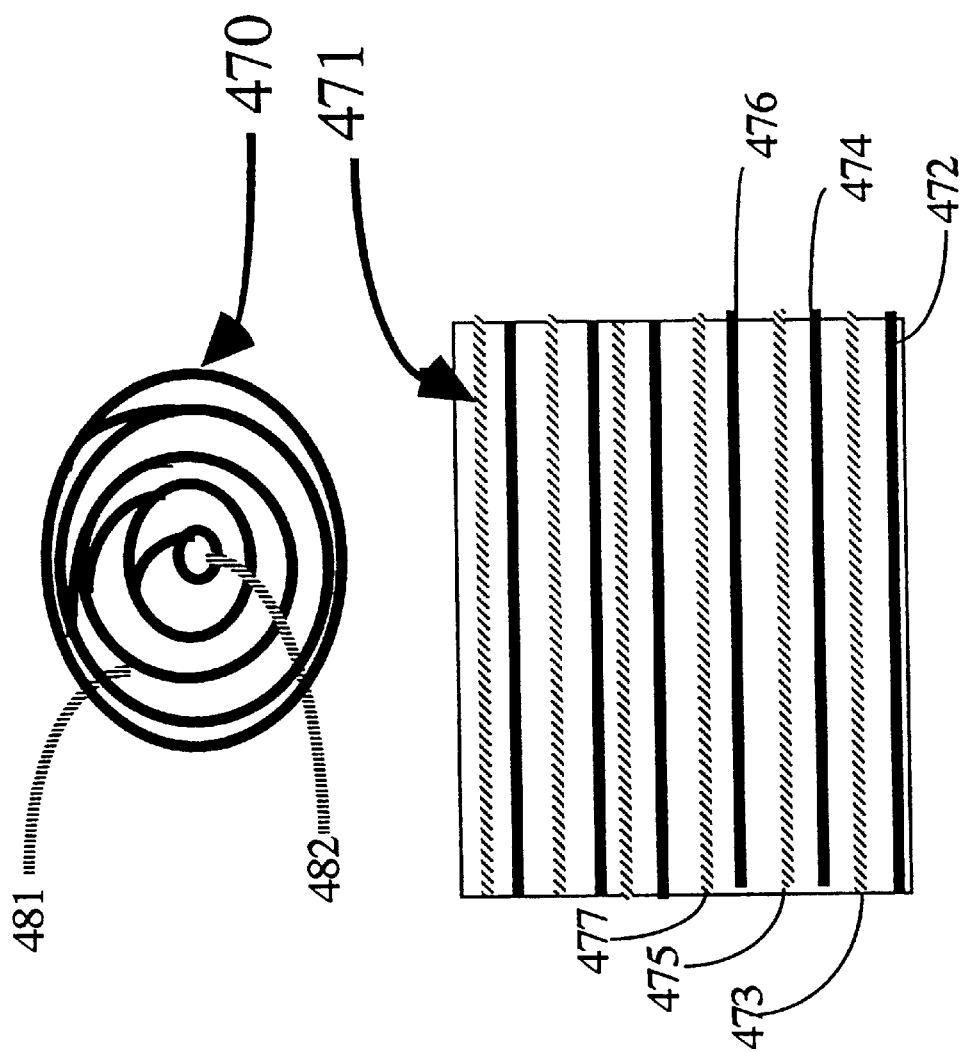
FIG. 8f, is a graphical representation of methods for partitioning a multiple beam output so that the time delay and spatial displacement between individual spots further enhance ablative interaction and material modification and to further enhance removal of residual thermal energy.

By arranging the fibers output (for example the fibers 459 of FIG. 8e), or the focused beamlets (for example, the beamlets 435 in FIG. 8c) in a spiraling manner 470 of FIG. 8f the deposition of thermal energy in the tissue can thereby be minimized. Starting to couple the continuously emitting CW source beam 340 to the fibers/beamlets which deliver energy to the center and then proceeding to the fibers/beamlets that deliver energy to the outward locations, subsequent fibers/beamlets ablation actually REMOVE heat generated by earlier shots in the central, already fired fibers/beamlets. In addition, the laterally diffused energy can be used to enhance material ablation and minimize energy and power requirement for the interaction of these subsequent, laterally displaced pulses.

Such spiraling fibers/beamlets arrangement can be enhanced by varying the time separation 449 between sequential pulses (for example between pulse 444 and 446 in FIG. 8d) so that 449 become shorter for pulses directed towards fibers/beamlets at external perimeter of the spiral 481, and 449 is longer for the internal region of the spiral 482. This, in effect, will translate to an increased firing rate from fibers/beamlets on the outsider of the spiral where there is larger linear circumference to be covered and, therefore, the diffusing heat is more effectively encircled, encased, and ablated away.

Similarly, the same sequential distribution of source energy described herein, can be used for non-ablatively modifying a tissue in accordance with the principles of operation of the present invention (that is modifying the target material irreversibly but not ejecting or removing material from the target). Here, the adjacent fibers/beamlets can make use of thermal energy diffusing from earlier, adjacent pulse interactions to enhance to material modification and minimize energy and power requirement for the interaction.

Another preferred embodiment utilizes an alternating rows arrangement shown in FIG. 8f. Alternative fibers in subsequent adjacent rows (for example, 472, 473, 474, and 475 in FIG. 8f) firing in alternating order with respect to each other. Such sequential ablation will also help eliminate at least some of the residual left-over thermal energy generated in the target through the interaction of earlier pulses.

Note that a 10 ms delay between adjacent fibers outputs translates to a thermal diffusion length of about 100 $\mu$m. Thus, a single 100 $\mu$m fibers positioned adjacent to one that was fired 10 ms earlier, would be perfectly positioned to capture the entire heat which has diffused laterally form the first fiber.

In another preferred embodiment the beam from a very high pulse repetition rate source 314 in FIG. 8c, is focused down to 100 a spot size on the target sufficient to allow the generation of power densities in accordance with the requirement of the present invention, and this focused beam is then scanned across the target. The scanning is done in such a way as to allow lateral heat removal in accordance with the principles described above for multiple beamlets. The scan timing is then synchronized to ablate heat as it diffuse within the targeted area as was described in the previous paragraphs.

As pointed out above, the effective pulse repetition rate (PRR) in each fiber/beamlet is the inverse of the time separation 445 before the beam modifier 424 of FIG. 8c switch another segment of the CW beam 440 into that same fiber/beamlet. Such PRR can reach up to a few hundreds KHz in accordance with the requirement of the present invention. The power requirement for such PRR can be satisfied with CW source of as little as about 1 W average power. Such small (and even smaller) power requirement can be used because utilizing a small spot size fibers/beamlets of 100 $\mu$m or less, achieve peaks power in excess of $10^{+4}$ W/cm$^2$ which are sufficient to initiate ablative interactions. Significantly, many practical commercially available continuously emitting sources can achieve average power level in access of hundreds of kilowatts and even megawatts.

For many practical situations, the spot size of each fiber/beamlet should be on the order on the order of about 100 $\mu$m (or less) so that the peak power per unit area is on the order of about $10^7$ W/cm$^2$. Such power densities have been shown by the inventor to easily result in effective and efficient ablation material removal.

An area of 10×10 fibers (i.e., 100 fibers) will create an Effective Spot Size of about 1 mm$^2$ less fiber or more fibers can of course change the size of the Effective Spot Size.

An additional advantage of this "time sharing" high average beam source is that the many spots cool faster. This is because at the smaller sizer of the many spots size, corresponding to the many fibers/beamlets, three dimensional heat transport dominates. Such three dimensional heat transport and cooling is much more effective at cooling the many targeted spots than a single large spot size whose area is equivalent to the sum of the many spots of the fibers/beamlets.

An additional advantage of this preferred embodiment is that utilizing a continuously emitting CW source (for example, diode laser, diode arrays, COWP2 or high power solid state laser) can be considerably less expensive and much easy to handle in a wide range of environments.

Finally, the output of many of the systems described above can be further modified to shift their output wavelength. Such shifting can be towards the shorter wavelength through the us of non-linear crystals. Such crystals are made of, for example, a thin potassium di-deuterium-phosphate (KD*P) crystal or other non-linear crystals such as KTP. They allow frequency doubling, tripling, quadrupling etc. and allow generation of much shorter wavelength. To achieve longer output wavelength, optical parametric oscillators and optical parametric amplifiers can also be used to tune the output beam wavelength to a longer wavelength of up to about several micrometer. Shifting of the output to the wavelength range of 0.8 $\mu$m to 11 $\mu$m may be particularly beneficial.

Such wavelength tunability achieved through the action of output beam modifiers 326 of FIG. 8b, allow selection of more highly absorbed wavelengths which, in turn, increase the power density deposited within the targeted material according to the principle of operation of the present invention. The pulse output characteristics of such output wavelength tuning device will (except for shifting the wavelength) frequently be similar to those of the original input devices and can, therefore be selected to completely conform to the requirement of the present invention.

The described preferred embodiments can also apply to Longer wavelength such as those from about one to eleven micrometer. This wavelength range possess several high absorption peaks (for example at 2.1 and 2.7 $\mu$m, at 2.94 $\mu$m for Er:YAG and at 9.6 $\mu$m and 10.6 $\mu$m for $CO_2$). These wavelengths can be delivered through Hollow waveguides, through silver halides and through Zichronium or Sapphire fiberletes much like the embodiments that was described above. Lasing in the infrared where the absorption is very high and penetration very shallow shall help to increase power density per unit volume in accordance with the requirements of the present invention.

One such embodiment may involve delivering the infrared beams for most of the way through articulated arm and then at the end have a series of fiberletes in a fiber bundle configuration in accordance with principles of the invention as described above. These small fiberletes can be disposable and because they are used for only a short distance—made of relatively higher loss material such as glass or fused silica. As long as the small focusing for overall high power density per unit volume is achieved at the target, favorable results according with the practice of the invention can be obtained.

Figure 8G:
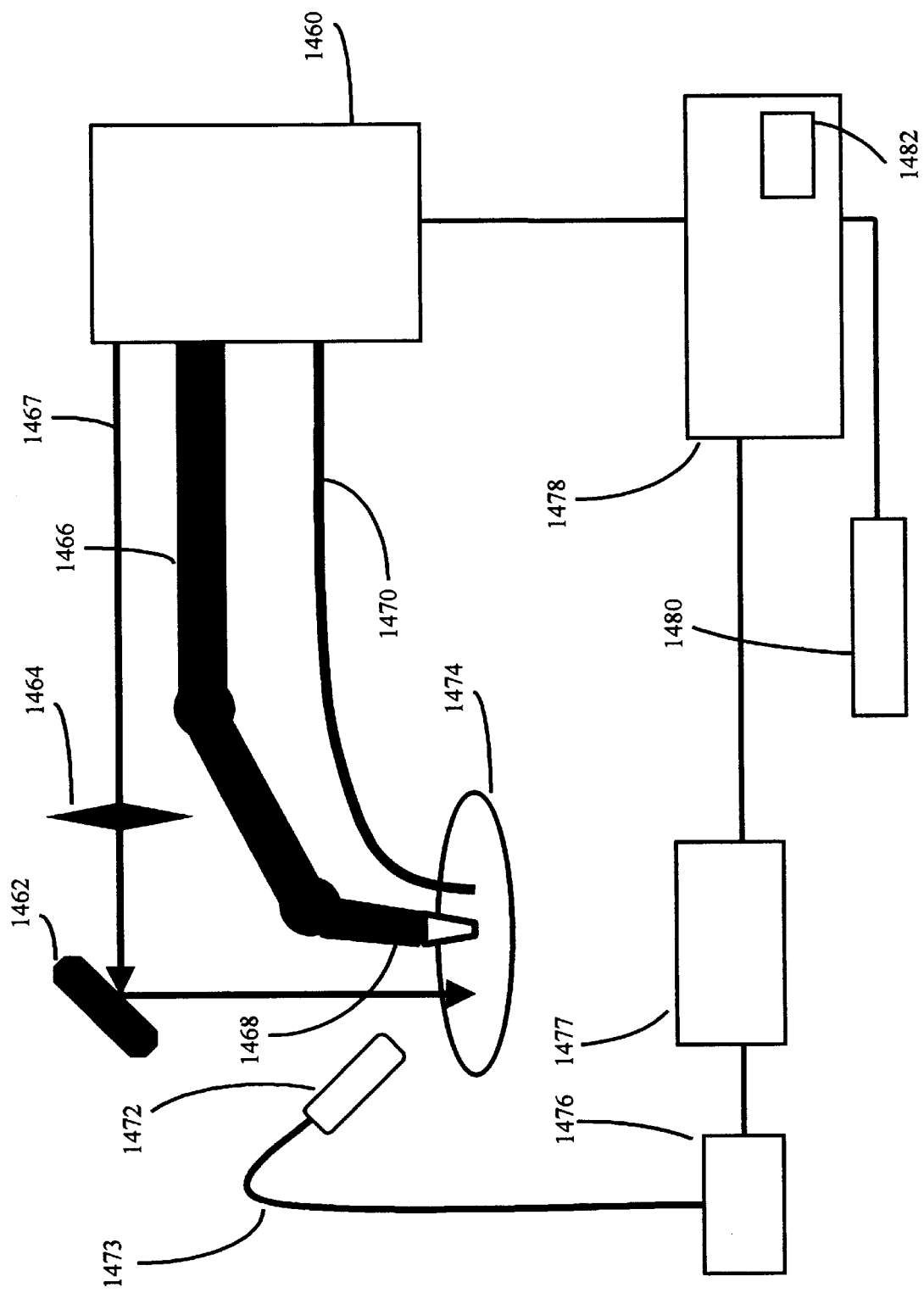
FIG. 8g, is a simplified block level schematic diagram of an exemplary material processing and modification apparatus, equipped with delivery, monitoring, feedback, and control devices, and incorporating a variable pulse repetition rate in accordance with the requirements of the present invention.

Turning now to FIG. 8g, there is depicted a simplified block level schematic diagram of a material removal apparatus (for example, a dental drilling system or a ceramic cutting instrument) incorporating a variable repetition rate laser system 1460 in accordance with the present invention. The material removal apparatus further includes an OPO, KDP, KTP, etc., an optical delivery system, for directing the laser beam to a specific area of a material target. The optical delivery system depends on the design parameters of the material removal system and may alternatively comprise a fiber optic cable 1470, an articulated arm 1466, or an open beam delivery system 1467, including reflectors 1462 and lenses 1464 to focus the beam. A handpiece 1468 is indicated as attached to the distal end of the articulated arm 1466, to allow a dentist, a clinician, or a machinist to maneuver the beam into close proximity with a material target 1474. The handpiece 1468 may also be fitted onto the distal end of the optical cable 1470, to allow the cable to be more easily manipulated.

A laser controller 1478 is connected to the laser system 1460, and controls the activation of the laser, as well as the pulse repetition rate, in response to control signals provided by the operator. An on-off switch 1480 (a foot pedal or alternatively, a hand switch) is-connected to the laser controller and provides laser activation signals in response to the dentist or clinician's depressing the switch. Likewise, a pulse repetition rate controller 1482 is also connected to the laser controller and may be provided as a rheostat control which increases or decreases the pulse repetition rate of the laser system in response to the clinicians turning the knob.

A feedback analyzer 1476 and a feedback transducer 1472 operate in conjunction with the laser to allow precise control of ablation end points. Because many embodiment of the variable repetition rate laser system of the present invention involve plasma generation during the material removal process, material-type-differentiation diagnostics and/or tissue-type differentiation diagnostics can be performed on the material target region based on the material own spectroscopic luminescence emission signatures.

In this case, feedback transducer 1472 is provided in the form of a spectroscope which further includes a collection fiber 1473 for collecting emitted light from the plasma generated by the removed tissue. The light is dispersed and analyzed by the feedback analyzer 1476, preferably an intensified, gated, optical multichannel analyzer/spectrograph. Emission peaks characteristic of different tissue types, e.g., dentin, enamel, and pulp, and different tissue states, e.g., diseased versus normal, are compared to reference data contained within the analyzer 1476. When tissue characteristics change, a feedback signal is provided by the feedback analyzer 1476 to the laser controller which then either reduces laser pulse repetition rates or ceases laser delivery in response.

Alternatively, the feedback transducer 1472 may be provided in the form of an optical coherence tomography head, suitable for performing crater depth diagnostics on the material target. As the laser system is ablating material, the depth of the ablation crater is monitored continuously by the optical coherence tomography head. Crater depth data is provided to the feedback analyzer 1476 which, in turn, may be programmed to issue a feedback signal to the laser controller 1478 and, thus, stops laser delivery when a predetermined crater depth is reached.

The feedback transducer 1472 may also be provided in the form of an infrared detector (for example, an InSb detector, or a HgCd infrared photodiode), or an infrared detector array or an infrared camera head, suitable for performing evaluation of spatial and temporal temperature distribution diagnostics on the material target. As the laser system is ablating material, the temperatures at the vicinity of a predetermined boundary is monitored continuously by the optical infrared thermograph head. Temperature data is provided to the feedback analyzer 1476 which, in turn, may be programmed to issue a feedback signal to the laser controller 1478 and, thus, stops laser delivery when a predetermined temperature is exceeded at a pre-assigned location.

The most common application of the apparatus will involve foot-pedal operation by a dentist, a clinician, or a machinist, who first determines and sets the pulse repetition rate and who then starts and stops laser operation on the basis of a visual examination of the target tissue and evaluation of the progress of the procedure. Thus, it can be seen that the apparatus is suitable for performing many different dental procedures including the elimination of carious lesions, removal of stains on the outer tooth surface as well as stained embedded within the inner regions of a tooth, and tooth desensitization. Using the apparatus in combination with various feedback devices allows the dentist or clinician to perform various delicate and difficult procedures including the ablation of enamel, dentin, diseased soft gum tissue as well as diseased nerve tissue in endodontics procedures without fear of damaging healthy pulp or nerve tissue.

Although the high repetition rate systems of the present invention has been described in connection with an exemplary material processing and dental drilling application, it will be clear to those having skill in the art that the laser system has operational characteristics that are suitable for a very wide range of material removal applications. For example, in the treatment of ear, nose and throat disorders, volumetric material removal is required in various surgical procedures, such as middle ear bone surgery, cholesteatoma, skull and jaw bone surgery, selective removal of malignant tissue, and tympanic membrane surgery. Many of these procedures require the operating physician to have a very deft touch because the structural features of interest are in very close proximity with one another. In addition, because of the proximity and delicacy of the structure associated with such procedures, great care must be taken to process only the target tissue and avoid damaging anything else.

Thus, it can be seen that the characteristics of the laser system of the present invention would be eminently suitable for application in such surgical procedures. In addition, the laser system of the present invention is suitable for use in the field of burn debridement. Skin resurfacing and burn tissue removal are particular applications to which the plasma-mediated pulse high repetition rate laser may be applied. The precision of material removal of the present invention is derived from the fact that only a thin layer of material is removed per laser pulse. By controlling the number of pulses, a surgeon controls the amount of material that is removed. The application of this removal method to burn debridement, in combination with a tissue-differentiation diagnostic feedback apparatus would allow very precise texturizing of the skin surface. By either dithering where the laser beam is directed, by rasterizing, or by controlling the laser beam profile, a clinician is able to sculpt into a pre-defined texture.

Additional procedures in which the laser system of the present invention is suitable include arthroscopic surgery, including partial neniscectomy, synovectomy, chondroplasty, cartilage and tendon removal, and micro perforation, resurfacing, and texturing of cartilage, tendon and bone material.

From the foregoing, it can be seen that the present invention provides an apparatus and method for fast, efficient, precise and damage-free biological tissue removal, including a pulsed laser system having pulse durations on the order of from about 3 fs to about 10 ms. The invention requirement on the ratio of per-pulse material removal depth, duration of the laser pulse, and pulse repetition rates in cases where larger volume removal is required, is such that there is minimal transfer of energy from the beam to the target material lattice in the form of thermal energy. As pulse duration becomes shorter, and/or if absorption and power densities become sufficiently large, multiphoton and/or collisional ionization produces a plasma which ablates from the target surface in the time period between pulses. When operating with short pulses, high absorption, and high power densities, energy deposition is localized in a small depth and ablation occurs before significant thermal conduction can take place in the material. While the depth of material removed per pulse is generally small in the practice of the invention, the minimal thermal and mechanical effects associated with plasma mediated ablation allow operation of the laser system at a high pulse repetition rate which, in turn, achieves high material removal rates.

Figure 9:
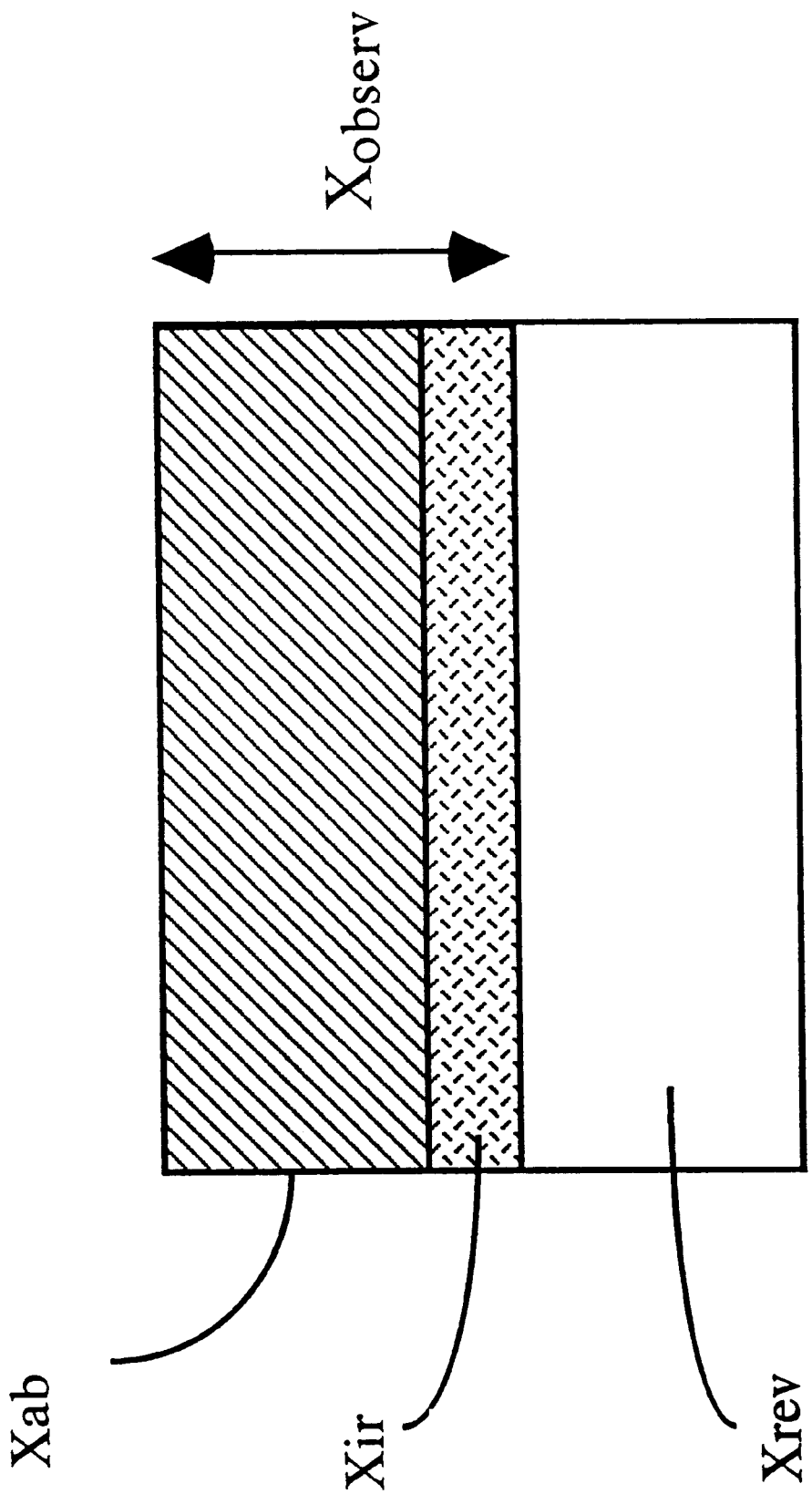
FIG. 9, is a graphical representation of the zones of energy deposition within a target material generated through incident beam-target interaction.

Summary of Principles of operation: High Ratio of Ablation Volume to Permanently Modified Volume To further clarify the issues involved in minimization of the zone of thermal damage generated by each pulse, let us consider the following regions as depicted in FIG. 9.

The energy of a beam of light coming form above will crate three principle regions:

1. The outer layer of $X_{ab}$ is ablated which is ejected away;
2. The middle layer of $X_{ir}$ is the zone of irreversible damage—usually thermal (i.e., zone of Coagulation, charring and/or Melting; and
3. The lower region $X_{rev}$ is the zone where light and energy has penetrated and been felt but only in a reversible way.

The combined depth of region Xab+Xir is termed $X_{observ}$ which is the only volume with observed effect.

Figure 10A:
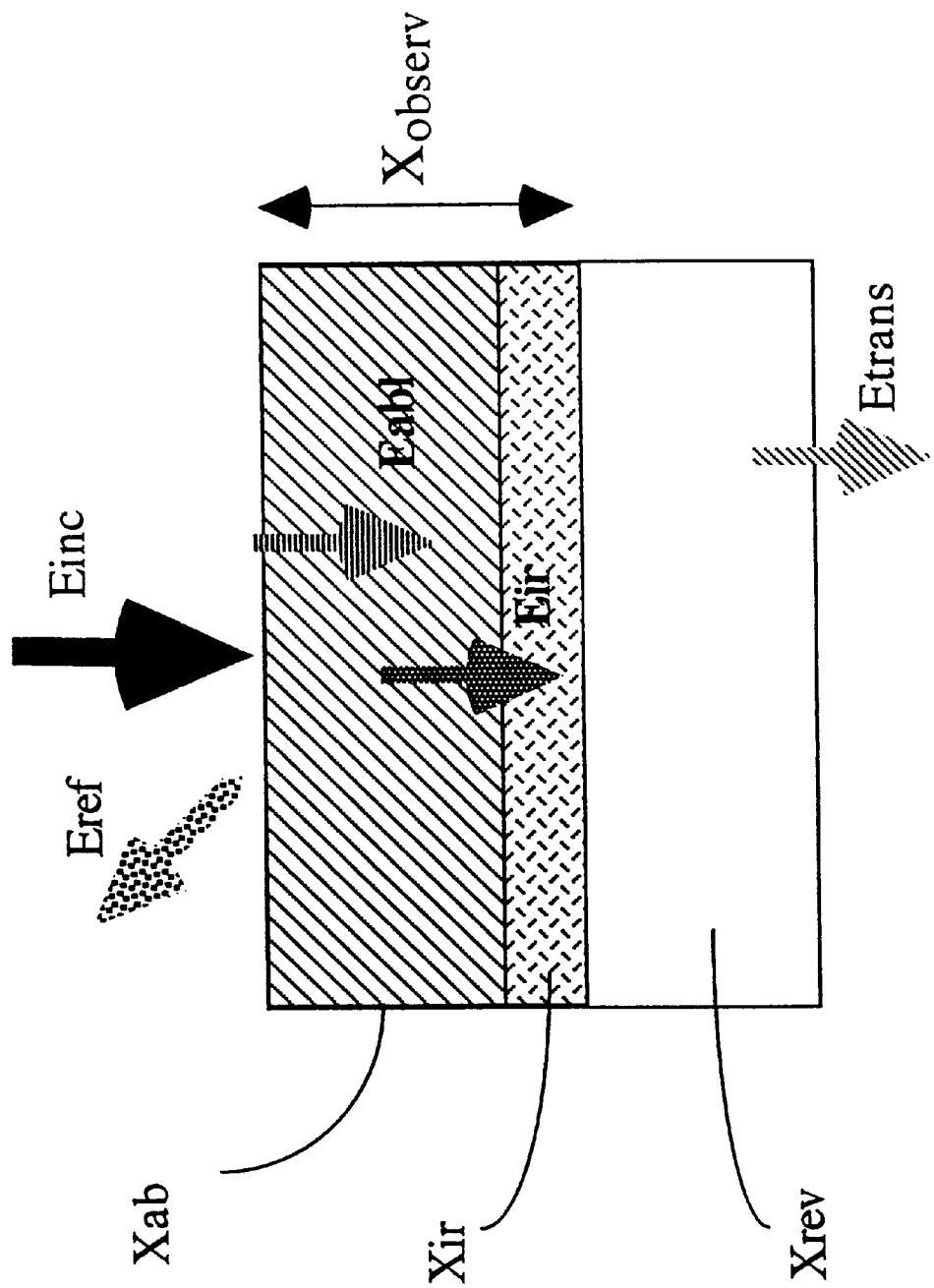
FIG. 10a is a graphical representation of the incident beam reflection and transmission as well as the partition of deposited energy within the three zones of interaction effects described in FIG. 9.

FIG. 10a defines the energy components involved in the interaction. The energy components are the incident electromagnetic energy ($E_{inc}$), the transmitted electromagnetic energy ($E_{trans}$), the reflected electromagnetic energy ($E_{ref}$), as well as Ec, the converted electromagnetic energy now appearing as chemical, acoustical, and thermal energy components generated by the interaction and used for altering the material properties, removing and ablating a portion of the material and energizing the ablated products.

We designate the energy components used for removal of material is shown in FIG. 10a as $E_{abl}$, while the energy left in the unablated tissue and used to irreversibly alter the material is shown in FIG. 10a as $E_{ir}$. It is also possible to define what may be called "the observed energy" Eobs, i.e,
the energy whose effect can be detected by observing the ablated material after the interaction energy is $E_{abs}$ and is equal to the sum of the energies used for ablation and to irreversibly altering the tissue. Thus $E_{obs}=E_{abl}+E_{ir}$. The sum of all the energy components forms the energy balance for the interaction: $E_{inc}=E_{ref}+E_{trans}+E_{abl}+E_{ir}+E_c$.

When the energy $E_{inc}$ from a single pulse impinges on the material, much of the material may experience transient effects of the incoming energy. Unfortunately, the entire depth of energy deposition can not always be measured. While it is possible to place a thermal, optical or mechanical detectors within the affected portion of the target to observe the transient energy effect, by our definition of Xrev—the zone of reversible energy effects, no permanent alterations remain.

The portion of the energy traversing the material without leaving irreversible damage (for example light energy propagating through the material and/or thermal energy diffusing down the material but which does not raise the material temperature above, for example, 50° C., cannot easily be detected (certainly not after the interaction has been completed).

Consequently, it is convenient to quantify the above requirement by considering only the readily observable, measurable quantities:

$$X_{obs}=X_{abl}+X_{ir} \quad (3)$$

Here, $X_{abl}$=the ablated material depth and, $X_{ir}$ is the zone of permanent, irreversible damage of material which has not been ejected from the bulk.

$X_{obs}$ is, thus, the depth of material in the tissue to which, as a result of a single pulse action, observable, irreversible changes have occurred. Thus, characterization of the interaction in terms of observable, measurable quantities ($X_{abl}$ and $X_{ir}$) is achieved. According to the practice of the invention, the objective is to maximize $X_{abl}$ and minimize $X_{ir}$.

The depth of the two zones and the ultimate size of $X_{obs}$ are a consequence of two factors: the energy deposition depth, and the energy distribution profile of the incoming energy.

The energy can arrive at the effected volume of depth $X_{obs}$, either through direct optical deposition, or through subsequent thermal diffusion of energy.

Unless heat deposition or coagulation are actually desired, the ideal surgical result is, a situation where $X_{ir}$ approach zero (Xir→0) and $X_{abl}$ approaches $X_{obs}$.

In reality, this is impossible as some (even if very small) narrow layer of modified material will always be left behind. It is virtually impossible to design an interaction where the energy deposition is so finely distributed that the deposited energy density $\epsilon$ (x) is sharply cut off as in a step-function.

Thus, it is useful to quantitatively define the requirement in terms of the invention's practical needs: For most biomedical and some industrial/micro-processing tasks a zone of $X_{ir}$ on the order of 1 $\mu$m is acceptable.

The term "on the order" is generally meant to imply from a single to a few micrometers, i.e., 1 to 9 $\mu$m).

The zone $X_{ir}$ is most often modified through thermal effects (although mechanical and chemical alterations must also sometimes be considered). For simplicity let us concentrate on this thermal energy form of material-modification where the zone of thermal modification is on the order of 1 micrometer.

Permanent thermal modification (but not ablation) in soft tissue will occur if temperature rises are less than 100° C. Temperature rise above this level will result in vaporization, explosive vaporization, and ablation.

In hard tissue (e.g., enamel, bone and dentin) melting of hydroxyapatite occurs at temperatures greater than 900° C.

To calculate the energy requirement for material modification consider the following:

In Soft Tissue:

(Consider a exemplary skin tissue with a permanent thermal modification of $\mu$m.

In this case the increase from body temperature, $\Delta T$, is:
$\Delta T = \Delta T = 100 - 37 = 63°$ C.

and the temperature rise, $\Delta T$, must be smaller than 63° C. to avoid irreversible material modification.

Thus, $\Delta T < 63°$ C.

Now, from Thermodynamics:

$$\Delta E = m \, C \, DT$$

Where m is the effected mass C is the specific heat capacity and $\Delta T$ is the temperature increase, or, units $m = \rho \Delta v = \rho A_{beam} \, dz$ $$\Delta E = \rho A_{beam} \, C \, dZ \, DT \tag{4}$$

Where $\rho$ is the material mass density, $\Delta v$ is the modified volume, dz is the depth of the modified volume, $X_{ir}$, and $A_{beam}$ is the area of the beam Dividing equation 4a by the area we get on the left hand side the increase in Fluence (fluence is the energy per unit area) $\Delta F = \Delta E / Area$.

And with the depth of the considered altered zone—$\Delta Z = X_{ir}$, and C of water=4.35 KJ/(Kg K°)

then equation 4 becomes, $$\Delta F = \rho Xir \, C \, DT \tag{5}$$

With $X_{ir}$ assumed on the order of 1 $\mu$m and $\Delta T < 63°$ C. required to achieve coagulative damage to the tissue, fluence needed is less than, $\Delta F < (1 \text{ g/cm}^3)(0.001 \text{ cm})(4.35 \text{ kj/kg K}°)$ or $\Delta F < 277.2 \text{ E}^{-4} \text{ J/cm}^2 = 0.027 \text{ J/cm}^2$ i.e., $\Delta F < 0.027 \text{ J/cm}^2$ Or, for an exemplary 0.5 mm Diameter beam, the energy required to modify a 1 $\mu$m thick soft tissue is, $\Delta E < 0.05$ mJ.

With typical incident Energy $E_{incidence}$, ranging from $0.3_{mJ}$ (at threshold for hard tissue ablation) to energy on the order of 15 mJ, the ratio of the required-energy for 1 $\mu$m zone of modification to incident pulse energy.

---

DE/DE$_{incidence}$ =
17% @ Threshold Energy 0.3 mJ
1.7% @ typical ablation Energy of 3 mJ, and,
0.17% @ higher fluence of 15 mJ

---

Again, note that the percentage mentioned, are the percentage of the incident Energy.

Figure 10B:
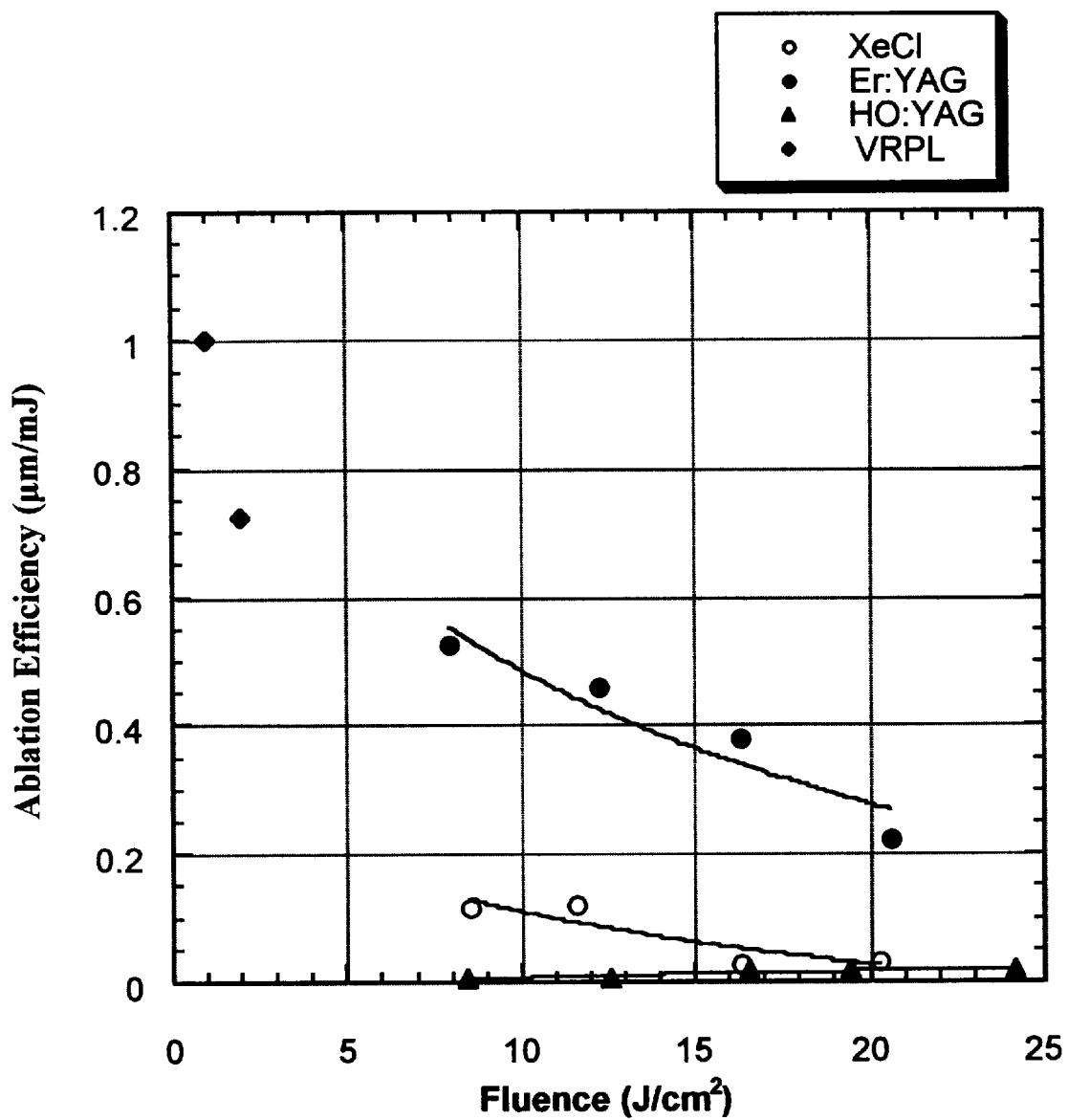
FIG. 10b, is a graphical representation of experimentally determined values of ablation efficiency (the amount of material removed per unit of energy) plotted as a function of pulse fluence for four different laser systems.

Experimentally, (for hard tissue, see FIG. 10b) it is observed that for 350 fs (1.06 $\mu$m) pulses at 1 J/cm2 (i.e., 1 mJ pulses with a spot size of 0.5 mm), it takes 1 mJ to ablate 1 $\mu$m which leaves a region of about 1 $\mu$m irreversibly modified ($X_{ir}$~1 $\mu$m).

Thus, in a 1 mJ short pulse interaction about 7% of the energy is used for permanent tissue modification and the rest is used for ablation, ejection and other energy-consuming components of the interaction.

If a more typical pulse of about 3 mJ is used on a 1 mm dentin slice, experimental data show that about 20–30% of the energy is transmitted, less than 2% irreversibly damage a region of about 1 $\mu$m of tissue, and the balance (about 70%) of the incident energy is responsible for ablation, energizing the ablation products, plasma formation, or released as acoustical and mechanical and other forms of energy.

Er:YAG (2.94 um) interaction yield a smaller percentage since it takes a 10 to 20 mJ per micropulse to ablate 1 to 2 $\mu$m leaving a zone of thermally damaged material of about 1 $\mu$m. Thus, in a 10 mJ micropulse about 0.7% of the energy is used for permanent tissue modification. Also in this case, virtually no energy is transmitted through a 1 mm thick slice, and the vast majority of the incident energy goes into ablation, energizing the ablation products, plasma formation and acoustical and mechanical energy. Since in the Er:YAG interaction 10 to 30 mJ are used to ablate about a 1 to 3 $\mu$m while the interaction of ultrashort pulse require 1–2 mJ to ablate the same amount of tissue, the interaction of ultrashort pulse is more efficient (see FIG. 10b). While Er:YAG interaction devote smaller fraction to material modification and negligible amount is transmitted, a much larger fraction is used to energizing the ablation components, or is released as mechanical and acoustical energy.

With Ho:YAG (2.1 $\mu$m) about 4 mJ per micropulse are required to ablate 1 $\mu$m, (FIG. 10b) leaving Xir of tens of microns of thermal damage. The micropulse energy is 4 mJ and thus about 1.75% of the energy is used for material removal and most of the incoming pulse energy is spread over tens of microns resulting in such deep irreversible tissue modification. In this case a few percent of the pulse energy is transmitted through a 1mm thick slice and most (~80%) of the energy is spread through tens of microns of thermally damaged tissue.

For the XeCl (0.308 $\mu$m) about 10 mJ is required to ablate 1 $\mu$m leaving (FIG. 10b) $X_{ir}$ of tens of microns of thermal damage. The entire 15 ns pulse energy is 80 mJ and in this case perhaps 20–30% of the pulse energy is transmitted through a 1 mm thick slice and 10–30% results in tissue heating. The rest of the energy (40% to 70%) is used for ablation, energizing the ablation products, generating and heating plasma, or used in acoustical and mechanical energy.

Thus, an estimate of about 10% of the energy is used for permanent tissue modification of several tens of microns. This large amount of energy, however, is distributed over a much larger damaged tissue volume.

The above first two examples correspond to small thermal damage $X_{ir}$ zones and high $X_{ab}/X_{obs}$ ratio (from about 0.2 to about 0.5).

The last two examples (Ho:YAG and XeCl) correspond to deeper thermal damage $X_{ir}$ and small $X_{ab}/X_{obs}$ ratio (from about 0.01 to about 0.1).

Further Comments Regarding Principles of Operation: High Repetition Rate

Figure 11:
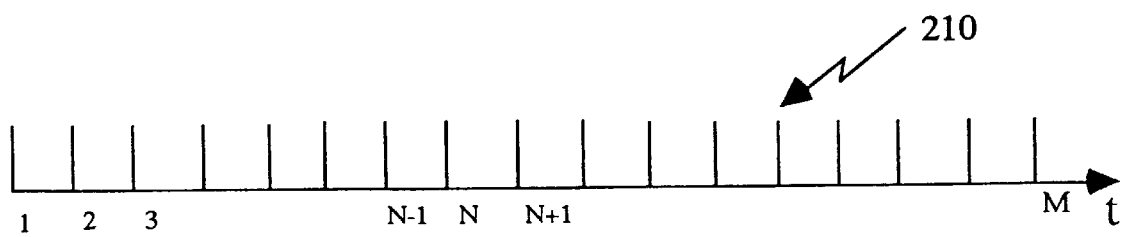
FIG. 11, is a graphical representation of a sequence of incident pulse train, the corresponding time-dependent heat diffusion, and the ablative removal of sections of the heated volume
Figure 11:
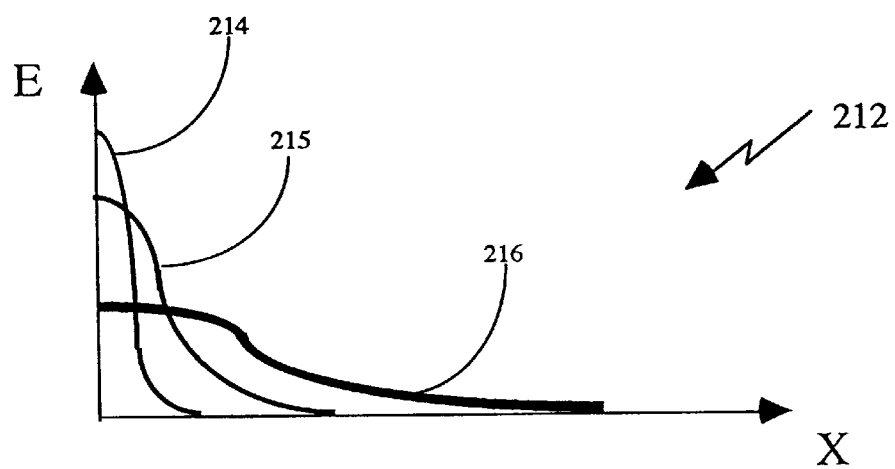
Figure 11:
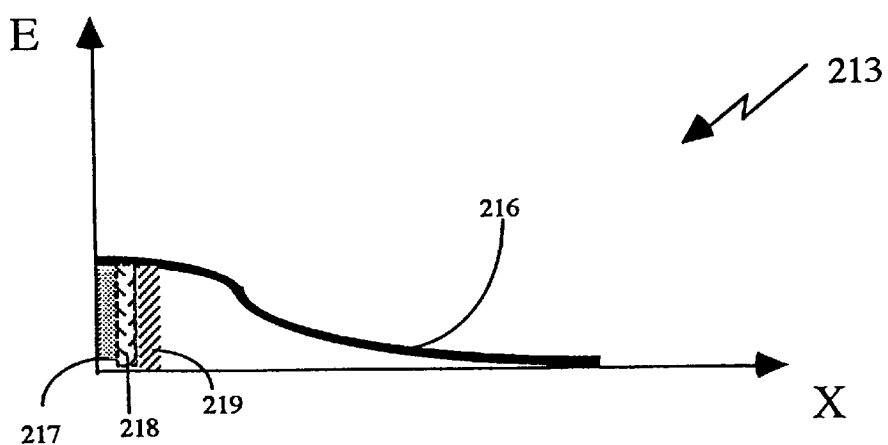

An additional insight of the role, according to the present invention, of high pulse repetition rate operation can be obtained by considering FIG. 11. 210 in FIG. 11 shows a sequence of pulses 1,2,3, . . . N–1, N, N+1 . . . M. This train of pulses is incident on the targeted material (where pulse number 1 is the first pulse to reach the material and the pulse M is the last pulse in the train).

212 shows three exemplary curves illustrating a one-dimensional thermal energy distribution as a function of distance from the target material surface. The curves 214, 215, 216, show that with time, the deposited thermal energy associated with first pulse diffuses into deeper regions (larger X values) of the targeted material. Here 214 represents an exemplary thermal energy distribution following the first pulse energy deposition at t=0+τ (where τ is the pulse duration). If τ is short enough (for example, less than 1 μs in an exemplary water-like material) so that thermal diffusion is negligible (e.g., less than 1 μm) 214 will essentially correspond to the optical energy distribution where optical energy has been converted to thermal energy. The curve 215 is the thermal energy distribution at some later time, and 216 is the thermal energy distribution at a later time yet. The sequence of the three distributions at three subsequent times (for example—100 μs, 1 ms and 100 ms) show the general characteristics of thermal energy diffusion. They show that as the thermal energy penetrates (diffuses) deeper into the material its amplitude is lowered at the surface is reduced (the surface is being cooled) while its amplitude at deeper regions is increased (deeper regions are being heated up).

213 shows the ablative effect of subsequent pulses on the thermal energy diffusion due to the first pulse (N=1). For example, if we consider the last thermal energy distribution 216, the ablative effect of the first pulse N=1 is to remove part of the deposited thermal energy by self-ablating a slab of material 217 of thickness $a_r$. As the energy of the first pulse diffuses further inward, the effect of the following pulse (N=2) is to ablate an additional slab of material 218 also of approximately the same thickness $a_r$ (it is assumed that the ablation rate remain relatively unchanged from pulse to pulse). The third pulse will again remove about $a_r$ of material in 219 while the remaining heat generated by the first pulse N=1 continues to diffuse towards deeper material regions. Clearly, the portion of the thermal energy distribution represented by the curve 216 that is included within the boundaries of 217, 218, and 219, is physically removed with the ejected material and is no longer available for further diffusion and heating of the material.

The penetration depth—as a function of time—of the diffusing thermal energy, after it has been optically deposited near the surface is given by equation 1 above.

We shall also refer to $X_{diff}$ as the location of the thermal diffusion front. The location of the thermal diffusion front as a function of time was illustrated by the curve 220 of FIG. 5a. In FIG. 5a, Equation 1 corresponds to the diffusion front as a function of time 220, which is a curve about the time axis. It demonstrates a very rapid initial heat diffusion which slows down very significantly as time progress.

The linear curves 222, 224, 226, and 228, in FIG. 5a, represent the time-dependent position (or depths) of the ablation front below the initial surface. As can be seen from FIG. 5a, the ablation depths are directly proportional to time and can be described by the linear equation 2 above.

Where the slope of the lines 222, 224, 226, and 228 is equal to ($a_r\nu$), the product of $a_r$, the ablation rate per pulse and the pulse repetition rate ν (nu), the pulse repetition rate. If, for example, for a given laser system a substantially constant ablation rate per pulse (for example 1 μm/pulse) is assumed, then the slope of the curves representing the ablation front of various pulse repetition rates are proportional to the pulse repetition rate, ν. Thus, as can be seen from FIG. 5a, high pulse repetition rate will or a high ablation rate per pulse $a_r$ will yield a steep slope as in 222. On the other hand, a low pulse repetition rate or a low ablation rate per pulse $a_r$ will yield a shallow slope as in 228.

Significantly, FIG. 5a reveals a very important feature of the present invention. If the material processing system is allowed to operate long enough, the depth of the ablation front (or material removal) will ultimately surpass the depth to which heat from the original pulses has reached, and the ablative interaction itself will completely remove any residual heat that was deposited in the material by earlier pulse.

This effect also can be seen in FIG. 11. If pulses N=1, 2, 3, . . . N remove slabs of a relatively constant thickness $a_r$, and do so at a faster rate than the rate of heat diffusion, the sequence of ablation slabs will eventually catch up with and completely eliminate all thermal energy due to pulse 1. If we use 212 in FIG. 11 as an example, the spatial position of the thermal diffusion front increases from 214 to 215 to 216 but the increase in position is slower at later times. Thus, the constant rate of ablation will eventually remove the entire heat deposited by the first pulse (pulse 1).

If we differentiate equation (1) with respect to time, we obtain an expression for the TIME RATE OF CHANGE of thermal penetration depth (i.e., the time rate of change of the position of the heat diffusion front). This expression is given by, $dX/dt=0.5 (K/t)^{1/2}$.

As can be seen from this expression and also from the curve 220 in FIG. 5a, for small values of time t (i.e., earlier times after the electromagnetic pulse energy deposition) the heat diffuses very fast (indeed this rate approaches very large values for very small values of time).

As a consequence, if a sequence of pulses 210 of FIG. 11 is incident upon a material surface, the heat from the most recent pulses will move faster than the ablation front and part of the heat of the most recent pulses will not be removed by later pulses as the system is stopped at some finite time. However, heat from earlier pulses will not diffuse as fast and will eventually be contained within a volume that will ultimately be completely removed by the interaction.

The point can be made clearer by considering an exemplary system operating at 1000 pulses per second for 3 seconds and represented by curve 224 in FIG. 5a. In a water-like material, energy from the first pulse to interact with the sample will diffuse a distance of 1 mm into the material at about 1 second. The ablation front, assuming ablation rates of 1 μm per pulse and 1000 pulses per second, will cut 1 mm of material in 1 second as well. Thus, the point at which the ablation front overtakes the first-pulse heat diffusion front, designated in FIG. 5a as $X_{xo}$, and named by the inventor the "cross-over depth", is approximately at 1 mm depth. The cross-over occurs approximately 1 second after the start of the interaction for an exemplary high water content tissue or material. This point in time is, consequently, maned the "cross-over time" and is labeled $t_{xo}$ and corresponds to the vertical line 230 of FIG. 5a.

Each system, characterized by its pulse repetition rate, by the material heat diffusion rate, and by the specifics of the interactions between the pulse and material (which, in turn, define the ablation rate per pulse), will have its own unique cross-over time $t_{xo}$. An exemplary system with a low pulse repetition rate or low ablation rate per pulse may operate for a long time the ablation front reaches the cross over distance $X_{xo}$. If such a cross over time is very long the ablation front may never reach $X_{xo}$ before the end of the procedure.

This is shown in FIG. 5a by comparing the distance $X_{diff}$ of curve 220 to that of $X_{abl}$ of curve 228 for some exemplary time t. As can be seen in FIG. 5a, the positions given by curve 220 are always of higher value than those given of curve 228 and the system defined by the curves 220 and 229 never reaches a cross-over time.

Since for the line 228 the diffusion front is (for all times shown in FIG. 5a) ahead of the ablation front, not all the heat deposited by the first pulse is removed by the ablation of subsequent pulses during the procedure and some of the heat of even the very first pulse remain in the target material.

The situation is different for the ablation front described by 224. Here, pulses launched after t will ablate material that has not been exposed to the first pulse energy at all, since all the heat of the first pulse has been removed by pulses launched from t=0 to t=$t_{xo}$.

For an exemplary heat diffusion curve 220 and ablation front curve 224, corresponding to an exemplary ablation rate of 1 μm per pulse and pulse repetition rate of 1000 Hz in an exemplary water-like dielectric (e.g., material with water-like characteristics), subsequent pulses (to pulse N=1000) will ablate the entire heat generated by second pulse (N=2), and then additional pulses will remove all of the thermal energy deposited by pulse 3 (N=3), then N=4, etc.

On the other hand, it is equally clear that the heat generated by the very last pulse (N=M) will not be ablatively removed at all since no subsequent pulses follow that pulse.

In the above numerical example (curve 224) of ablation of water-like material (i.e., 1 KHz, and 1 μm/pulse), the situation for the last 1000 pulses is unique. These pulses are characterized by the fact that the time remaining in the irradiation procedure is shorter than the time necessary for the ablation front to overtake their thermal diffusion front position by the time the end of the procedure is reached. An exemplary pulse L (within the last 1000 pulses) interacting with the material a time $t_{lp}$ before the source ceases operation, will have its heat diffused to a position $X_{lp}$, which is deeper than the depth of material removed by the (v$t_{lp}$) pulses left within the time interval $t_{lp}$ before the source ceases operation.

As FIG. 5a shows, however, even these last few pulses have some of their residual heat removed by the subsequent pulses. For instance, in the exemplary 1000 Hz system, if a total of 3000 pulses is applied, pulses just after pulse 2000 will have most of their heat removed by the subsequent, nearly 1000 pulses. On the other hand, pulse number 3000 and the last few pulses in the sequence—will have none or very little of their residual heat removed by subsequent pulses.

Interestingly, the inventor also recognized that the fraction of the deposited heat left by each one of the last 1000 pulses in the exemplary 1000 Hz system, is proportional to the ratio of the distance between the depth of thermal diffusion and the position of the ablation front (i.e., the distance between position $x_{diff}$–Xab), and the total diffusion depth, $X_{diff}$. A more precise analysis of this is provided below. Furthermore, the total amount of cumulative heat not ablated by the exemplary laser system is proportional to the area bounded between curve 220 and the curve 224 to the left of $t_{xo}$. This observation is true because each of the last 1000 pulses send a thermal diffusion front into the material which has the same characteristic diffusion curve 220 of FIG. 5a. As time progresses subsequent pulses will allow the ablation front to reach their respective depth as shown by the linear curves 222 to 228.

By contrast, as we have seen from the discussion above (with M being the last pulse in the pulse train) all the heat from pulses M-1001, M-1002, M-1003, etc., is completely removed by the subsequent 1000 pulses.

As a consequence, in considering the problem of residual heat left in the target material by a train of pulses of sufficiently high repetition rate, only the last pulses—those whose heat is not completely removed by the subsequent incoming pulses—need be considered. For simplicity we shall refer to these last pulses as the "residual-heat pulses".

Figure 12:
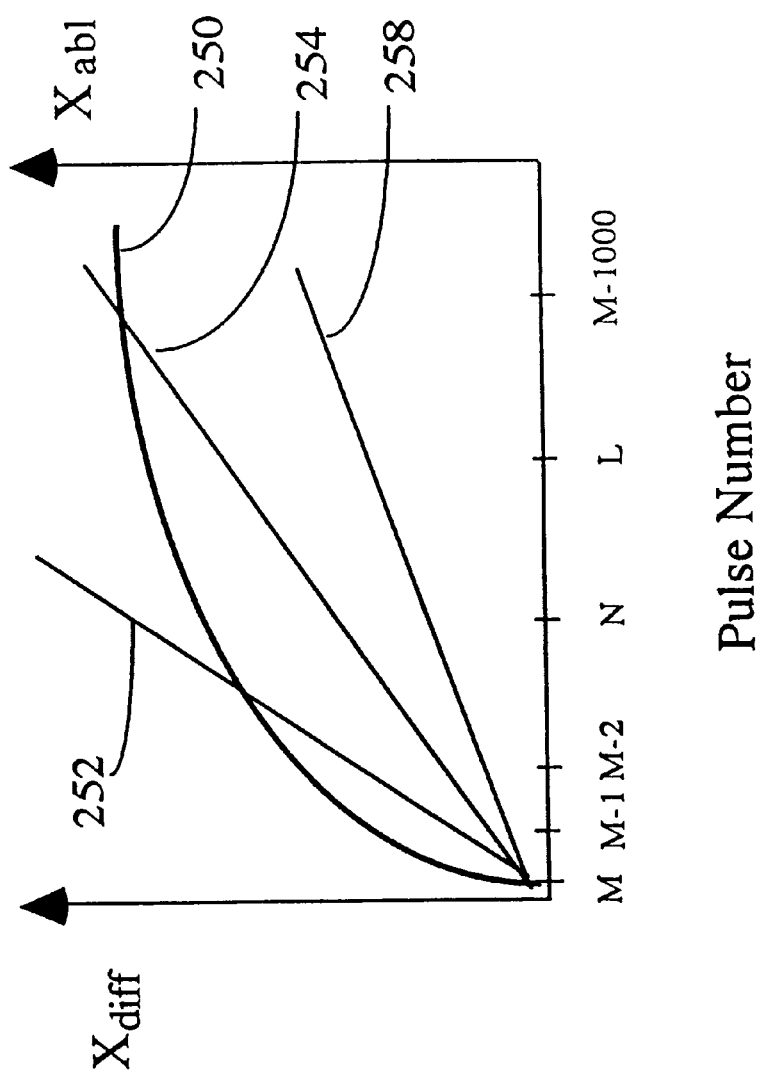
FIG. 12, is a graphical representation—for each one of the last 1,000 pulses—illustrating the spatial location of the thermal energy diffusion front and the ablation front at the moment the source beam is turned off. The illustrated positions of the two fronts are the distances from the location of each pulse deposition to the position of the fronts at source turn-off time.

To generalize the problem it is useful to consider FIG. 12.

While FIG. 12 is visually similar to FIG. 5a it actually differ substantially. In FIG. 12 the horizontal time-axis is replaced by an axis describing the pulse number starting from the last pulse in the pulse-train under consideration, M, and ending in the last pulse whose heat is completely removed (in our exemplary 1000 Hz system it is Pulse M-1000). Thus, in FIG. 12, the curve 250 represents the locations of the heat diffusion fronts of the diffusing thermal energy deposited by pulse M, M-1, M-2, M-3, . . . N, . . . to M-1000, at the time that the source is turned off and the pulse-train is terminated.

The exemplary curve 254 of FIG. 12, on the other hand, represents, for each pulse, N, the depth of material ablated by the subsequent pulses M–N which follow the pulse N (and thus, the depth of material removed by the number of pulses remaining in the train and following each pulse N, (where M>N>M-1000).

The curves 252 and 258, correspond to pulse trains with, respectively, higher and lower pulse repetition rates.

To simplify the analysis we make an assumption that the energy density in the tissue is uniformly distributed throughout the volume of material where incident electromagnetic energy is being deposited. This assumption is clearly not correct and, instead, represents a worst-case situation. Normally optical deposition does not behave like a "step function" where energy is uniformly distributed throughout some penetration depth.

(i.e., a step—function distribution is given by, $\epsilon = \epsilon_0$ for X<$X_0$ and $\epsilon = 0$ for X>$X_0$)

Instead, an actual electromechanical energy deposition follows some exponential decays (for example, Beer Law) where the beam intensity falls off according to an expression such as I=$I_0$ e−(x/δ).

Similarly, as FIG. 11 illustrates, that the thermal diffusion front at any given time also drops-off according to an exponential decay and does not progress as a step function.

Our simplification, however, assumes that the source's deposited energy is distributed uniformly (as in the step function described above) throughout the material volume where the incident energy was deposited. This volume is given by the product of the beam spot size, A, and the thermal diffusion front position $X_{diff}$.

V=A $X_{Diff}$

Thus, the one-dimensional energy density, as a function of depth into the tissue X, and time, t, since the pulse energy was deposited in the tissue is simply given by:

$$\epsilon(X,t) = E_0/(A\, X_{Diff}) \qquad (6)$$

Where $\epsilon_0$ is the total incident pulse energy. Since our goal is to calculate the residual single pulse energy and residual total energy left in the tissue (i.e., the fraction of the incident energy which will actually thermally damage the tissue), and since more energy is actually concentrated in the shallower layers of the material than in the above assumption of a step function deposition, the above approximation represents a worst-case scenario.

Given the above, the amount of energy left in the material ($E_{Io}$) at the end of the pulse train, due to the energy deposition of the (single) $N_{th}$ pulse and after the removal of the heated material by pulse M–N through M (where M is the last pulse in the train), is given by the product of the energy density and the remaining heated volume:

$$E_{lo} = \epsilon(X,t) \, A \, (X_{diff} - X \, abl) \quad (7)$$

Again, $E_{lo}$ is the total left-over energy due to the Nth pulse (a single pulse) with incident energy $E_0$.

Substituting from the expression for the energy density $\epsilon(X,t)$ from equation (6) we have:

$$E_{lo} = (E_0/(A \, X_{Diff})) \, A \, (X_{diff} - X_{abl})$$

Which translates to:

$$E_{lo} = E_0(1 - X_{abl}/X_{diff}) \quad (8)$$

The total amount of energy left over is the tissue is just the sum over the energy contributions $E_{lo}$ from each one of the M-1000 last pulses in the ablating pulse train. i.e., $$E_{total-LeftOver} = E_{TLO} = \sum (E_{lo}) \quad (9)$$

For example, in the case of a 1000 Hz system ablating a water-like substance, we sum from pulse N=M-1000 to pulse N=M.

A more general expression can be formulated if we consider that the last pulses in the pulse train (see FIG. 12) i.e., those pulses in the train whose energy will not be completely removed, are the pulses contained within a time interval equal to the cross-over time prior to the end time of the pulse train. (Again, this is so because, by definition, this is the time duration required by subsequent pulses in the train to ablate the entire energy deposition of a single pulse).

To get the total amount of left-over energy, we substitute the expression for a single-pulse left-over energy, $E_{lo}$, from equation (8) into equation (9) and replace the summation over the last few individual pulses that leave residual energy in the material by an integration over the corresponding time interval.

Since the total number of pulses in a pulse train of pulse repetition rate $\nu$ in an interval of time t is given by, (# of pulses)=$\nu t$, and since an increment of d (# of pulses) is given by $d(\nu t) = \nu dt = (\nu \, dt)$, (because in this discussion the pulse repetition rate, $\nu$ is held constant with respect to time). Thus, the summation over the last pulse in the train that contribute to the left-over thermal energy (i.e., the summation over (# of pulses)), becomes an integration over time, i.e., $$\sum \rightarrow \int \nu dt$$

and from equation (8) and (9) we obtain the integral expression, $$E_{TLO} = E_0 \int (1 - X_{abl}/X_{diff}) \nu dt \quad (10)$$

Where the integration is carried out over the time interval from t=0 to t=$t_{xo}$ Substituting the values for $X_{diff}$ and $X_{abl}$ from equation (1) and equation (2) and integrating, we obtain the general expression:

$$E_{tlo} = E_0 \nu t_{xo}[1 - (2/3)a_r \nu (t_{xo}/k)^{1/2}] \quad (11)$$

Where $a_r$ is the ablation rate per pulse (e.g., micrometer per pulse).

If, for example, the 1000 Hz system interacting with a water-like substance is considered, $t_{xo}$=1 second and equation (11) is reduced to, $$E_{tlo} = E_0 \nu [1 - (2/3)a_r \nu (1/k)^{1/2}] \quad (12)$$

In general $t_{xo}$ for a given system can be found by setting $X_{ab} = X_{diff}$ which yields $$t_{xo} = k/(a_r \nu)^2 \quad (13)$$

substituting (13) in (11) we obtain, $$E_{tlo} = (1/3)E_0(k/\nu)1/a_r^2 \quad (14)$$

Note that by dividing and multiplying by $\delta^2/\delta^2$. Equation 14 can also be written as:

$$E_{tlo} = (1/3)E_0(k/\nu)1/f^2 \quad (15)$$

Where:

$f = a_r/\delta$ the ratio of ablation rate to optical deposition depth.

Equation 14 provides some important insight regarding the amount of left-over energy in the tissue and its relation to the important parameters $E_0$, k, $\nu$ and the ablation rate $a_r$ (or the ratio of ablation depth per pulse to optical deposition depth, f).

From equation (14) it can be seen that the total left-over energy $E_{tlo}$:

Increases with the incident pulse energy $E_0$

Increases with increased thermal diffusivity k (since more energy is able to escape ablative removal by being conducted to deeper layers of the material).

Drops with increase pulse repetition rates are able to catch up and ablate more material. (Note however that from equation (8), for small values of $t_{xo}$, small values of $a_r$ or large values of k, $E_{tlo}$ will initially increase with $\nu$ and only later, after reaching a maximum value of left-over energy will begin to decrease again with increasing pulse repetition rates, $\nu$. A more detailed discussion of the dependence of $E_{tlo}$ on the laser pulse repetition rate is provided below.)

Drops with increased ablation rate per pulse, $a_r$, (or f) as the square of these quantities. (Again, this makes sense since a larger ablation per pulse leave less residual energy in the material and thus the smaller Etlo is.)

Another interesting observation is that from equation (11) the ratio of the total left-over energy to the total incident energy impinging on the sample between the time $t_{xo}$ prior to the end of the pulse train and the end of the pulse train is a constant and is equal to 1/3. This is so because the Total incident pulse energy for this interval of time is $E_{inc} = E_0 \nu t_{xo}$.

Thus, the ratio between the total left-over energy and incident energy becomes, after substituting $E_{tlo}$ from the equation (11) and $t_{xo}$ from (13):

$$E_{tlo}/E_{inc} = 1/3 \quad (16)$$

It is also interesting to note that if the source's pulse sequence is applied to a time interval t shorter than the cross-over time for a given set of laser parameters, (i.e., t<$t_{xo}$) then obviously the valve of $t_{xo}$ from equation 9 cannot be used, and the ratio R of left-over residual energy to that of Total Incident Energy is given by:

$$R = \frac{E_{tlo}}{E_{inc}} = [1 - (2/3)a_r \nu (t/k)^{1/2}] \quad (17)$$

This is an important expression because it describes the ratio of left-over energy to incident energy for ALL interactions where the interaction time is less than the Cross-over time and thus all interactions where complete ablative removal of the heat from ANY of the incoming pulses is not achieved.

Again, analysis of the ratio of equation (17) shows that the ratio, R,

Decreases with $v$

This is interesting because the ratio R, unlike $E_{tlo}$, decreases with increasing pulse repetition rate and does not show a maximum. This behavior is so because while the total incident energy increases with frequency, the total left-over energy decreases with as more ablation pulses are packed into each time interval.

Decreases with $a_r$ and f.

The larger the amount of material removed with each pulse, the more heated material that is removed and the less left-over energy remaining in the material.

Decreases with the square root of the time ($t^{1/2}$) the pulse train is interacting.

The longer the ablation interaction continues the more heated material (and its content of thermal energy) is removed.

Increases with one over the square root of the thermal diffusivity k.

Again, with a larger thermal diffusivity, a larger portion of the left-over residual energy remaining after each pulse is able to diffuse to deeper regions of the material and the less likely this energy is to be removed through ablative interaction with subsequent pulses. Three other important observations are:

We also see from equation (17) that for all cases where $t_{xo}$ has been reached, $t_{xo}$ can be substituted and R is equal to ⅓ (R=⅓) or, put differently, about 33.3% of the incident energy arriving between the last pulse M and pulse (M-$vt_{xo}$) is left in the material as residual energy.

R is independent of $a_r$ (and f) if $t_{xo}$ has been reached. In this case, the ratio R of the left-over energy to the incident energy is constant and equal ⅓ regardless of the amount of material removed with each pulse and the ratio of this amount to that of the optical deposition depth.

This point is important because it clearly demonstrates that once a high pulse repetition rate ablation is allowed to go on for a sufficiently long period of time so that txo is reached, the control of the residual heat in the material is dominated by the total removal of most of the interaction energy by the rapid sequence of pulse themselves.

Finally, it is also important to note that if $v$ is such that the cross-over is not reached, $a_r$ (and f) do play a role in the determining the amount of left-over thermal energy.

Ultimately, however, it is not the ratio R that is of most importance in determining the amount of thermal damage that can be caused, but rather, the absolute value of the total left over energy, left in the tissue following an interaction of a pulse train. This expression was given by equation (11) for a general time $t<t_{xo}$.

$$E_{tlo}=E_0 vt[1-(⅔)a_r v(t/k)^{1/2}] \quad (18)$$

This expression clearly indicates the presence of a maximum $E_{tlo}$ as the pulse repetition rate $v$ is varied. This is so because there are two competing effects to the pulse repetition rate $v$. First, $E_{tlo}$ is increased with the increase in the deposited energy which increased with $v$. On the other hand, two: as the pulse repetition rate $v$ is increased so does the removal rate due to the ablation term (second term) in equation (18).

To find the maximum we differentiate $E_{tlo}$ with respect to $v$, $$d(E_{tlo})/dv = E_0 t[1-(4/3)a_r v(t/k)^{1/2}]$$

A

When the pulse repetition rate is very low i.e., $v \to 0$ Then from (18) $E_{tlo} \to 0$ as well [More precisely $E_{tlo}$ is simply equal to the incident energy deposition rate which is:

$$\epsilon_0 (A(\delta-a_r))v$$

With $\epsilon_0$ being the incident energy density Per Pulse. Obviously $E_{tlo}=\epsilon_0 A(\delta-a_r)$ per second for 1 Hz and $E_{tlo}$ goes to zero as $v$ goes to zero].

B

By setting the derivative (19) equal to zero, we find the frequency for which maximum left-over energy occurs.

$$v_{max}=(¾)(1/a_r)(k/t)^{1/2} \quad (20)$$

Substituting back in (8) yields $$(E_{tlo})_{Max} = (3/8)E_0(tk/a_r^2)^{1/2} \quad (21)$$
$$= (3/8)E_0 t v_0$$
$$= (3/8)Einc$$

Also we note that when:

C $$v=3/(2a_r)(k/t)^{1/2} \quad (22)$$

$$E_{tlo}=0 \quad (23)$$

Ci

If we are evaluating the above at $t=t_{xo}$ for some frequency $v_0$ then, by the definition of $t_{xo}$ ($v_0=(1/a_r)(k/t_{xo})^{1/2}$) equation 22 becomes:

$$v=3/2v_0 \quad (24)$$

and, $$E_{tlo}=0 \quad (25)$$

In other words:

Since for a time selected for evaluation, $t_0$ there is a corresponding frequency $v_0$ for $t_0$ which is the cross-over time, operating at a frequency given by ($3v_0/2$) will result in no residual thermal energy deposition leftover in the material.

We can also rewrite case B in terms of $v_0=(1/a_r)(k/t_o)^{1/2}$ since equation (20) can be expressed as:

Bi $$v_{max}=(¾)v_0 \quad (26)$$

So that equation (8) yields $$E_{tlo}Max = (3/8)E_0(tk/a_r^2)^{1/2} \quad (27)$$
$$= (3/8)E_o t v_0$$
$$= (3/8 Einc@crossOver$$

Finally when $v$ is exactly equal to $v_0$ then the time is precisely the crossover time and (recall from earlier discussion),

D $$v=v_0 \quad (28)$$

So that equation (18) yields $$E_{tlo}=(⅓)E_0 v_0 t \quad (29)$$

Or $$E_{tlo} = \tfrac{1}{3} E_{inc} \quad (30)$$

@ cross-over time $t_{xo}$

Figure 13:
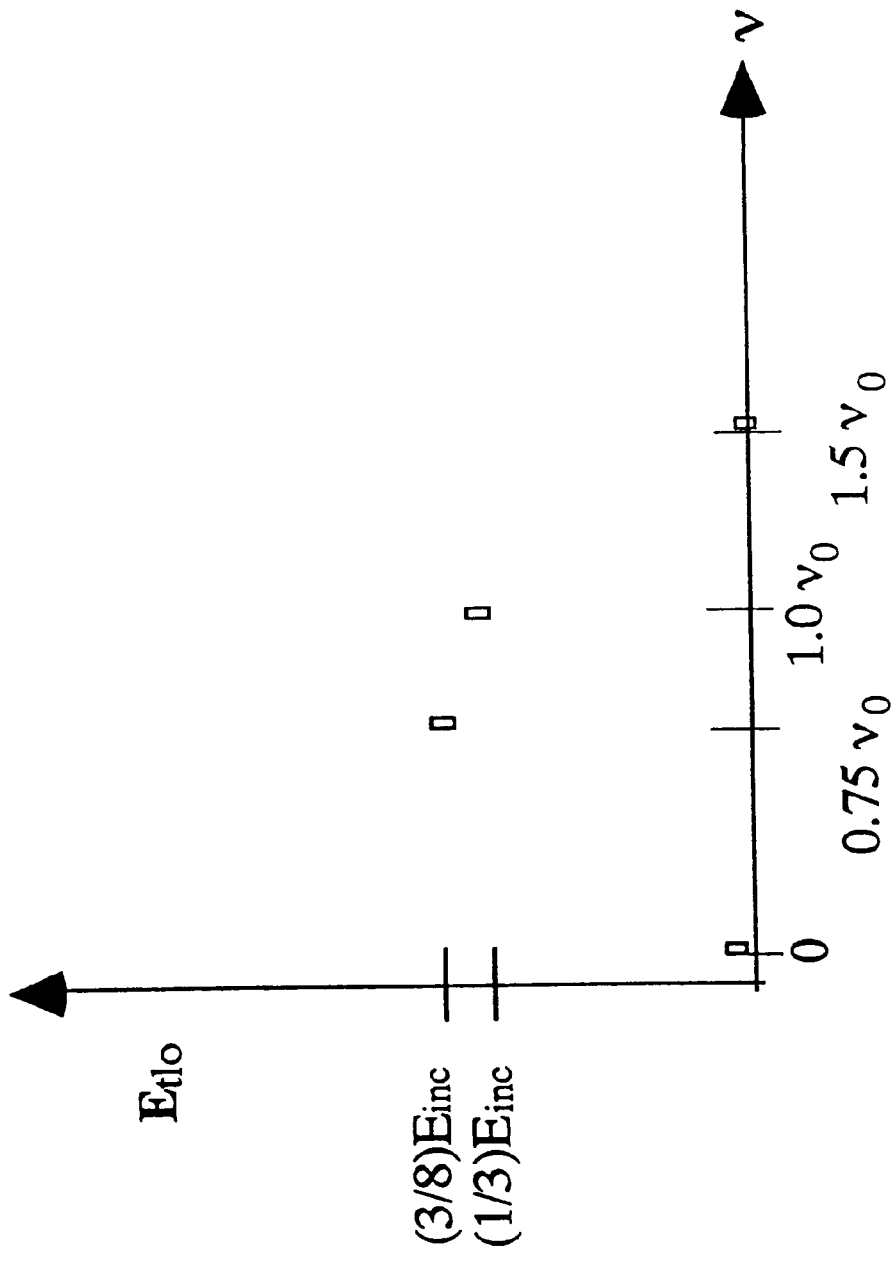
FIG. 13, is a graphical representation of the calculated amount of left-over energy as a function of the source pulse repetition rate.

The dependence of $E_{tlo}$ on the pulse repetition rate $v$ is illustrated in FIG. 13.

From FIG. 13 and from $$E_{inc} = E_0 v_0 t$$

$$v_0 = (1/a_r)(k/t)^{1/2}$$

We see that both Einc and $v_0$ are proportional to $1/a_r$. Thus the larger $a_r$ is the lower $E_{tlo}$ is and the lower the frequency $v_{max} = (\tfrac{3}{4}) v_0$ at which the maximum total left-over energy, $E_{tlo}$ occurs. (i.e., the entire curve in the figure above shift to the left and to the bottom)

Typical numbers for a 1 second treatment with a 1 KHz, 1 mJ system, would be:

$E_{inc} = E_0 v_0 t =$
(1 mJ) (1000 pulses/sec) (1 sec) = 1 J
($E_{inc}$ = 1 J)
which yield a maximum left-over energy of only
$E_{tlo-max}$ = 0.33 J = 330 mJ
at $v$ = 750 Hz Since the actual amount of per-pulse energy transformed to heat is only 10% to 30%, the total left-over energy in the target is in the range of 30 to 100 mJ per interaction. Also note that because of the self-heat removal described by the principle of operation of the present invention—this total amount of left-over energy is constant regardless of the length of overall operation time. This feature is a unique characteristic of the operation of the present invention.

Quasi-Dynamic Relationship between the Ablation Front and the Thermal Diffusion Front As we saw from the discussion above, all of the thermal energy deposited in the target material prior to the last cross-over time interval txo, is completely removed from the material by subsequent pulse ablation. An interesting question however, is how much ahead of the ablation front can the thermal energy from each pulse get?

The answer is given again by FIGS. 5a and 11. For each pulse, the distance "diffusion front to ablation front is given by:

$$\Delta X = X_{diff} - X_{abl} = (K^{1/2} t^{1/2} - (a_r v) t \quad (31)$$

Up to the point where $\Delta X$ becomes negative (i.e., when all heat is removed by the ablation front).

If we wish to find the maximum distance $\Delta X$ as a function of time we simply take the derivative with respect to time then:

$$d(\Delta X)/dt = \tfrac{1}{2}(K^{1/2}/t^{1/2}) - (a_r v) t \quad (32)$$

Which gives a value of:

$$t_{max} = k/(2a_r v)^2 = t_{xo}/4 \quad (33)$$

i.e., the maximum distance that the thermal energy diffusion front gets ahead of the ablation front occurs at one fourth of the cross-over-time.

Substituting this in the expression for $\Delta X$ above gives:

$$\Delta X_{max} = k/4(a_r v) \quad (34)$$

For our exemplary 1 KHz 1 $\mu$m/pulse water-like system this means about 40 $\mu$m ahead of the ablation front.

$\Delta X_{max}$ ~40 $\mu$m
For a 100 KHz system:
$\Delta X_{max}$ ~0.4 $\mu$m
A 100 Hz system on the other hand will result in a distance of 400 $\mu$m
For a 10 Hz system:
$\Delta X_{max}$ ~4 mm
While a 10 Hz system with ablation rate of 10 $\mu$m per pulse will yield $\Delta X_{max}$ ~0.4 mm The calculation above also holds for the distance that each one of the last M–$vt_{xo}$ pulses has reached ahead of the ablation front when the system is turned off. The time t in equations 31–34 above simply corresponds to pulse number M–tv where M is the last pulse in the pulse train.

Thus, the pulse whose heat has diffused the furthermost from the ablation front when the laser is turned off is given by pulse number: M–$t_{max}v$ Where M is the last pulse and $t_{max}$ is given by equation (33).

A more elaborate way for describing the interaction is provided by the additional discussion below:

A) A SINGLE PULSE INTERACTION:

Light is deposited within an optical deposition zone, $\delta$. Note, however, that the optical deposition zone changes with wavelength, material type, and the light intensity. It is, for example, different for low intensity pulses as compared to high intensity pulse. $\delta$ may also change within a single pulse as the leading edge of the pulse modifying the optical properties of the target material.

Depending on how the incident pulse optical energy $E_0$ is deposited in the material (i.e., the optical energy distribution and coupling to the matter as a function of time and spatial location), some of the material will be ejected (e.g., to a depth X=$a_r$) and some will be permanently modified, (e.g., to a depth $X_{ir}$) while the rest of the material will either not be irreversibly modified or may be unaffected by the incident energy at all.

The exact interaction path may be thermally dominated (e.g., vaporization or rapid vaporization of matter and water, leading to explosive ejection of material), mechanically dominated (generation of shock wave, mechanical transient, or spallation), chemical alteration of the material (changes in chemical properties of the target matter are effected), or plasma-mediated (e.g., either multiphoton ionization or thermo-ionization of the material and the material and the creation of an ion/electron plasma which, in turn, alter pulse energy coupling, reflection, or transmission into the material).

The complex dependence of $\delta$, and $a_r$ both static and dynamic properties of the beam and targeted material can, according to this invention, be simplified. Using experimental technique one can observe the ablation rate $a_r$ (i.e., the amount of ablated material per pulse), the depth of the zone of irreversible modification (created by a single pulse), optical deposition depth $\delta$.

If $a_r$ and $\delta$ are known, the mount of energy left by a single pulse, $E_{lopp}$, can then be estimated:

$$E_{lopp} = E_0(1 - a_r/\delta) \quad (35)$$

Where $E_0$ is the incident energy of each pulse. The amount of energy left over in the tissue after each single pulse is proportional to $a_r/\delta$. Thus, as $a_r/\delta$ is diminished (either because $a_r$ becomes larger or because $\delta$ becomes smaller) $E_{lopp}$ diminishes and becomes smaller as well.

The optical energy in the pulse-initially deposited in the optical deposition zone $\delta$, begins to diffuse deeper into the tissue with a characteristics diffusion rate given by:

$$dZ/dt = (k/t)^{1/2} \tag{36}$$

where k is the material thermal diffusivity coefficient (for example, for water, k=1.4 $10^{-7}$ m²/sec.

Depending on the pulse duration, the thermal diffusion into the material will take place either already during the pulse (during the optical deposition time) or mostly after the optical energy deposition has been coupled.

If the pulse duration $\tau$ is such that:

$$\tau < \delta^2/k \tag{37}$$

when heat does not diffuse out of the optical deposition zone during the pulse duration and the optical deposition process is known as "thermally confined".

For a dielectric with water-like thermal diffusivity, k=1.4 E−7 m²/sec and thermal energy diffuses about a single $\mu$m within a $\mu$s time duration. If we consider pulses shorter than 100 microsecond the diffusion distance is only 10 micrometer. IN 10 ms, thermal energy diffusion is limited to 100 micrometer. For most practical situations the optical deposition is greater than at least 1 $\mu$m and more likely between 1 and several tens $\mu$m. Thus, for most practical situations under consideration of this invention, heat does not substantially diffuse out of the optical zone during the optical energy deposition cycle.

Figure 14:
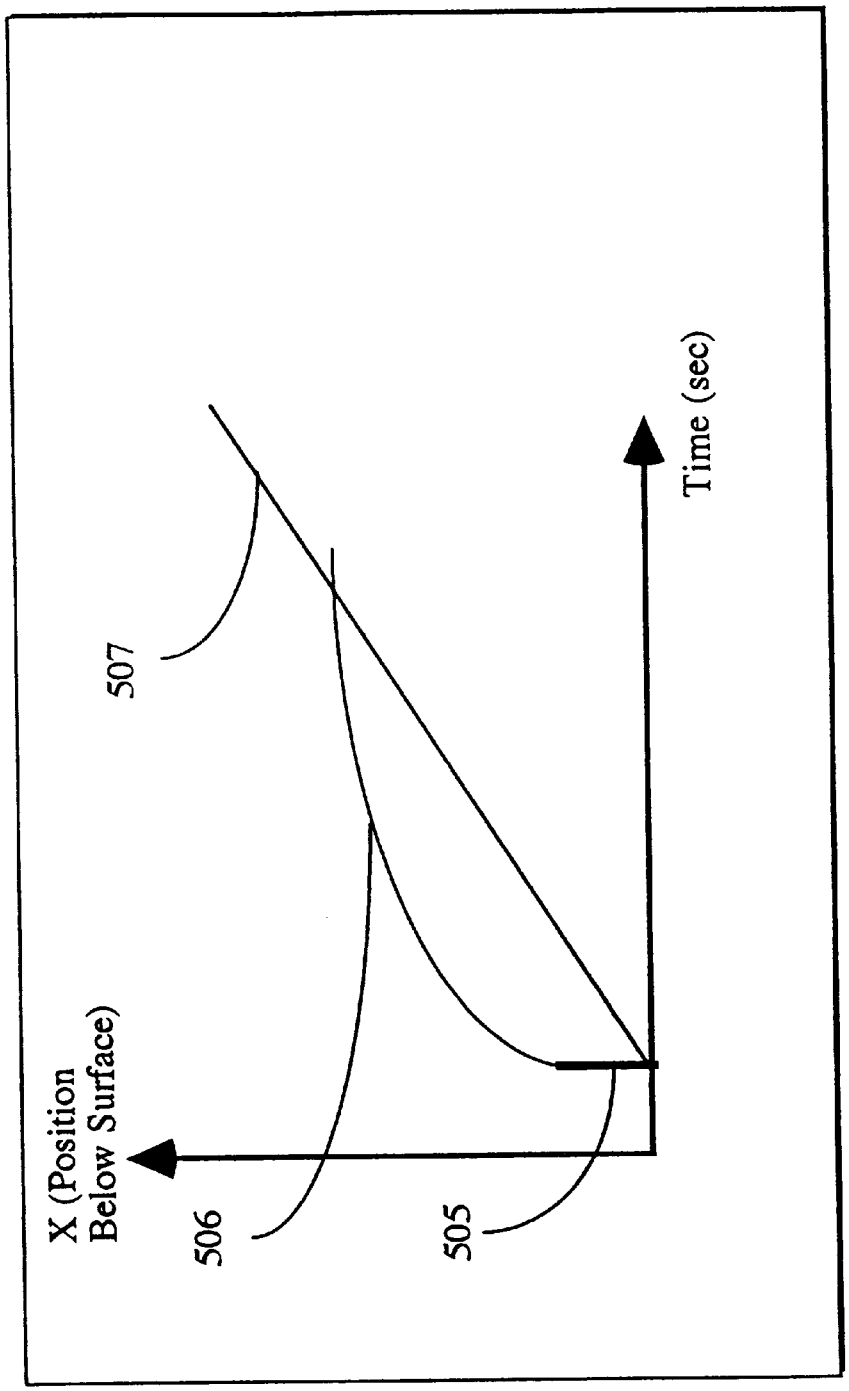
FIG. 14, is a graphical representation illustrating the relationship between the thermal diffusion front position following a single pulse interaction and the progressing ablation front due to subsequent pulses when the interaction is characterized by a significant optical penetration depth.

The situation can thus be approximated by the picture depicted in FIG. 14 where the horizontal axis depicts the time axis and the vertical axis depict the depth to which pulse energy has reached (either through optical or through thermal diffusion).

Optical energy is deposited to an optical deposition depth $\delta$, 505. The curved line 506 represents additional energy penetration due to thermal diffusion. The line 507 represents the propagation of the ablation front due to subsequent pulses removal of material. It shows that ultimately all the first pulse energy will be removed from the material.

We begin by calculating the time required for complete removal—by subsequent ablation pulses—of the entire amount of thermal energy deposited by the first pulse (or any arbitrarily selected pulse N in an incoming pulse train of M pulses).

The time, termed by the inventor cross-over time $t_{xo}$, is found by setting the distance reached by the thermal diffusion front, $Z_{thrm}$:

$$Z_{thrm} = \delta + (kt)^{1/2} \tag{38}$$

equal to the ablation front term:

$$Z_{abf} = a_r v t \tag{39}$$

Which leads to:

$$kt = (a_r v t - \delta)^2 \tag{40}$$

Which may be expanded to:

$$a_r^2 v^2 t^2 - (2\delta v a_r - k)t + \delta^2 = 0 \tag{41}$$

Defining the coefficient in front of the $t^2$ term as $\alpha$, and the one in front of the t-term as $\beta$ we have a simple quadratic equation with a solution:

$$t_{1/2} = [-\beta +/- (\beta^2 - 4\alpha\delta^2)^{1/2}]/(2\alpha) \tag{42}$$

If we substitute $\alpha$ and $\beta$ in Equation (42) we obtain:

$$t_{xo} = t_{1/2} = [(2a_r v \delta - k)/(2a_r^2 v^2)][1 +/- [1 - (4a_r^2 v^2 \delta^2)/ \tag{43}$$

$$(4a_r^2 v^2 \delta^2 = -(4a_r v \delta + k^2)]^{1/2}]$$

Equation (43) shows that the cross over time, the time at which the progressing ablation front will completely eliminates the thermal energy deposited by a single pulse of energy, is a complex function of k, ar, v and $\delta$.

This complicated relation can be simplified if we consider the two extremes:

A) $(2\delta v a_r) << k$
  (Thermal diffusion dominates the energy diffusion process)
  (e.g., If the ablation per pulse is on the order of the optical penetration which is on the order of a micrometer, and if with pulse repetition rate of about 1000 Hz, the term $(2\delta v a_r)$ is on the order of $10^{-9}$ while k is on the order of $10^{-7}$.)

In this case equation (43) reduces to the cross over times:

$$t_1 = k/(v a_r)^2 \tag{44}$$

and to the non-practical solution is $t_2 = 0$.

If on the other hand:

B) $(2 \delta v a_r) >> k$
  (for example if the optical penetration depth is on the order of a few millimeters or more)

Then, in this case the cross-over time is given by:

$$t_{1/2} \rightarrow t_1 = \delta/v a_r \tag{45}$$

B) Multiple-Pulse Effects:

An important contribution of the present invention is that after a time period equal to the cross-over time, $t_{xo}$, no thermal energy due to the pulse N under consideration remains in the target material. This is so due to the ablative removal by subsequent pulses.

FIG. 14 shows the relationship between the thermal diffusion front due to pulse number N and the progressing ablation front due to subsequent pulses. The inventor has recognized that the same figure may also represent the amount of heated material left in the target after an energy deposition by each of the N pulses (between pulse L and the last pulse M) due to the action of subsequent remaining pulses M−N that follow each pulse N.

Figure 15:
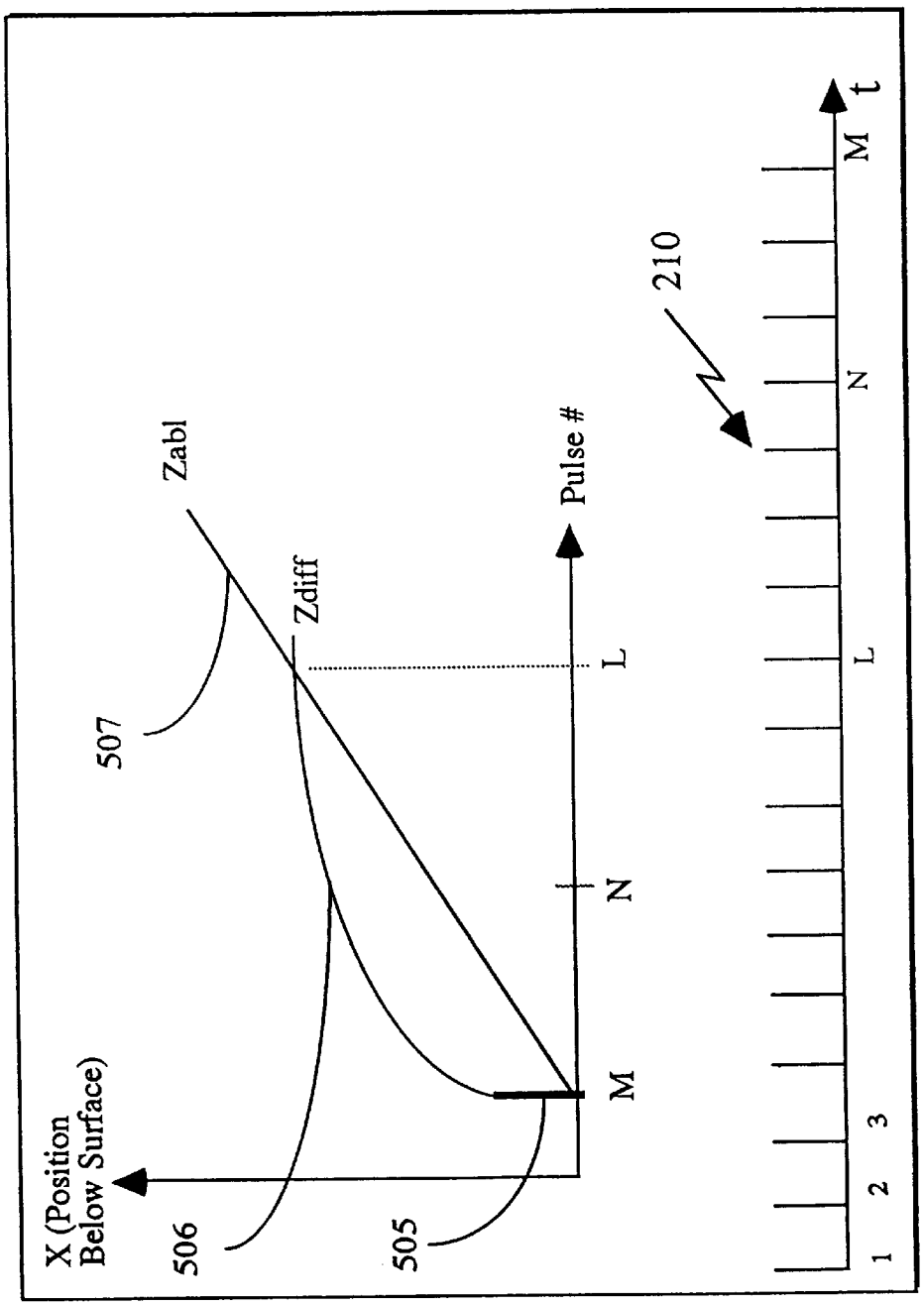
FIG. 15, is a graphical representation of the position of the thermal diffusion front (relative to the position of the surface at the time of each pulse deposition) at the time of pulse train termination when the interaction is characterized by a significant optical penetration depth δ. The figure also illustrate the position of the ablation front (relative to the position of the surface at the time of each pulse deposition) at the time of pulse train termination.

FIG. 15 depicts the position of the thermal diffusion front (relative to the position of the original surface) for each pulse at the time of pulse train termination, and also the position of the ablation front (relative to the position of the original surface) for each pulse at the time of pulse train termination.

The total amount of left-over energy due to a pulse train of M pulses (N=1, 2, 3, . . . L . . . M. Where M is the last pulse in the pulse train, and L is the pulse arriving at a time $t=t_{xo}$ before the pulse train termination) can be calculated.

As was mentioned above the thermal energy due to the first pulses in the train, (if the pulse train total time duration, T is longer than $t_{xo}$, i.e., $T > t_{xo}$) will be ablated away. This is the case if these pulses occur at times t such that $T - t > t_{xo}$. (i.e., if these pulses interact with the target in times earlier than the cross over time $t_{xo}$ prior to the end of the pulse train.

For the last few pulses (from pulse L to pulse M occurring at times t such that $T - t < t_{xo}$, the situation is different. These pulses do no have enough subsequent pulses behind them to have their own heat completely removed.

With the aid of FIG. 15, we can estimate the amount of total energy left over by these last pulses, (which is also the total amount of left over thermal energy $E_{tlo}$, due to the entire pulse train.

$$E_{tlo} = \sum [E_{lopp}(1 - Zabl/Zdiff)] \quad (46)$$

Where the summation is carried over the last M-L pulses. Since the incremental number of pulses in the sum is given by #=ν dt the summation can be written as an integral of the corresponding interval of time, i.e., the time from T to $T=_{txo}$.

Since the integration is invariant to the direction in time, we can simply integrate from t=0 to t=txo. Equation (46) thus becomes:

$$E_{tlo}=\nu E_{pp}\int 1-[t\nu a_r/(\delta=(tk)^{1/2})]dt \quad (47)$$

Where the integration is from t=0 to $t=t_{xo}$.

The integral (47) can be executed in parts leading to the following expression:

$$E_{tlo}=t_{xo}\nu E_{pp}-\nu^2 E_{pp}a_r\int tdt/(\delta+(tk)^{1/2}) \quad (48)$$

With the same limits of integration as in (47)

The integral in equation (48) is an indefinite integral and can be performed using Equation 19 on page 929 in the tables of indefinite integral given by Korn an Korn:
It is given by:

$$E_{tlo}=t_{xo}\nu E_{pp}[1-\nu^2 a_r(1/txo)(\zeta)] \quad (49)$$

Where:

$$\zeta=(1/k^2)[Y^3/3+(3/2)\delta Y^2+(3\delta^2 Y)-\delta^3 \ln Y]- \quad (50)$$
$$-\delta^3(29/6-\ln\delta)/k^2$$

and where
$$Y=\delta+(kt_{xo})^{1/2}$$

Equation (49) is the general expression for the left-over energy $E_{tlo}$.

Considering the limiting cases can simplify equation (48):

Limit i) THERMAL CONDUCTION DOMINATES ENERGY PROPAGATION $\delta/t<<(k/t)^{1/2}$ In this case Equation (48) yields:

$$E_{tlo}=E_{lopp}k/(3\nu a_r^2)=Einc/3 \quad (51)$$

Where:
$$E_{inc}=E_{lopp} \text{ txo } \nu$$

In this limit the cross over time is given by:
$$t_{xo}=k/(a_r^2 \nu^2)$$

In The Other Limit:

Limit ii) OPTICAL DEPOSITION DOMINATES ENERGY PROPAGATION $\delta/T<<(k/t)^{1/2}$ In this case equation 48 becomes:

$$E_{tlo}=t_{xo}E_{lopp}\nu[1-\nu a_r t_{xo}/(2\delta)]=E_{inc}/2 \quad (52)$$

Where:
$$E_{inc}=E_{lopp} \text{ txo } \nu$$

In this limits the cross over time as given by:
$$t_{xo}=\delta/(a_r\nu)$$

C) Left-Over Energy And Damage Zones Due To Multiple Pulse Action.

Table 1 summarizes the cross-over time $t_{xo}$, the thermal diffusion depth corresponding to $t_{xo}$, and the total incident energy, total left over thermal energy and the realistic values for $E_{tlo}$ (since only about 10–30% of the incident energy couples to the target material)—during $t_{xo}$. Finally the table also shows the expected depth of zones of irreversible damage.

The following system parameters are assumed for the example in table 1: Optical penetration depth, $\delta=1$ μm, ablation depth per pulse $a_r=1$ μm thermal diffusivity, $k=1.4 \cdot 10^{-7}$ m²/sec, and the incident energy per pulse Einc is assumed at 1 mJ.

TABLE 1

| ν | $t_{xo}$ (Sec) | $(tk)^{1/2}$ (m) | $E_{inc}$ (mJ) | $E_{tlo}$ (mJ) | $E_{tlo}$-realistic (only 10% coupled) | $Z_{damg}$ 0.1 mJ/μm |
|---|---|---|---|---|---|---|
| 100 | 10 | 1.2 E-3 | 1000 Diffusion Dominates | 330 | 33 | 330 μm |
| 300 | 1 | 4 E-4 | 300 | 100 | 10 | 100 |
| 1 KHz | 0.1 | E-4 | 100 | 33 | 3.3 | 33 |
| 3000 | 0.01 | 4 E-5 | 30 | 10 | 1 | 10 |
| 10 KHz | 0.001 | E-5 | 10 | 3.3 | 0.3 | 3 |
| 30,000 Hz | $10^{-4}$ | 4 E-6 | 3 δ-Zdiff "optical deposition dominates" | 1 | 0.1 | 1 |
| 100 KHz | $10^{-5}$ | E-6 | 1 | 0.3 | 0.03 | 0.3 |

In the above a damange energy threshold of approximately 0.1 mJ per μm was assumed.

Thus, for optical deposition depth δ of 1 micrometer one need not worry about δ in the expression for $E_{tlo}$ until a pulse repetition rate of over 10 KHz.

For this regime $\delta<<(tk)^{1/2}$
and $t_{xo}=k/(ar \nu)^2$
and $E_{tlo}=k E_0/(3 a_r^2 \nu)=E_{inc}/3$
For the regime $\delta>>(tk)^{1/2}$
$t_{xo}=\delta/(ar \nu)$
$E_{tlo}=E_0/(2 a_r)=E_{inc}/2$ at 100 KHz, δ~1 μm, the left-over energy is approximately 0.5 mJ, which corresponds to $Z_{damage}$ of about 5 μm.

It is worth noting that at 1 KHz the total left over energy is 33 mJ (regardless of how long the laser has been on. This should be contrasted, for example, with conventional Nd, Ho, or Er:YAG lasers with pulse energy on the order of 300 mJ per single pulse. (i.e., this KHz system $E_{tlo}$ is only 1% of the se lasers.)

D) Combined Effect Due To High $a_r/\delta$ Ratio And High PRR
   i) Thermal Conduction Dominates Energy Propagation $\delta/T<<(K/T)^{1/2}$
Here $E_{tlo}$ becomes:

$$E_{tlo}=(1-a_r/\delta)E_0 k/(3va_r^2)=(1/3)E_{inc}(1-a_r/\delta) \qquad (53)$$

Where $E_0$ is the per-pulse incident energy or $$E_{tlo}=E_0 k/(3va_r^2)-a_r/E_0 k/(3v\delta a_r) \qquad (54)$$

Thus, from equation (54) if $a_r$ approaches $\delta$ then the left-over energy (regardless of the pulse repetition rate) becomes negligible.
Also, if v becomes very large then the left over energy becomes negligible.
Thus, if either, $a_r$ appreciates $\delta$ or v becomes very large, then the total left-over energy becomes negligible.
On the other hand, if $a_r$ is very small or k is very large then the $E_{tlo}$ becomes larger.
i.e., if
  $a_r \rightarrow 0$
  or $k \rightarrow$ infinity
  then
    $E_{tlo} \rightarrow$ infinity
 ii) Optical Deposition Dominates Energy Propagation $\delta/t>>(k/t)^{1/2}$
   $E_{tlo}=(1/2)\ \delta\ E_0/a_r-(1/2)E_0$
thus,
  if $a_r \rightarrow \delta$
    $E_{tlo} \rightarrow 0$
But if
  $\delta>>a_r$
Then
  $E_{tlo} \rightarrow (1/2)E_0\delta/a_r$
This means that in cases where optical penetration is very large (e.g., $A_r^+$ ion laser of ~/cm) and ablation is small (e.g. ~/$\mu$m) (then the ratio $(a_r/\delta)$ is on the order of $10^{-4}$, and the total left-over energy is $E_{tlo}=(1/2)\ v\ t_{xo}\ E_0\ (1-ar/\delta)$, which approaches:
  $E_{tlo} \rightarrow (1/2)\ vt_{xo}\ E_0=(1/2)\ E_{inc}$
This is reasonable since only negligible ablative removal takes place.

As became clear from the above, part of the practice of the present invention is based on the requirement of removal of portion of the pulse energy by subsequent pulses. It is, therefore, important in the practice of the present invention to identify failure of at least some of the pulses to accomplish such ablative removal of heat so that the number of pulses may be reduced until operating parameters allow ablative removal of heat to be restored.

To identify an ablative event by a an electromagnetic pulse at least some luminescence emission is collected from the interaction site and delivered to a detector which then compare the emission intensity and spectral content to a predetermined reference characteristic ablative emission.

Figure 16A:
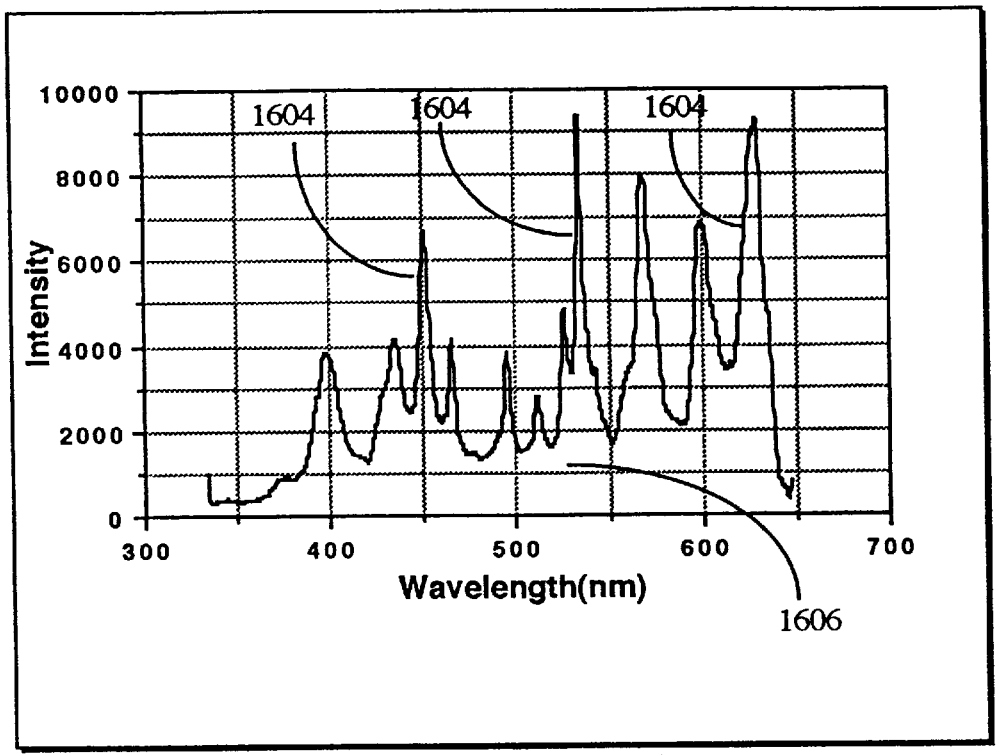
FIG. 16a, is a graphical representation of the spectrum or a luminescence emission collected from the ablation-induced plasma following interaction of a 15 ns Excimer laser with dentin.
Figure 16B:
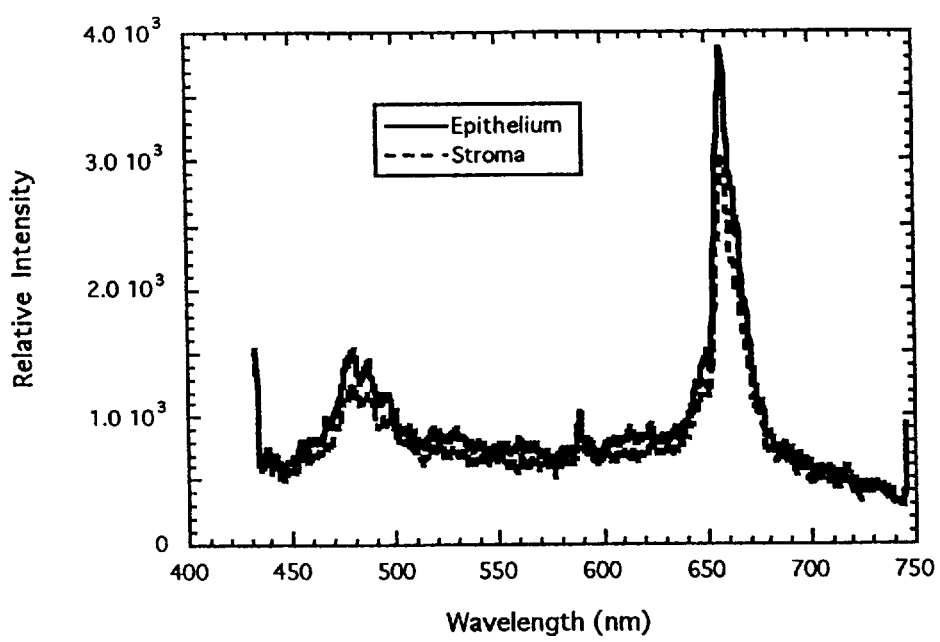
FIG. 16b, is a graphical representation of the spectrum or a luminescence emission collected from the ablation-induced plasma following interaction of a 15 ns Excimer laser with cornea target material.

FIG. 16a shows a typical emission spectrum from an ablative interaction followed by the formation of plasma. While the peaks 1604 are characteristic to the exemplary type of tissue ablated (Dentin) and to the Calcium atoms and ions generated by this interaction, the broad spectral continuum 1606 is a general characteristic of all ablation-induced plasmas and is indicative of ablative interaction. For comparison, the luminescence emission from ablative interaction of 193 nm beam with corneal tissue is also shown in FIG. 16b. While in this case, the characteristic tissue-specific Calcium peaks are absent and instead a single OH⁻ peak at 660 nm is the main dominating spectral structure, as was indicated above, the background emission is always present. In the absence of ablative interaction, no background emission can be detected.

Figure 17:
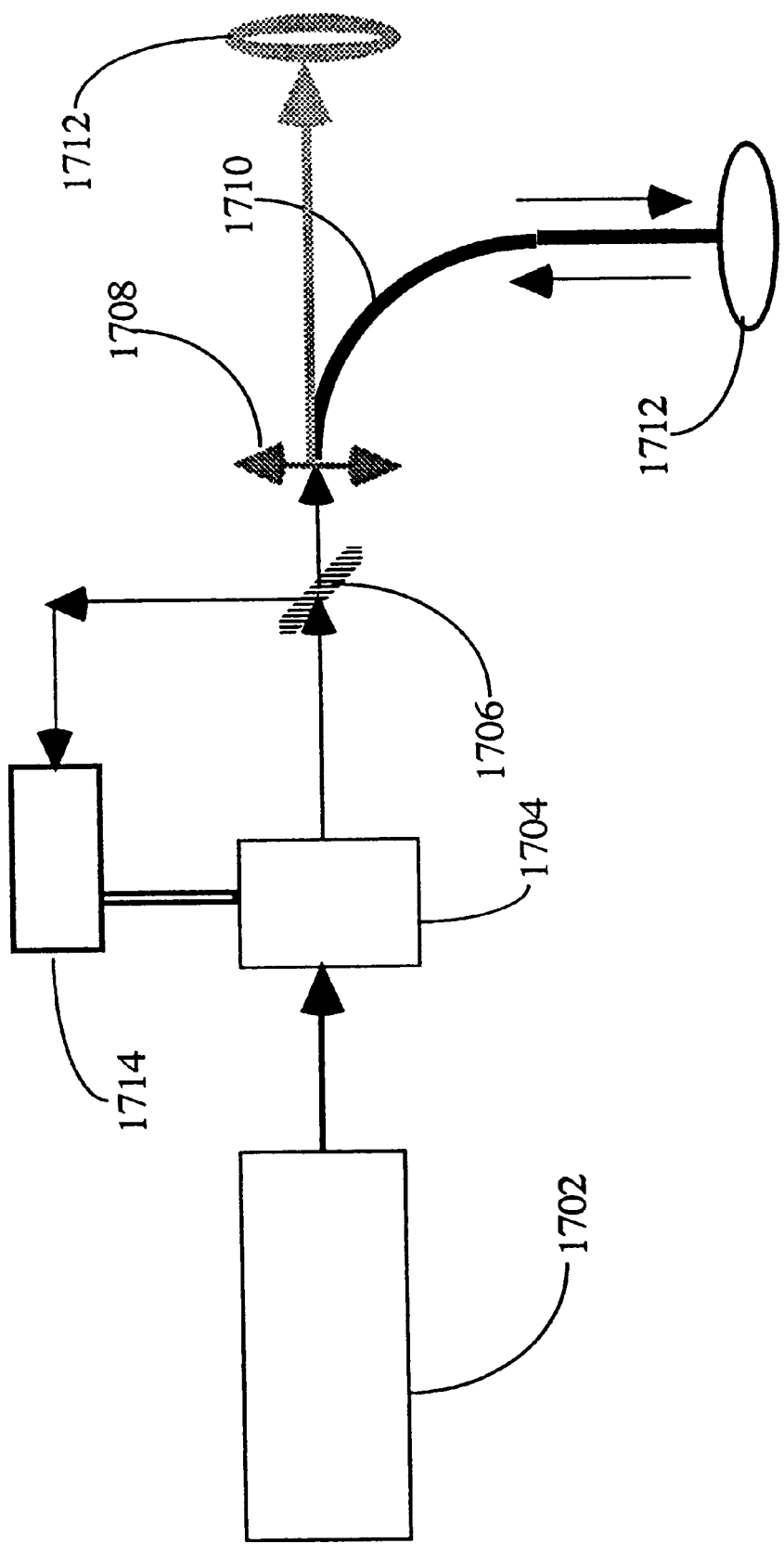
FIG. 17, is a block level schematic diagram illustrating a feedback system utilizing luminescence emission signal as indicator of ablative interaction.

FIG. 17 shows a typical collection and diagnostic setup with feedback means for monitoring ablation and controlling the Electromagnetic beam source. A source of electromagnetic radiation conforming with the principles of operation of the present invention (for example a pulsed laser source) 1702, emits a beam which is directed to a Pockels cell 1704. The Pockels cells acts as a shutter in response to instructions from the controller/computer 1714. In its normal operating condition the beam would be allowed to propagate through a beam splitter 1706 and into a focusing lens 1708. The focusing lens send the beam either directly into the target 1712 or through delivery fiber or hollow wave guide 1710 to the target 1712. Following the ablative interaction, luminescence emission from the ablated target site is collected by the same delivery system (for example, the fiber and imaging lens). The collected emission is then reflected by the beam splitter 1706 to the diagnostic/feedback/controller unit 1714. The unit 1714 consists for example, of a detector to detect the intensity level of the collected luminescence emission (or, alternatively, of a spectrometer to detect and evaluate both intensity and spectral distribution of the collected luminescence emission), of a computer processor to analyze and compare the collected radiation to that expected from ablation luminescence emission, and finally, means to feedback a signal to the control unit of the beam source so that adjustment to the source pulse repetition rate may be made.

Figure 18:
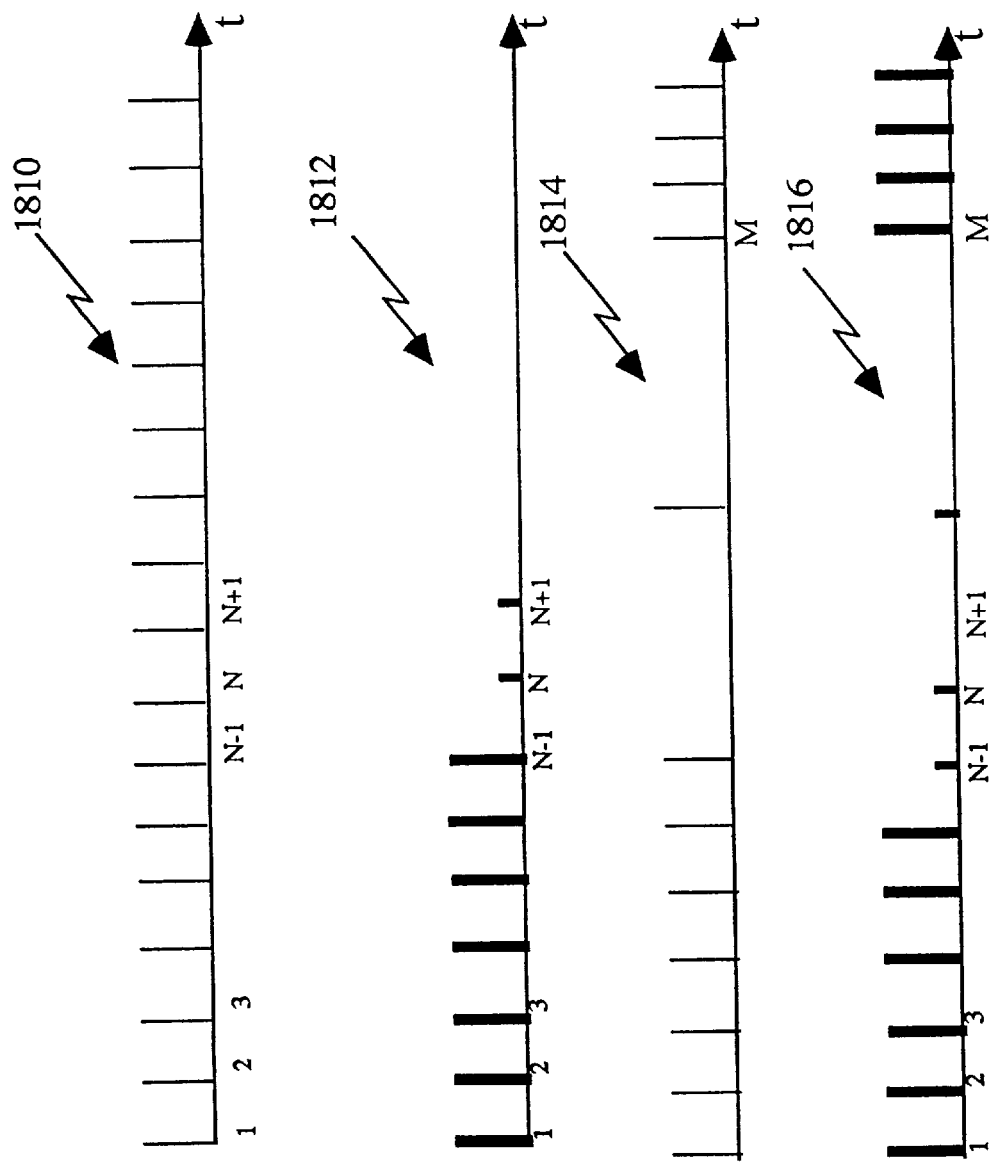
FIG. 18, is a graphical representation of a sequence of ablative pulses emitted in accordance with the practice of the present invention, the corresponding luminescence emission signal intensity, the adjustment induced by a feedback system to the pulse repetition rate, and the restored luminescence emission signal intensity in response to operator's corrective action.

If the diagnostic unit 1714 does not detect sufficiently high level of luminescence emission, the feed back circuit instructs the source control unit to slow the pulse rate to 10 pulses per second (or any exemplary X pulses per second pulse repetition rate, sufficiently low to avoid significant deposit of energy within the "linear" interaction regime). This process is shown in FIG. 18: here, the operating pulse repetition rate of Y Pulses per second is shown in 1810. The luminescence emission level corresponding to ablative interaction is shown for pulse number 1 through N−1 in 1812. When a decrease in luminescence emission level is detected for pulse N and N+1 in 1812, the corresponding pulse repetition rate is automatically changed to lower rate of X Pulses per second as shown in 1814. The lower repetition rate must be sufficiently low to bring non-ablative thermal deposition to a fraction of the value for threshold of irreversible material damage. Meanwhile, luminescence emission is continued to be monitored while the laser parameters are changed (either automatically through computer control or through actions taken by the operator). When Luminescence emission is restored following the action of pulse M as shown in 1816, the pulse repetition rate is restored to its original frequency as shown in 1814.

Ablative interaction is restored through one of the following adjustments:
  Increasing pulse energy or beam power
  Decreasing spot size (e.g. optically, or by moving the fiber/HWG/delivery arm etc. closer or further away from the target).
  Decreasing time scale
  Changing wavelength (e.g. through OPO/OPA nonlinear crystal insertion) to a more absorbing wavelength.

Alternatively, in the practice of the present invention and the use of an ablation detection feedback, the luminescence emission signal may be replaced by a transducer detector for detecting the presence of a mechanical recoil momentum, shock waves, thermoelastic stresses or any other transient mechanical or thermal effects which uniquely characterize an ablative interaction of the beam with the targeted material. Such a transducer feedback means may, in a manner similar to that described above, further provide a control signal in response to a change in the transducer detector output signal so that the electromagnetic source pulse repetition rate may be slowed down to an interrogative pulse repetition rate (or operation may be completely terminated) in response to such a feedback signal.

Such a transducer feedback means carrying a response signal which is a consequence of phenomena which occur only during an ablative event (such as, mechanical recoil momentum, shock waves, thermoelastic stresses or any other transient mechanical or thermal effects caused by the ablative interaction of the beam with the targeted materia) shall further provide a control signal. In response to such changes in the transducer detector output, the electromagnetic source pulse repetition rate may be slowed down or operation may be completely terminated.

Those skilled in the art will appreciate that the foregoing examples and descriptions of various preferred embodiments of the present invention are merely illustrative of the invention as a whole, and that variations in wavelength, pulse duration, pulse repetition rate, as well as beam energy density, may be made within the spirit and scope of the invention. Accordingly, the present invention is not limited to the specific embodiments described herein, but rather is defined by the scope of the appended claims.

What is claimed is:

1. A method for ablating material with directed energy, the method comprising:
   a) determining at least one characteristic of the material to be ablated, determining at least one characteristic of the material to be ablated comprising:
      i) ablating the material with a pulse of the directed energy;
      ii) determining the approximate quantity of the material ablated; and
      iii) determining the approximate quantity of the material permanently modified;
   b) defining a pulse of the directed energy which increases a ratio of a quantity of the material which will be ablated thereby with respect to a quantity of the material which will be permanently modified thereby, the characteristic(s) of the material determined in step (a) at least partially defining the pulse; and
   c) ablating the material with at least one pulse of directed energy which is defined according to step (b);
   d) wherein ablating the material with directed energy defined according to step (b) minimizes undesirable permanent modification of the material.

2. The method as recited in claim 1, wherein the directed energy comprises laser radiation.

3. The method as recited in claim 1 wherein the directed energy comprises light from at least one of an LED, a fluorescent lamp, and/or incandescent lamp.

4. The method as recited in claim 1 where the directed energy comprises incandescent light.

5. The method as recited in claim 1 wherein the characteristic(s) of the material determined comprise at least one of the thermal conductivity, effective electromagnetic energy penetration depth, material energy gap between valence and conduction bands, material density, material strength.

6. A device for ablating material with directed energy, the device comprising:
   a) a sensor for determining at least one characteristic of the material to be ablated;
   b) an energy radiating device for directing a pulse of energy at the material; and
   c) a controller for controlling the energy radiating device so as to define a pulse rate of the directed energy which increases a ratio of the quantity of the material which will be ablated thereby with respect to the quantity of the material which will be permanently modified thereby;
   d) wherein ablating the material with a plurality of directed energy pulses having a sufficient pulse rate as to increase the ratio of the quantity of the material which will be ablated thereby with respect to the quantity of the material which will be permanently modified thereby minimizes undesirable permanent modification of the material.

7. A device for material modification and processing, the device comprising:
   a) an energy radiating device for directing a plurality of pulses of energy at the material, the pulses having a sufficient pulse rate so as to increase a ratio of the quantity of the material which is ablated thereby with respect to quantity of the material which is permanently modified thereby; and
   b) a controller for controlling the energy radiating device, the controller configuring the pulse directed therefrom so as to increase a ratio of the quantity of the material which is permanently modified thereby;
   c) a means for modifying said energy radiating device output energy wavelength;
   d) wherein ablating the material with a plurality of directed energy pulses and with output parameters configured to increase the ratio of the quantity of the material which is ablated thereby with respect to the quantity of the material which is permanently modified thereby minimizes undesirable modification of the material.

* * * * *